(12) United States Patent
Callaghan

(10) Patent No.: US 10,096,161 B2
(45) Date of Patent: Oct. 9, 2018

(54) GENERATING AUGMENTED REALITY IMAGES USING SENSOR AND LOCATION DATA

(71) Applicant: Live Nation Entertainment, Inc., Beverly Hills, CA (US)

(72) Inventor: James Paul Callaghan, Los Angeles, CA (US)

(73) Assignee: Live Nation Entertainment, Inc., Beverly Hills, CA (US)

( * ) Notice: Subject to any disclaimer, the term of this patent is extended or adjusted under 35 U.S.C. 154(b) by 321 days.

(21) Appl. No.: 14/848,247

(22) Filed: Sep. 8, 2015

(65) Prior Publication Data

US 2016/0071325 A1 Mar. 10, 2016

Related U.S. Application Data

(63) Continuation-in-part of application No. 13/289,292, filed on Nov. 4, 2011, now abandoned, which is a continuation of application No. 13/160,789, filed on Jun. 15, 2011, now abandoned.

(60) Provisional application No. 61/355,000, filed on Jun. 15, 2010.

(51) Int. Cl.
| | |
|---|---|
| G09G 5/00 | (2006.01) |
| G06T 19/00 | (2011.01) |
| G06F 3/0346 | (2013.01) |
| H04W 4/02 | (2018.01) |
| G06Q 10/02 | (2012.01) |
| G06Q 30/06 | (2012.01) |
| G06T 7/70 | (2017.01) |

(52) U.S. Cl.
CPC .......... G06T 19/006 (2013.01); G06F 3/0346 (2013.01); G06Q 10/02 (2013.01); G06Q 30/06 (2013.01); G06Q 30/0643 (2013.01); G06T 7/70 (2017.01); H04W 4/02 (2013.01)

(58) Field of Classification Search
CPC ...... G06T 19/006; G06T 7/70; G06Q 30/0643
USPC ........................................................ 345/633
See application file for complete search history.

(56) References Cited

U.S. PATENT DOCUMENTS

| | | |
|---|---|---|
| 8,509,483 B2 | 8/2013 | Inigo |
| 8,933,970 B2 | 1/2015 | Saklatvala et al. |
| 9,525,787 B2 | 12/2016 | Bakthavachalu et al. |
| 9,569,465 B2 | 2/2017 | Folkens et al. |
| 9,575,995 B2 | 2/2017 | Folkens et al. |

(Continued)

*Primary Examiner* — Ryan R Yang
(74) *Attorney, Agent, or Firm* — Kilpatrick Townsend & Stockton LLP

(57) ABSTRACT

Embodiments relate to using sensor data and location data from a device to generate augmented reality images. A mobile device pose can be determined (a geographic position, direction and a three dimensional orientation of the device) within a location. A type of destination in the location can be identified and multiple destinations can be identified, with the mobile device receiving queue information about the identified destinations from a server. A first image can be captured. Based on the queue information, one of the identified destinations can be selected. The geographic position of each identified destination can be identified, and these positions can be combined with the mobile device pose to generate a second image. Finally, an augmented reality image can be generated by combining the first image and the second image, the augmented reality image identifying the selected one destination.

20 Claims, 34 Drawing Sheets

(56) References Cited

U.S. PATENT DOCUMENTS

| | | |
|---|---|---|
| 9,639,867 B2 | 5/2017 | Folkens et al. |
| 9,665,595 B2 | 5/2017 | Folkens et al. |
| 9,767,362 B2 | 9/2017 | Saklatvala |
| 9,786,246 B2 | 10/2017 | Feiner et al. |
| 9,830,522 B2 | 11/2017 | Mazur et al. |
| 9,846,942 B2 | 12/2017 | Wang et al. |
| 2012/0105475 A1* | 5/2012 | Tseng ................ G01C 21/3611 345/633 |
| 2012/0195460 A1 | 8/2012 | Inigo |
| 2013/0328927 A1* | 12/2013 | Mount ................ G06T 19/006 345/633 |
| 2014/0071164 A1 | 3/2014 | Saklatvala et al. |
| 2014/0240350 A1* | 8/2014 | Chen ................ G01C 21/206 345/633 |
| 2014/0313226 A1 | 10/2014 | Feiner et al. |
| 2015/0286658 A1 | 10/2015 | Folkens et al. |
| 2016/0314622 A1 | 10/2016 | Davis et al. |
| 2017/0337747 A1 | 11/2017 | Hull |

* cited by examiner

GENERATING AUGMENTED REALITY IMAGES USING SENSOR AND LOCATION DATA

CROSS-REFERENCE TO RELATED APPLICATIONS

This application is a continuation-in-part of U.S. patent application Ser. No. 13/289,292 (the '292 Application), currently pending, filed on Nov. 4, 2011, which is continuation of U.S. patent application Ser. No. 13/160,789, filed on Jun. 15, 2011, which claims the benefit and priority of U.S. Provisional Application No. 61/355,000, filed Jun. 15, 2010, each of these applications hereby being incorporated herein by reference in their entirety for all purposes.

FIELD

This disclosure relates in general to methods and systems for highlighting physical features using a mobile device. More specifically, an augmented reality system is described that identifies features within a geographic location.

BACKGROUND

When a person is in a location having destinations of different types, it can often be difficult to evaluate criteria and select from multiple destinations. Once a destination is selected, it can be difficult to navigate to the destination. Approaches to solving these problems do not provide dynamic information about the destinations, don't have an intuitive way of moving to a selected destination, and aren't adapted to specific types of locations where large groups of people congregate, and many competing types of destinations exist.

SUMMARY

Some embodiments relate to using sensor data and location data from a device to generate augmented reality images. A mobile device pose can be determined (a geographic position, direction and a three dimensional orientation of the device) within a location. A type of destination in the location can be identified and multiple destinations can be identified, with the mobile device receiving queue information about the identified destinations from a server. A first image can be captured. Based on the queue information, one of the identified destinations can be selected. The geographic position of each identified destination can be identified, and these positions can be combined with the mobile device pose to generate a second image. Finally, an augmented reality image can be generated by combining the first image and the second image, the augmented reality image identifying the selected one destination.

In some embodiments, a process for linking mobile devices at an event using groups based on seating and activity according to an embodiment;

In some embodiments, a system automatically groups attendees in a venue based on affinity groups. Affinity groups can be based on a broad range of characteristics, including those retrieved from stored information about attendees and characteristics determined from behavior at the event, e.g., movement, seating, etc.

In some embodiments, a process uses the displays of multiple mobile devices to display a single image at an event, with each device becoming a pixel of the displayed image. A still image (or a video frame) can be divided up and sent to individual devices with displays (phones, tablets, smart watches) as well as displays in the venue. When enough devices are used, and the combination is viewed from a sufficient distance, the still image (or moving video) is visible.

In some embodiments, images are automatically received from multiple mobile devices at an event according to different advantageous factors. Devices can be selected based on their current viewing position, proximity to an event of interest, capability of the device, speed of connection to the device, etc. Once selected, embodiments can automatically trigger the capture of an image (or video) for collection, optional aggregation and display.

In some embodiments, captured sounds are automatically received from multiple mobile devices at an event according to different advantageous factors. Devices can be selected based on their current capture position, proximity to an event of interest, capability of the device, speed of connection to the device, etc. Once selected, embodiments can automatically trigger the capture of sound for collection, optional aggregation and display.

In some embodiments, sounds are automatically outputted from multiple mobile devices at an event according to different advantageous factors. Devices can be selected based on their current output position, proximity to an audience of interest, capability of the device, speed of connection to the device, etc. Once selected, embodiments can automatically trigger the output of sound.

An embodiment of a data presentation sculpture is described.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

BRIEF DESCRIPTION OF THE DRAWINGS

The present disclosure is described in conjunction with the appended figures.

In the appended figures, similar components and/or features can have the same reference label. Further, various components of the same type can be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It is understood that various changes may be made in the function and arrangement of elements without departing from the spirit and scope as set forth in the appended claims.

Figure 1:
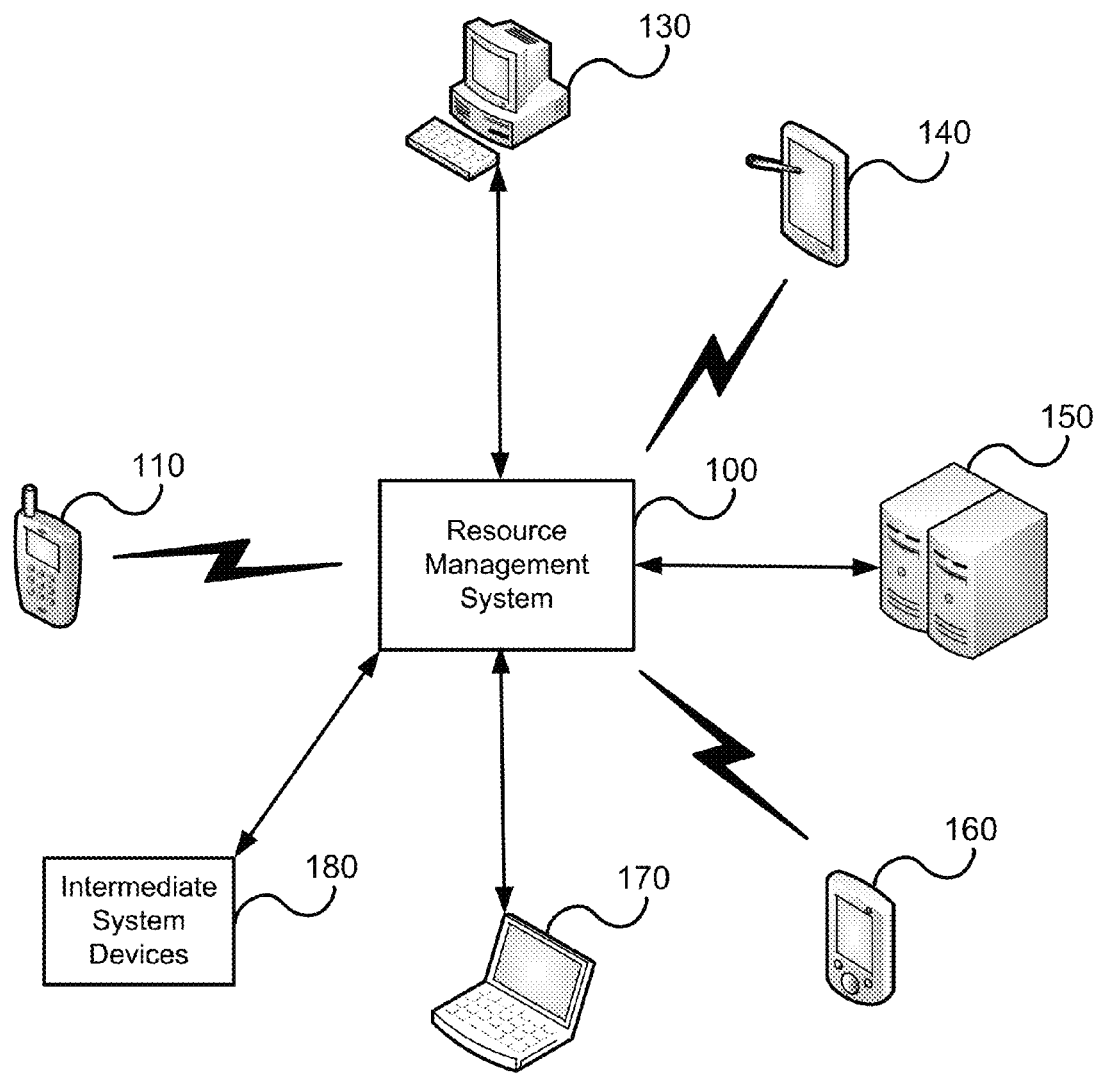
FIG. 1 depicts a block diagram of an embodiment of a resource management system.

Referring first to FIG. 1, an embodiment of a resource management system 100 is shown connected with various devices 110, 130, 140, 150, 160, 170, and 180. The various devices 110, 130, 140, 150, 160, 170, and 180 may each connect with the resource management system 100 in order to access an item or items of a resource controlled by the resource management system 100. Further, the resource management system 100 controls whether or not the various devices 110, 130, 140, 150, 160, 170, and 180 are granted access to resources. The various devices 110, 130, 140, 150, 160, 170, and 180 may access the resource management system 100 using mobile apps, web sites, call centers, venue box offices, application program interfaces (APIs), etc.

Mobile device 110 may connect to the resource management system 100 via a web browser displayed on a display of the device, which facilitates a webpage for accessing the item or items of the resources. Desktop computer 130 may use a desktop computer to connect to the resource management system 100 via a web browser, which facilitates a webpage for accessing the item or items of the resources. Tablet 140 may connect with the resource management system 100 via a web browser displayed on a display of the tablet device, which facilitates a webpage for accessing the item or items of the resources. The portable and/or handheld electronic devices may include, for example, mobile phones, personal digital assistant (PDA) devices. Laptop computer 170 may connect to the resource management system 100 via a browser displayed on a display of the laptop computer, which facilitates a webpage for accessing the item or items of the resources. Lastly, intermediate system devices 180 may include devices that enable brokers, group accessors, and/or wholesale accessors to access the items in a primary environment and control access to rights to the items in a secondary environment. For example, the intermediate system devices 180 may be enabled to grant access to the rights to the items accessed in the primary environment to the various devices 110, 130, 140, 150, 160, 170, and 180 in a secondary environment. The intermediate system users 180 may connect to the resource management system 100 to access the resources using any of the means discussed above.

In some cases, bot devices 150 connect to the resource management system 100 to access the resources. Bot devices 150 include a server or server farm storing software, apps or scripts that automatically access all available items of resources without the need for user input by a human. Typically, bot devices 150 access or reserve available items in an abusive manner by accessing a large portion of available items and providing rights to the reserved items to other users, thereby preventing fans (e.g., human users) from accessing the items directly from the resource management system 100. That is, bot devices 150 do not access the resources in order to attend the event, whereas, fans and human users typically access the resources in order to attend the event. Further, the apps or scripts used by the bot devices 150 may transmit requests to access the item or items via, for example, a webpage, at speeds not possible by human users.

Figure 2:
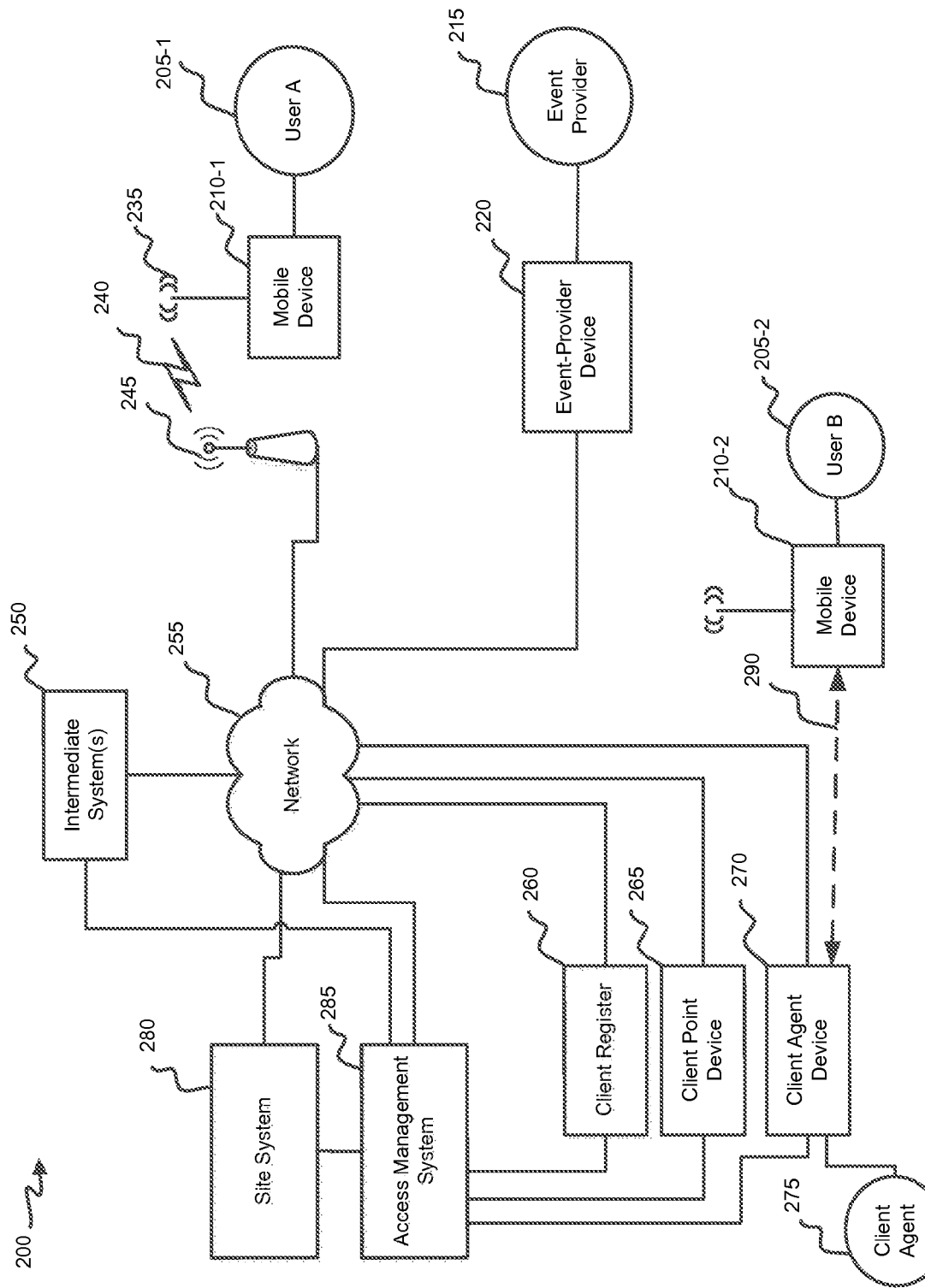
FIG. 2 depicts a block diagram of an embodiment of a resource access-facilitating interaction system.

FIG. 2 depicts a block diagram of an embodiment of a resource management system 100, according to an embodiment of the present disclosure. Mobile device 210 (which can be operated by a user 205) and an event-provider device 220 (which can be operated, controlled, or used by an event provider 215) can communicate with an access management system 285 directly or via another system (e.g., via an intermediate system 250). Mobile device 210 may transmit data to access point 245, which is connected to network 255, over communication channel 240 using antennae 235. While FIG. 2 illustrates mobile device 210 communicating with access point 245 using a wireless connection (e.g., communication channel 240), in some embodiments, mobile device 210 may also communicate with access point 245 using a wired connection (e.g., an Ethernet connection). Mobile device 210 can also communicate with one or more client devices, such as a client agent device 270 operated by a client agent 275, a client register 260 or a client point device 265 using a wired or wireless connection. In addition, using the access management system 285, an event provider 115 can identify an event, a parameter of attending the event, a date or dates of the event, a location or locations of the event, etc. Each inter-system communication can occur over one or more networks 255 and can facilitate transmission of a variety of types of data. It will be understood that, although only one of various systems, devices, entities and network are shown, the resource management system 100 can be extended to include multiple of any given system(s), device(s), entity(ies), and/or networks. Site system 280 is described further with the description of FIG. 10 below.

Access management system 285 can be configured to manage a dynamic set of access rights to one or more resources. More specifically, access management system 285 can track which resources are to be made available to users, specifications of the resources and times at which they will be available. Access management system 285 can also allocate access rights for resources and facilitate transmissions of notifications of the available rights to a set of user devices. For example, access management system 285 can alert users of the availability via a website, app page or email. As another example, access management system can transmit data about access rights and resources to one or more intermediate systems 250, which can facilitate distribution of access-right availability and processing of requests for such rights.

Notifications of available access rights can be accompanied by options to request that one or more access rights be assigned to a user. Therefore, user 205 can provide input to mobile device 210 via an interface to request such assignment and provide other pertinent information. Intermediate system 250 and/or access management system 285 can process the request to ensure that the requested access right(s) remain available and that all required information has been received and, in some instances, verified. Thereafter, access management system 285 can assign one or more access rights to the user, e.g., matching the access rights requested by the user.

Assigning an access right can include, for example, associating an identifier of the right with an identifier of a user, changing a status of the right from available to assigned, facilitating a cease in notifications that the access right is available, generating an access-enabling code to use such that the corresponding access will be permitted and/or generating a notification to be received at mobile device 210 confirming the assignment and/or including data required for corresponding access to be permitted.

In some instances, a resource is at least partly controlled, by a client. The resource may be accessed at a particular location or structure, and a variety of client devices may be present at the location so as to facilitate usage of an access right. Exemplary client devices can include client agent device 270, which can be one operated by a client agent 275 (e.g., a human client agent), a client register 260 (e.g., which can operate independently of an agent and/or can be connected to or include a device that, while in a locked mode, can impede resource access, such as a turnstile) and client point device 265 (e.g., which can operate independently of an agent and/or can be positioned at or around the resource-associated location. For example, in some instances client agent device 270 can be operated by an agent at a location for a resource that is an event ("event resource") taking place at the location. In this example, client agent device 270 is used by an agent that is manning an entrance to the location (e.g., which can include, for example, a location of a structure or a geographic region) or a part thereof; client register 260 can be or can be connected to a turnstile, gate or lockable door that is positioned along a perimeter or entrance to a resource-associated location or part thereof; and client point device 265 can be an electronic device positioned at or within a resource-associated location.

In some instances, mobile device 210 performs particular functions upon detecting a client device and/or the contrary. For example, mobile device 210 may locally retrieve or request (e.g., from an external source) an access-enabling code. The access-enabling code can be transmitted to the client device or a remote server (e.g., a server hosting access management system 285) for evaluation and/or can be locally evaluated. The evaluation can include, for example, confirming that the access-enabling code has a particular characteristic or format (e.g., generally or one characteristic corresponding to a particular resource or type of access), matches one in an access-enabling code data store and/or has not been previously redeemed. A result of the evaluation can be locally displayed at an evaluating device, can control a device component (e.g., a physical access control module), and/or can be transmitted to another device, such as mobile device 210.

In some instances, user 205 can use multiple mobile devices 210 to perform various operations (e.g., using one device to request an access right and another to interact with client devices). Some instances of mobile device 210, access management system 285, intermediate system 250, client agent device 270, client register 260 and/or client point device 265 can include a portable electronic device (e.g., a smart phone, tablet, laptop computer or smart wearable device) or a non-portable electronic device (e.g., one or more desktop computers, servers and/or processors).

In exemplary embodiments, access rights can be represented in data maintained at a client device or at access management system 285. For example, a database or data store include a list of identifiers for each user or user device having an assigned access right for a resource or associating an identifier for each user or user device with an identifier of a particular access right. In some instances, indicia can be transmitted to a user device that indicates that an access right is availed. In various instances, it may be permitted or prohibited for the indicia to be transferred. The indicia may be provided as part of an electronic or physical object (e.g., a right to access an event) or independently. The indicia may include an access-enabling code.

In some instances, access management system 285 communicates with one or more intermediate systems 250, each of which may be controlled by a different entity as compared to an entity controlling access management system 285. For example, access management system 285 may assign access rights to intermediate systems 250 (e.g., upon acceptance of terms). Intermediate system 250 can then collect data pertaining to the assigned access rights and/or a corresponding event, can format and/or edit the data, generate a notification of availability of the access rights that includes the formatted and/or edited data and facilitate presentation of the notification at a mobile device 210. When intermediate system 250 receives a communication from the mobile device 210 indicative of an access-right request, intermediate system 250 can facilitate assignment (or reassignment) of an access right to the user (e.g., by transmitting relevant information to access management system 285 identifying the user and/or user device and/or by transmitting relevant information to mobile device 210 pertaining to the access right).

A resource can include one managed or provided by a client, such as a performing entity or an entity operating a venue. A mobile device 210 can transmit data corresponding to the access right (e.g., an access-enabling code) to a client device upon, for example, detecting the client device, detecting that a location of the mobile device 210 is within a prescribed geographical region, or detecting particular input. The receiving client device may include, for example, a client agent device 270 operated at an entrance of a defined geographical location or a client register 260 that includes or is attached to a locking turnstile. The client device can then analyze the code to confirm its validity and applicability for a particular resource and/or access type, and admittance to the event can be accordingly permitted. For example, a turnstile may change from a locked to an unlocked mode upon confirmation of the code's validity and applicability.

Each of the depicted devices and/or systems may include a software agent or application ("app") that, when executed, performs one or more actions as described herein. In some instances, a software agent or app on one device is, at least in part, complementary to a software agent or app on another device (e.g., such that a software agent or app on mobile device 210 is, at least in part, complementary to at least part of one on access management system 285 and/or a client device; and/or such that a software agent or app on intermediate system 250 is, at least in part, complementary to at least part of one on access management system 285).

In some instances, a network in the one or more networks 255 can include an open network, such as the Internet, personal area network, local area network (LAN), campus area network (CAN), metropolitan area network (MAN), wide area network (WAN), wireless local area network (WLAN), a private network, such as an intranet, extranet, or other backbone. In some instances, a network in the one or more networks 255 includes a short-range communication channel, such as Bluetooth or Bluetooth Low Energy channel. Communicating using a short-range communication such as BLE channel can provide advantages such as consuming less power, being able to communicate across moderate distances, being able to detect levels of proximity, achieving high-level security based on encryption and short ranges, and not requiring pairing for inter-device communications.

In one embodiment, communications between two or more systems and/or devices can be achieved by a secure communications protocol, such as secure sockets layer (SSL), transport layer security (TLS). In addition, data and/or transactional details may be encrypted based on any convenient, known, or to be developed manner, such as, but not limited to, DES, Triple DES, RSA, Blowfish, Advanced Encryption Standard (AES), CAST-128, CAST-256, Decorrelated Fast Cipher (DFC), Tiny Encryption Algorithm (TEA), eXtended TEA (XTEA), Corrected Block TEA (XX-TEA), and/or RC5, etc.

It will be appreciated that, while a variety of devices and systems are shown in FIG. 1, in some instances, resource management system 100 can include fewer devices and/or systems. Further, some systems and/or devices can be combined. For example, a client agent device 270 may also serve as an access management system 285 or intermediate system 250 so as to as to facilitate assignment of access rights.

As described in further detail herein, an interaction between mobile device 210 and a client device (e.g., client agent device 270, client register 260 or client point device 265) can facilitate, for example, verification that user 205 has a valid and applicable access right, obtaining an assignment of an access right, and/or obtaining an assignment of an upgraded access right.

In addition, mobile device 210-2, which is operated by user 225-2, may include a user device that is located at a stadium or concert hall during an event. Mobile device 210-2 may directly interact with a client device (e.g., client agent device 270, client register 260 or client point device 265), which is also located at the stadium or concert hall during the event. As such, the access management system 285 may be updated or accessed by mobile device 210-2 via the client agent device 270. For example, mobile device 210-2 may communicate with the client agent device 270 over a short-range communication channel 290, such as Bluetooth or Bluetooth Low Energy channel, Near Field Communication (NFC), Wi-Fi, RFID, Zigbee, ANT, etc. Communicating using a short-range communication such as BLE channel can provide advantages such as consuming less power, being able to communicate across moderate distances, being able to detect levels of proximity, achieving high-level security based on encryption and short ranges, and not requiring pairing for inter-device communications. After the short-range communication link 290 is established, mobile device 210-2 may communicate with the access management system 285 and access the item or items of resources. That is, while mobile device B is configured to communicate over network 255, mobile device 210-2 may communicate with the access management system 285 via the client agent device 270, instead of the network 255.

It will be appreciated that various parts of system 200 can be geographically separated. It will further be appreciated that system 200 can include a different number of various components rather than a number depicted in FIG. 2. For example, two or more of access assignment systems 285; one or more site systems 280; and intermediate system 250 may be located in different geographic locations (e.g., different cities, states or countries).

Figure 3:
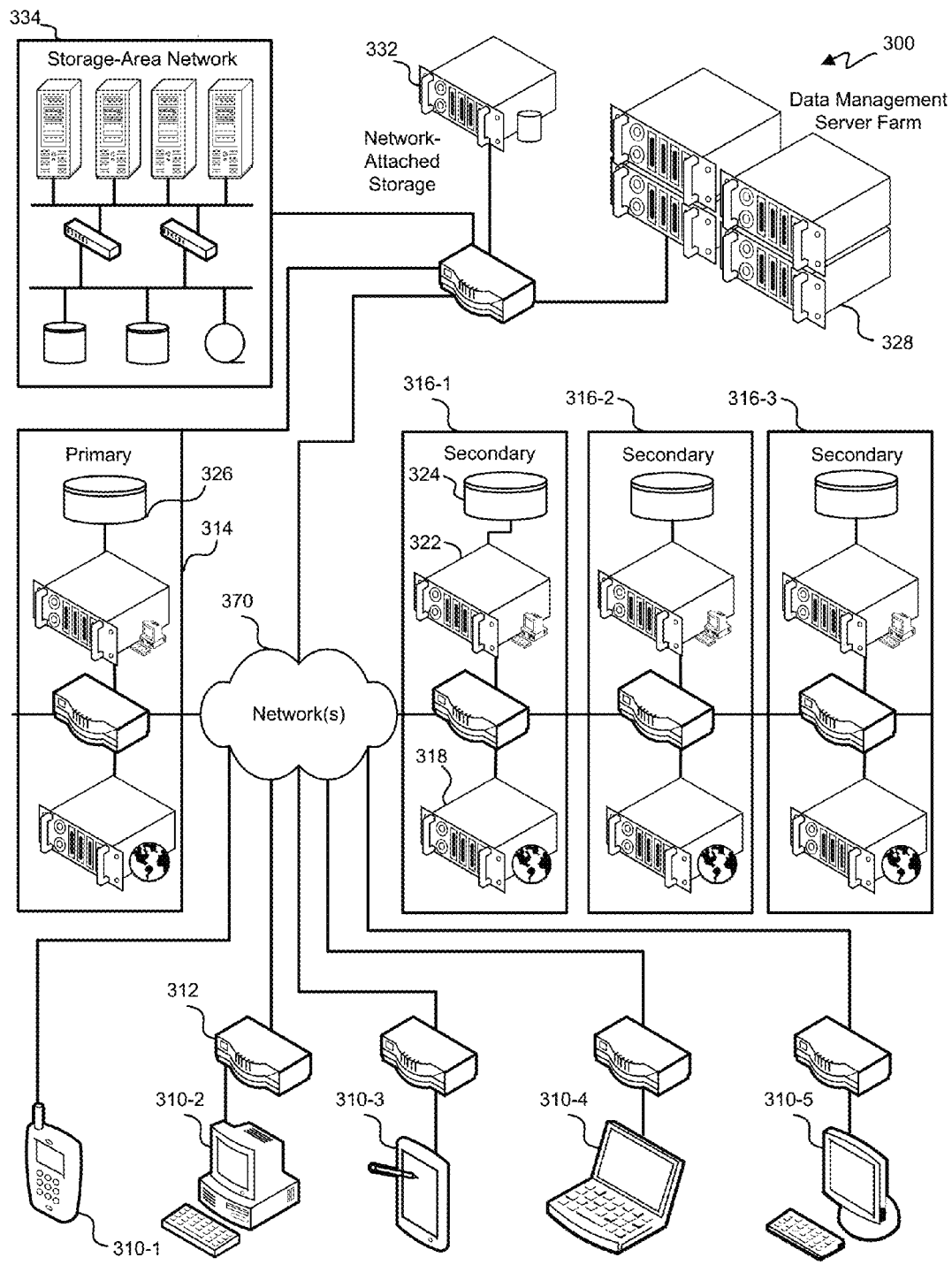
FIG. 3 shows an illustration of hardware and network connections of a resource access-facilitating interaction system according to an embodiment of the invention.

FIG. 3 shows an illustration of hardware and network connections of a resource access-facilitating interaction system 300 according to an embodiment of the invention. Each of various user devices 310-1, 310-2, 310-3, 310-4 and 310-5 can connect, via one or more inter-network connection components (e.g., a router 312) and one or more networks 370 to a primary assignment management system 314 or a secondary assignment management system 316-1, 316-2 or 316-3.

Primary assignment management system 314 can be configured to coordinate and/or control initial assignment of access rights. Secondary assignment management system 316 can be configured to coordinate and/or control reassignment and/or transfer of access rights (e.g., from one user or user device to another or from an intermediate agent to a user or user device). Such transfer may occur as a result of a sale or fee payment. Secondary assignment management system 316 may also manage transfer offers (e.g., to allow a first user to identify a price at which a transfer request would be granted and to detect if a valid request is received). It will be appreciated that, although primary assignment management system 314 is shown to be separate from each secondary assignment management system 316, in some instances, an assignment management system may relate to both a primary and secondary channel, and a single data store or a localized cluster of data stores may include data from both channels.

Each of primary access assignment system 314 and secondary access assignment system 316 can include a web server 318 that processes and responds to HTTP requests. Web server 318 can retrieve and deliver web-page data to a user device 310 that, for example, identify a resource, identify a characteristic of each of one or more access rights for the resource, include an invitation to request assignment of an access right, facilitate establishment or updating of an account, and/or identify characteristics of one or more assigned access rights. Web server 318 can be configured to support server-side scripting and/or receive data from user devices 310, such as data from forms or file uploads.

In some instances, a web server 318 can be configured to communicate data about a resource and an indication that access rights for the resource are available. Web server 318 can receive a request communication from a user device 310 that corresponds to a request for information about access rights. The request can include one or more constraints, which can correspond to (for example) values (e.g., to be matched or to define a range) of particular fields.

A management server 322 can interact with web server 318 to provide indications as to which access rights' are available for assignment, characteristics of access rights and/or what data is needed to assign an access right. When requisite information is received (e.g., about a user and/or user device, identifying a final request for one or more access rights, including payment information, and so on), management server 322 can coordinate an assignment of the one or more access rights. The coordination can include updating an access-right data store to change a status of the one or more access rights (e.g., to assigned); to associate each of the one or more access rights with a user and/or user device; to generate or identify one or more access-enabling codes for the one or more access rights; and/or to facilitate transmission reflecting the assignment (e.g., and including the one or more access-enabling codes) to a user device.

Management server 322 can query, update and manage an access-right data store to identify access rights' availability and/or characteristic and/or to reflect a new assignment. The data store can include one associated with the particular assignment system. In some instances, the data store includes incomplete data about access rights for a resource. For example, a data store 324 at and/or used by a secondary access assignment system 316 may include data about an incomplete subset of access rights that have been allocated for a particular resource. To illustrate, a client agent may have indicated that an independent intermediary system can (exclusively or non-exclusively) coordinate assignment of a portion of access rights for a resource but not the remainder. A data store 324 may then, for example, selectively include information (e.g., characteristics, statuses and/or assignment associations) for access rights in the portion.

Data store 324 or 326 associated with a particular primary or secondary access assignment system can include assignment data for a set of access rights that are configured to be set by the particular primary or secondary access assignment system or by another system. For example, a rule can indicate that a given access right is to have an available status until a first of a plurality of access assignment systems assigns the access right. Accordingly, access assignment systems would then need to communicate to alert each other of assignments.

In one instance, management server 322 (or another server in an access assignment system) sends a communication to a central data management server farm 328 reflecting one or more recent assignments. The communication may include an identification of one or more access rights, an indication that the access right(s) have been assigned, an identification of a user and/or user device associated with the assignment and/or one or more access-enabling codes generated or identified to be associated with the assignment. The communication can be sent, for example, upon assigning the access right(s), as a precursor to assigning the access right(s) (e.g., to confirm availability and/or request assignment authorization), at defined times or time intervals and/or in response to an assignment-update request received from data management server farm 328.

Data management server farm 328 can then update a central data store to reflect the data from the communication. The central data store can be part of, for example, a network-attached storage 332 and/or a storage-area network 334.

In some instances, a data store 324 or 326 can include a cache, that includes data stored based on previous communications with data management server farm 328. For example, data management server farm 328 may periodically transmit statuses of a set of access rights (e.g., those initially configured to be assignable by an access assignment system) or an updated status (e.g., indicating an assignment) of one or more access rights. As another example, data management server farm 328 may transmit statuses upon receiving a request from an access assignment system for statuses and/or authorization to assign one or more access rights.

An access assignment system may receive statuses less frequently or at times unaligned with requests received from user devices requesting information about access rights and/or assignments. Rather than initiate a central data store query responsive to each user-device request, a management server 322 can rely on cached data (e.g., locally cached data) to identify availability of one or more access rights, as reflect in webpage data and/or communications responsive to request communications for access-right information. After requisite information has been obtained, management server 322 can then communicate with data management server farm 328 to ensure that one or more particular access rights have remained available for assignment.

In some instances, one or more of primary access assignment system 314 and/or a secondary access assignment system 314 need not include a local or system-inclusive data store for tracking access-right statuses, assignments and/or characteristics. Instead, the access assignment system may communicate with a remote and/or central data store (e.g., network-attached storage 332 or storage-area network 334).

Access management system 285 can include a primary access assignment system 314 and/or a secondary access assignment system 314; data management server farm 328;

and/or a central data store (e.g., network-attached storage 332 or storage-area network 334). Each of one or more intermediate systems 250 can include a primary access assignment system 314 and/or a secondary access assignment system 314.

Data management server farm 328 may periodically and/or routinely assess a connection with an access assignment system 314. For example, a test communication can be sent that is indicative of a request to respond (e.g., with particular data or generally). If a response communication is not received, if a response communication is not received within a defined time period and/or if a response communication includes particular data (e.g., reflecting poor data integrity, network speed, processing speed, etc.), data management server farm 328 may reconfigure access rights and/or permissions and/or may transmit another communication indicating that assignment rights of the access assignment system are limited (e.g., to prevent the system from assigning access rights).

It will be appreciated that various parts of system 300 can be geographically separated. For example, two or more of primary access assignment system 314; one or more of secondary access assignment systems 314; and data management server farm 328 may be located in different geographic locations (e.g., different cities, states or countries).

It will further be appreciated that system 300 can include a different number of various components rather than a number depicted in FIG. 3. For example, system 300 can include multiple data management server farms 328, central data stores and/or primary access assignment systems 314 (e.g., which can be geographically separated, such as being located in different cities, states or countries). In some instances, processing may be split (e.g., according to a load-balancing technique) across multiple data management server farms 328 and/or across multiple access assignment systems 314. Meanwhile, the farms and/or systems can be configured to accept an increased or full load should another farm and/or system be unavailable (e.g., due to maintenance). Data stored in a central data store may also be replicated in geographically separated data stores.

Figure 4:
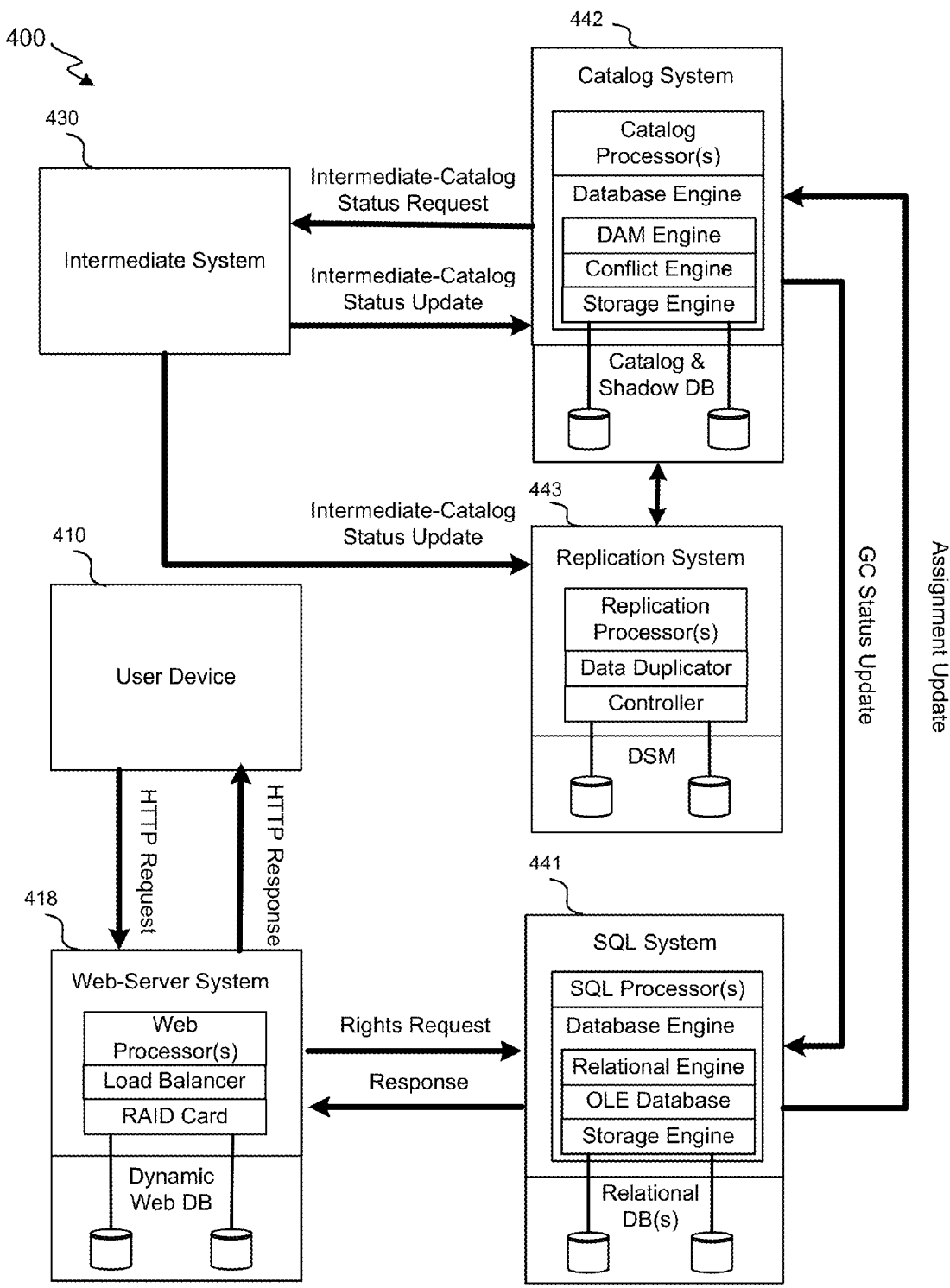
FIG. 4 shows an illustration of a communication exchange between components involved in a resource access-facilitating interaction system according to an embodiment of the invention.

FIG. 4 shows an illustration of a communication exchange between components involved in a resource access-facilitating interaction system 400 according to an embodiment of the invention. A user device 410 can send one or more HTTP requests to a web-server system 418, and web-server system 418 can respond with one or more HTTP responses that include webpage data. User device 410, in some embodiments, can be a mobile device similar to mobile devices 110 and 210 from FIGS. 1 and 2 respectively. The webpage data can include, for example, information about one or more resources, characteristics of a set of access rights for each of the one or more resources, availability of one or more access rights, an invitation to request an assignment of one or more access rights and/or indications as to what information is required for an access-right assignment. HTTP requests can include assignment-request data (e.g., a resource identification, requisite information, and/or an identification of an access-right constraint or access right).

Web-server system 418 can include one or more web processors (e.g., included in one or more server farms, which may be geographically separated) to, for example, map a path component of a URL to web data (e.g., stored in a local file system or generated by a program);

retrieve the web data; and/or generate a response communication including the web data. Web processor can further parse communication to identify input-corresponding data in HTTP requests, such as field values required for an access-right assignment.

Web-server system 418 can also include a load balancer to distribute processing tasks across multiple web processors. For example, HTTP requests can be distributed to different web processors. Load-balancing techniques can be configured so as, for example, to distribute processing across servers or server farms, decrease a number of hops between a web server and user device, decrease a geographical location between a user device and web server, etc.

Web-server system 418 can further include a RAID component, such as a RAID controller or card. A RAID component can be configured, for example, to stripe data across multiple drives, distribute parity across drives and/or mirror data across multiple drives. The RAID component can be configured to improve reliability and increase request-processing speeds.

Web-server system 418 can include one or more distributed, non-distributed, virtual, non-virtual, local and/or remote data stores. The data stores can include web data, scripts and/or content object (e.g., to be presented as part or web data).

Some HTTP requests include requests for identifications of access-right characteristics and/or availability. To provide web data reflecting such information, web-server system 418 can request the information from another server, such as an SQL system 441 (e.g., which may include one or more servers or one or more server farms).

SQL system 441 can include one or more SQL processors (e.g., included in one or more server farms, which may be geographically separated). SQL processors can be configured to query, update and otherwise use one or more relational data stores. SQL processors can be configured to execute (and, in some instances, generate) code (e.g., SQL code) to query a relational data store.

SQL system 441 can include a database engine, that includes a relational engine, OLE database and storage engine. A relational engine can process, parse, compile, and/or optimize a query and/or make query-associated calls. The relational engine can identify an OLE DB row set that identifies the row with columns matching search criteria and/or a ranking value. A storage engine can manage data access and use the rowset (e.g., to access tables and indices) to retrieve query-responsive data from one or more relational databases.

SQL system 441 can include one or more distributed, non-distributed, virtual, non-virtual, local and/or remote relational data stores. The relational databases can include linked data structures identifying, for example, resource information, access-right identifications and characteristics, access-right statuses and/or assignments, and/or user and/or user account data. Thus, for example, use of the relational structures may facilitate identifying, for a particular user, a characteristic of an assigned access right and information about a resource associated with the access right.

One or more data structures in a relational data structure may reflect whether particular access rights have been assigned or remain available. This data may be based on data received from a catalog system 442 that monitors and tracks statuses of resource access rights. Catalog system 442 can include one or more catalog processors (e.g., included in one or more server farms, which may be geographically separated). Catalog processors can be configured to generate status-update request communications to be sent to one or more access assignment systems and/or intermediate systems and/or to receive status-update communications from one or more access assignment systems and/or intermediate systems. A status-update communication can, for example, identify an access right and/or resource and indicate an assignment of the access right. For example, a status-update communication can indicate that a particular access right has been assigned and is thus no longer available. In some instances, a status-update communication identifies assignment details, such as a user, account and/or user device associated with an access-right assignment; a time that the assignment was made; and/or a price associated with the assignment.

In some instances, a status update is less explicit. For example, a communication may identify an access right and/or resource and request a final authorization of an assignment of the access right. Catalog system 442 can then verify that the access right is available for assignment (e.g., and that a request-associated system or entity is authorized to coordinate the assignment) and can transmit an affirmative response. Such a communication exchange can indicate (in some instances) that the access right is assigned and unavailable for other assignment.

In some instances, catalog system 442 can also be integrated with a non-intermediate access assignment system, such that it can directly detect assignments. For example, an integrated access assignment system can coordinate a message exchange with a user device, can query a catalog data store to identify available access rights and can facilitate or trigger a status-change of an access right to reflect an assignment (e.g., upon having received all required information.

Whether a result of a direct assignment detection or a status update from an intermediate system, a database engine of catalog system 442 can manage one or more data stores so as to indicate a current status of each of a set of access rights for a resource. The one or more data stores may further identify any assignment constraints. For example, particular access rights may be earmarked so as to only allow one or more particular intermediate systems to trigger a change to the access rights' status and/or to assign the access rights.

The database engine can include a digital asset management (DAM) engine to receive, transform (e.g., annotate, reformat, introduce a schema, etc.) status-update communications, and identify other data (e.g., an identifier of an assigning system and/or a time at which a communication was received) to associate with a status update (e.g., an assignment). Therefore, the DAM engine can be configured to prepare storage-update tasks so as to cause a maintained data store to reflect a recent data change.

Further, the DAM engine can facilitate handling of datastore queries. For example, a status-request communication or authorization-request communication can be processed to identify variables and/or indices to use to query a data store. A query can then be generated and/or directed to a data store based on the processing. The DAM engine can relay (e.g., and, potentially, perform intermediate processing to) a query result to a request-associate system.

The database engine can also include a conflict engine, which can be configured to access and implement rules indicating how conflicts are to be handled. For example, catalog system 442 may receive multiple requests within a time period requesting an assignment authorization (or a hold) for a particular access right. A rule may indicate that a first request is to receive priority, that a request associated with a more highly prioritized requesting system (e.g., intermediate system) is to be prioritized, that a request associated with a relatively high (or low) quantity of access rights identified in the request for potential assignment are to be prioritized, etc.

The database engine can further include a storage engine configured to manage data access and/or data updates (e.g., modifying existing data or adding new data). The data managed by and/or accessible to the storage engine can be included in one or more data stores. The data stores can include, for example, distributed, non-distributed, virtual, non-virtual, local and/or remote data stores. The data stores can include, for example, a relational, non-relational, object, non-object, document and/or non-document data store. Part or all of a data store can include a shadow data store that shadows data from another data store. Part or all of a data store can include an authoritative data store that is (e.g., directly and/or immediately) updated with access-right assignment changes (e.g., such that a primary or secondary access assignment system updates the data store as part of an access-right assignment process, rather than sending a post-hoc status-update communication reflecting the assignment). In some instances, a data store an authoritative data store identifies a status for each of a set (e.g., or all) of access rights for a given resource. Should there be any inconsistency between an authoritative data store and another data store (e.g., at an intermediate system), system 400 can be configured such that the authoritative data store is controlling.

System 400 can further include a replication system 443. Replication system 443 can include one or more replication processors configured to identify new or modified data, to identify one or more data stores and/or location at which to store the new or modified data and/or to coordinate replication of the data. In some instances, one or more of these identifications and/or coordination can be performed using a replication rule. For example, a replication rule may indicate that replication is to be performed in a manner biased towards storing replicated data at a data store geographically separated from another data store storing the data.

A data duplicator can be configured to read stored data and generate one or more write commands so as to store the data at a different data store. A controller can manage transmitting write commands appropriately so as to facilitate storing replicated data at identified data stores. Further, a controller can manage data stores, such as a distributed memory or distributed shared memory, to ensure that a currently active set of data stores includes a target number of replications of data.

Accordingly, web-server system 418 can interact with user device 410 to identify available access rights and to collect information needed to assign an access right. Web-server system 418 can interact with SQL system 441 so as to retrieve data about particular resources and/or access rights so as to configure web data (e.g., via dynamic web-pages or scripts) to reflect accurate or semi-accurate information and/or statuses. SQL system 441 can use relational data stores to quickly provide such data. Meanwhile, catalog system 442 may manage one or more non-relational and/or more comprehensive data stores may be tasked with more reliably and quickly tracking access-right statuses and assignments. The tracking may include receiving status updates (e.g., via a push or pull protocol) from one or more intermediate systems and/or by detecting assignment updates from non-intermediate systems, such as an integrated access assignment system and/or SQL system 441. Catalog system 442 may provide condensed status updates (e.g., reflecting a binary indication as to whether an access right is available) to SQL system 441 periodically, at triggered times and/or in response to a request from the SQL system. A replication system 443 can further ensure that data is replicated at multiple data stores, so as to improve a reliability and speed of system 400.

It will be appreciated that various parts of system 400 can be geographically separated. For example, each of user device 410, intermediate system 430, web-server system 418, SQL system 441, catalog system 442 and replication 443 may be located in different geographic locations (e.g., different cities, states or countries).

Figure 5:
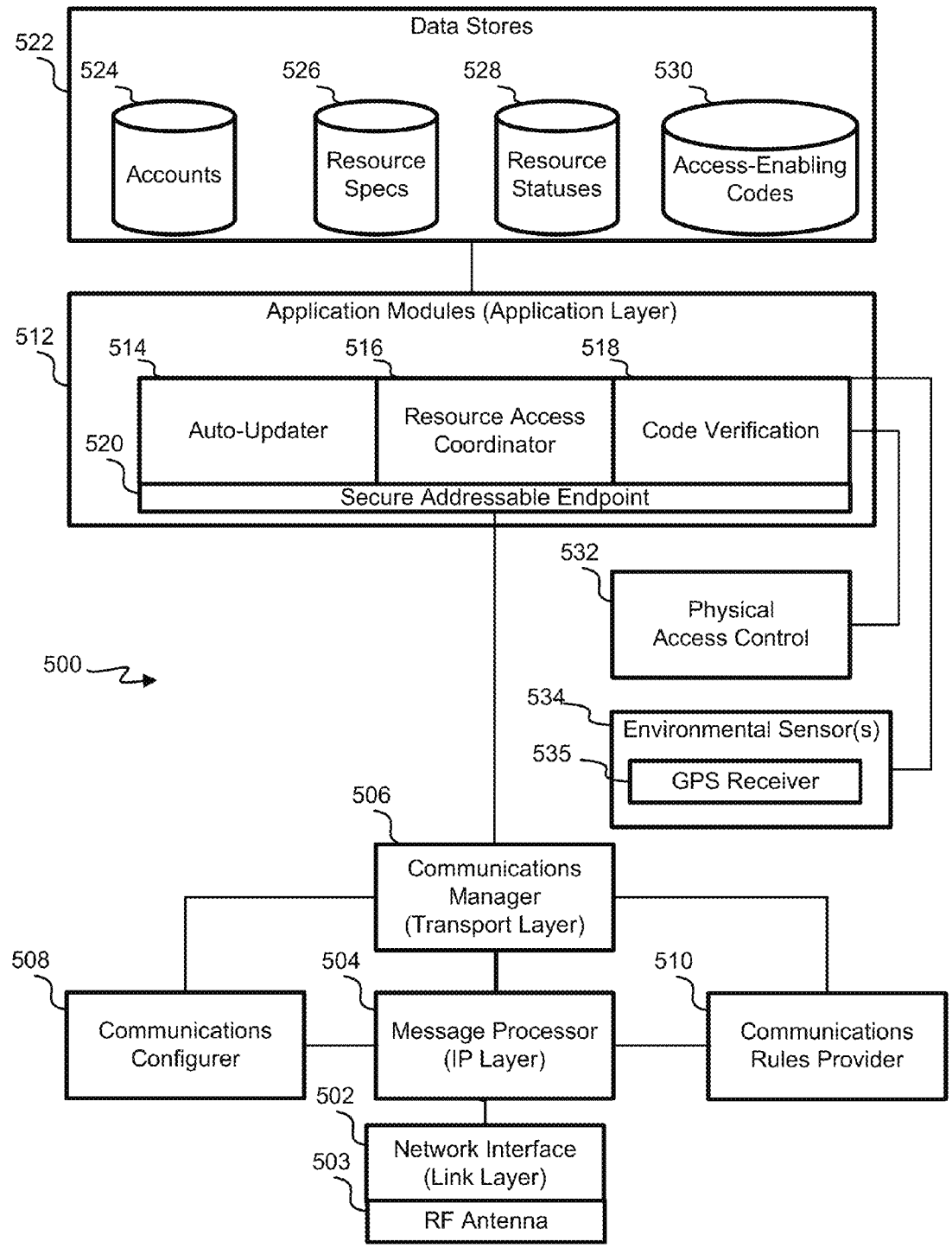
FIG. 5 illustrates example components of a device.

FIG. 5 illustrates example components of a device 500, such as a client device (e.g., client agent device 270, client register 260 and/or client point device 265), an intermediate system (e.g., intermediate system(s) 250) and/or an access management system (e.g., access management system 285) according to an embodiment of the invention.

The components can include one or more modules that can be installed on device 500. Modules can include some or all of the following: a network interface module 502 (which can operate in a link layer of a protocol stack), a message processor module 504 (which can operate in an IP layer of a protocol stack), a communications manager module 506 (which can operate in a transport layer of a protocol stack), a communications configure module 508 (which can operate in a transport and/or IP layer in a protocol stack), a communications rules provider module 510 (which can operate in a transport and/or IP layer in a protocol stack), application modules 512 (which can operate in an application layer of a protocol stack), a physical access control module 532 and one or more environmental sensors 534.

Network interface module 502 receives and transmits messages via one or more hardware components that provide a link-layer interconnect. The hardware component(s) can include, for example, RF antenna 503 or a port (e.g., Ethernet port) and supporting circuitry. In some embodiments, network interface module 502 can be configured to support wireless communication, e.g., using Wi Fi (IEEE 802.11 family standards), Bluetooth® (a family of standards promulgated by Bluetooth SIG, Inc.), BLE, or near-field communication (implementing the ISO/IEC 18092 standards or the like).

RF antenna 503 can be configured to convert electric signals into radio and/or magnetic signals (e.g., to radio waves) to transmit to another device and/or to receive radio and/or magnetic signals and convert them to electric signals. RF antenna 503 can be tuned to operate within a particular frequency band. In some instances, a device includes multiple antennas, and the antennas can be, for example, physically separated. In some instances, antennas differ with respect to radiation patterns, polarizations, take-off angle gain and/or tuning bands. RF interface module 502 can include one or more phase shifters, filters, attenuators, amplifiers, switches and/or other components to demodulate received signals, coordinate signal transmission and/or facilitate high-quality signal transmission and receipt.

In some instances, network interface module 502 includes a virtual network interface, so as to enable the device to utilize an intermediate device for signal transmission or reception. For example, network interface module 502 can include VPN software.

Network interface module 502 and one or more antennas 503 can be configured to transmit and receive signals over one or more connection types. For example, network interface module 502 and one or more antennas 503 can be configured to transmit and receive WiFi signals, cellular signals, Bluetooth signals, Bluetooth Low Energy (BLE) signals, Zigbee signals, or Near-Field Communication (NFC) signals.

Message processor module 504 can coordinate communication with other electronic devices or systems, such as one or more servers or a user device. In one instance, message processor module 504 is able to communicate using a plurality of protocols (e.g., any known, future and/or convenient protocol such as, but not limited to, XML, SMS, MMS, and/or email, etc.). Message processor module 504 may further optionally serialize incoming and/or outgoing messages and facilitate queuing of incoming and outgoing message traffic.

Message processor module 504 can perform functions of an IP layer in a network protocol stack. For example, in some instances, message processor module 504 can format data packets or segments, combine data packet fragments, fragment data packets and/or identify destination applications and/or device addresses. For example, message processor module 504 can defragment and analyze an incoming message to determine whether it is to be forwarded to another device and, if so, can address and fragment the message before sending it to the network interface module 502 to be transmitted. As another example, message processor module 504 can defragment and analyze an incoming message to identify a destination application that is to receive the message and can then direct the message (e.g., via a transport layer) to the application.

Communications manager module 506 can implement transport-layer functions. For example, communications manager module 506 can identify a transport protocol for an outgoing message (e.g., transmission control protocol (TCP) or user diagram protocol (UDP)) and appropriately encapsulate the message into transport protocol data units. Message processor module 504 can initiate establishment of connections between devices, monitor transmissions failures, control data transmission rates and monitoring transmission quality. As another example, communications manager module 506 can read a header of an incoming message to identify an application layer protocol to receive the message's data. The data can be separated from the header and sent to the appropriate application. Message processor module 504 can also monitor the quality of incoming messages and/or detect out of order incoming packets.

In some instances, characteristics of message-receipt or message-transmission quality can be used to identify a health status of an established communications link. In some instances, communications manager module 506 can be configured to detect signals indicating the health status of an established communications link (e.g., a periodic signal from the other device system, which if received without dropouts, indicates a healthy link).

In some instances, a communication configurer module 508 is provided to track attributes of another system so as to facilitate establishment of a communication session. In one embodiment, communication configurer module 508 further ensures that inter-device communications are conducted in accordance with the identified communication attributes and/or rules. Communication configurer module 508 can maintain an updated record of the communication attributes of one or more devices or systems. In one embodiment, communications configurer module 508 ensures that communications manager module 206 can deliver the payload provided by message processor module 504 to the destination (e.g., by ensuring that the correct protocol corresponding to the client system is used).

A communications rules provider module 510 can implement one or more communication rules that relate to details of signal transmissions or receipt. For example, a rule may specify or constrain a protocol to be used, a transmission time, a type of link or connection to be used, a destination device, and/or a number of destination devices. A rule may be generally applicable or conditionally applicable (e.g., only applying for messages corresponding to a particular app, during a particular time of day, while a device is in a particular geographical region, when a usage of a local device resource exceeds a threshold, etc.). For example, a rule can identify a technique for selecting between a set of potential destination devices based on attributes of the set of potential destination devices as tracked by communication configure module 316. To illustrate, a device having a short response latency may be selected as a destination device. As another example, communications rules provider 510 can maintain associations between various devices or systems and resources. Thus, messages corresponding to particular resources can be selectively transmitted to destinations having access to such resources.

A variety of application modules 512 can be configured to initiate message transmission, process incoming transmissions, facilitate selective granting of resource access, facilitate processing of requests for resource access, and/or performing other functions. In the instance depicted in FIG. 5, application modules 512 include an auto-updater module 514, a resource access coordinator module 516, and/or a code verification module 518.

Auto-updater module 514 automatically updates stored data and/or agent software based on recent changes to resource utilization, availability or schedules and/or updates to software or protocols. Such updates can be pushed from another device (e.g., upon detecting a change in a resource availability or access permit) or can be received in response to a request sent by device 500. For example, device 500 can transmit a signal to another device that identifies a particular resource, and a responsive signal can identify availabilities of access to the resource (e.g., available seat reservations for a sporting event or concert). As another example, device 500 can transmit a signal that includes an access access-enabling code, and a responsive signal can indicate whether the code is applicable for access of a particular resource and/or is valid.

In some instances, auto-updater module 514 is configured to enable the agent software to understand new, messages, commands, and/or protocols, based on a system configuration/change initiated on another device. Auto-updater module 514 may also install new or updated software to provide support and/or enhancements, based on a system configuration change detected on device 500. System configuration changes that would necessitate changes to the agent software can include, but are not limited to, a software/hardware upgrade, a security upgrade, a router configuration change, a change in security settings, etc. For example, if auto-updater module 514 determines that a communication link with another device has been lost for a pre-determined amount of time, auto-updater module 514 can obtain system configuration information to help re-establish the communication link. Such information may include new settings/configurations on one or more hardware devices or new or upgraded software on or connected to device 500. Thus, auto-updater module 514 can detect or be informed by other software when there is a new version of agent software with additional functionality and/or deficiency/bug corrections or when there is a change with respect to the software, hardware, communications channel, etc.), and perform updates accordingly.

Based on the newly obtained system configuration for device 500, auto-updater module 514 can cause a new communication link to be re-established with another device. In one embodiment, upon establishment of the communication link, system configuration information about device 500 can also be provided to another device to facilitate the connection to or downloading of software to device 500.

In one embodiment, when a poor health signal is detected by another device (e.g., when the health signal is only sporadically received but the communication link is not necessarily lost), the other device can send a command to auto-updater module 514 to instruct auto-updater module 514 to obtain system configuration information about device 500. The updated system configuration information may be used in an attempt to revive the unhealthy communications link (e.g., by resending a resource request). For example, code can utilize appropriate system calls for the operating system to fix or reestablish communications. By way of example and not limitation, model and driver information is optionally obtained for routers in the system in order querying them. By way of further example, if the code determines that a new brand of router has been installed, it can adapt to that change, or to the change in network configuration, or other changes.

Instead or in addition, the host server (e.g., via communications manager 506) can send specific instructions to auto-updater module 514 to specify tests or checks to be performed on device 500 to determine the changes to the system configurations (e.g., by automatically performing or requesting an inventory check of system hardware and/or software). For example, the components involved in the chain of hops through a network can be queried and analyzed. Thus, for example, if a new ISP (Internet service provider) is being used and the management system traffic is being filtered, or a new router was installed and the software needs to change its configuration, or if someone made a change to the operating system that affects port the management system is using to communicate, the management system (or operator) can communicate with the ISP, change it back, or choose from a new available port, respectively.

The specific tests may be necessary to help establish the communication link, if, for example, the automatic tests fail to provide sufficient information for the communication link to be re-established, if additional information is needed about a particular configuration change, and/or if the client system is not initially supported by the auto-updater module 514, etc.

Auto-updater module 514 can also receive signals identifying updates pertaining to current or future availability of resources and/or access permits. Based on the signals, auto-updater module 514 can modify, add to or delete stored data pertaining to resource availabilities, resource schedules and/or valid access permits. For example, upon receiving an update signal, auto-updater 514 can modify data stored in one or more data stores 522, such as an account data store 524, resource specification data store 526, resource status data store 528 and/or access-enabling code data store 530.

Account data store 524 can store data for entities, such as administrators, intermediate-system agents and/or users. The account data can include login information (e.g., username and password), identifying information (e.g., name, residential address, phone number, email address, age and/or gender), professional information (e.g., occupation, affiliation and/or professional position), preferences (e.g., regarding event types, performers, seating areas, and/or resource types), purchase data (e.g., reflecting dates, prices and/or items of past purchases) and/or payment data (e.g., credit card number and expiration date or payment account information). The account data can also or alternatively include technical data, such a particular entity can be associated with one or more device types, IP addresses, browser identifier and/or operating system identifier).

Resource specification data store 526 can store specification data characterizing each of one or more resources. For example, specification data for a resource can include a processing power, available memory, operating system, compatibility, device type, processor usage, power status, device model, number of processor cores, types of memories, date and time of availability, a performing entity, a venue of the event and/or a set of seats (e.g., a chart or list). Specification data can further identify, for example, a cost for each of one or more access rights.

Resource status data store 528 can store status data reflecting which resources are available (or unavailable), thereby indicating which resources have one or more open assignments. In some instances, the status data can include schedule information about when a resource is available. Status data can include information identifying an entity who requested, reserved or was assigned a resource. In some instances, status information can indicate that a resource is being held or reserved and may identify an entity associated with the hold or reserve and/or a time at which the hold or reservation will be released.

Access-enabling code data store 530 can store access-enabling code data that includes one or more codes and/or other information that can be used to indicate that an entity is authorized to use, have or receive a resource. An access-enabling code can include, for example, a numeric string, an alphanumeric string, a text string, a 1-dimensional code, a 2-dimensional code, a barcode, a quick response (QR) code, an image, a static code and/or a temporally dynamic code. An access-enabling code can be, for example, unique across all instances, resource types and/or entities. For example, access-enabling codes provided in association for tickets to a particular event can be unique relative to each other. In some instances, at least part of a code identifies a resource or specification of a resource. For example, for a ticket to a concert, various portions of a code may reflect: a performing entity, resource location, date, section and access-permitted location identifier.

One or more of data stores 524, 526, 528, and 530 can be a relational data store, such that elements in one data store can be referenced within another data store. For example, resource status data store 528 can associate an identifier of a particular ticket with an identifier of a particular entity. Additional information about the entity can then be retrieved by looking up the entity identifier in account data store 524.

Updates to data stores 524, 526, 528, and 530 facilitated and/or initiated by auto-updater module 514 can improve cross-device data consistency. Resource access coordinator module 516 can coordinate resource access by, for example, generating and distributing identifications of resource availabilities; processing requests for resource access; handling competing requests for resource access; and/or receiving and responding to resource-offering objectives.

Figure 6:
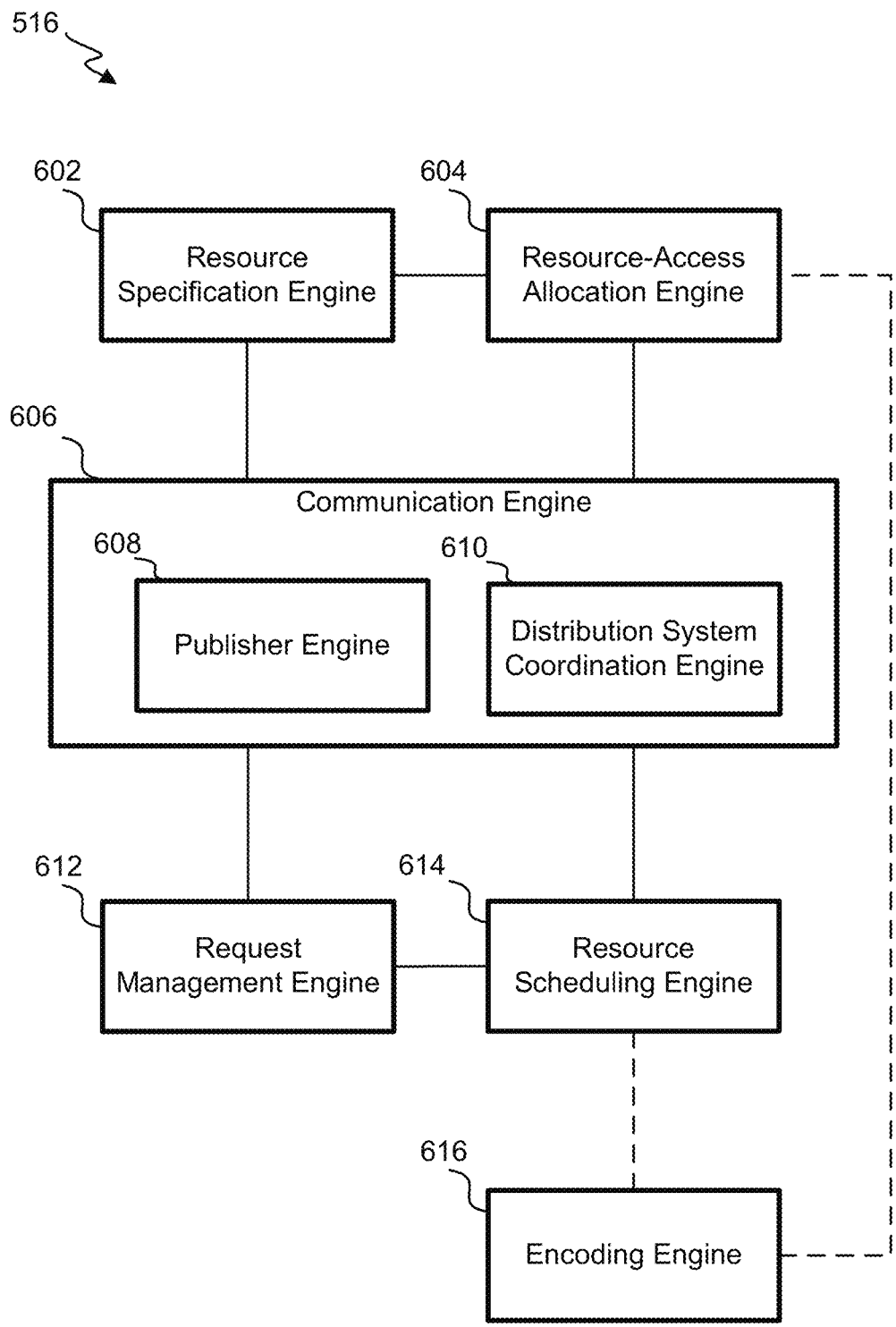
FIG. 6 illustrates example components of resource access coordinator module.

FIG. 6 illustrates example components of resource access coordinator module 516 that may operate, at least in part, at an access management system (e.g., access management system) according to an embodiment of the invention. A resource specification engine 602 can identify one or more available resources. For example, resource specification engine 602 can detect input that identifies a current or future availability of a new resource.

Resource specification engine 602 can identify one or more specifications of each of one or more resources. A specification can include an availability time period. For example, resource specification engine 602 can determine that a resource is available, for example, at a particular date and time (e.g., as identified based on input), for a time period (e.g., a start to end time), as identified in the input, and/or from a time of initial identification until another input indicating that the resource is unavailable is detected. A specification can also or alternatively include a location (e.g., a geographic location and/or venue) of the resource. A specification can also or alternatively include one or more parties associated with the resource (e.g., performing acts or teams). Resource specification engine 602 can store the specifications in association with an identifier of the resource in resource specifications data store 526.

A resource-access allocation engine 604 can allocate access rights for individual resources. An access right can serve to provide an associated entity with the right or a priority to access a resource. Because (for example) association of an access right with an entity can, in some instances, be conditioned on fee payment or authorization thereof, an allocated access right can be initially unassociated with particular entities (e.g., users). For example, an allocated right can correspond to one or more access characteristics, such as an processor identifier, a usage time, a memory allocation, a geographic location (e.g., section or seat identifier), and/or a fee. For an allocated access right, resource-access allocation engine 604 can store an identifier of the right in resource statuses data store 528 in association with an identifier for the resource and an indication that it has not yet been assigned to a particular entity.

A communication engine 606 can facilitate communicating the availability of the resource access rights to users. In some instances, a publisher engine 608 generates a presentation that identifies a resource and indicates that access rights are available. Initially or in response to user interaction with the presentation, the presentation can identify access characteristics about available access rights. The presentation can include, for example, a chart that identifies available access rights for an event and corresponding fees. Publisher engine 608 can distribute the presentation via, for example, a website, app page, email and/or message. The presentation can be further configured to enable a user to request assignments of one or more access rights.

In some instances, an intermediate system coordination engine 610 can facilitate transmission of information about resource availability (e.g., resource specifications and characteristics of resource-access rights) to one or more intermediate systems (e.g., by generating one or more messages that include such information and/or facilitating publishing such information via a website or app page). Each of the one or more intermediate systems can publish information about the resource and accept requests for resource access. In some instances, intermediate system coordination engine 610 identifies different access rights as being available to individual intermediate systems to coordinate assignment. For example, access rights for seats in Section 1 may be provided for a first intermediate system to assign, and access rights for seats in Section 2 may be provided to a second intermediate system to assign.

In some instances, overlapping access rights are made available to multiple intermediate systems to coordinate assignments. For example, some or all of a first set of resource rights (e.g., corresponding to a section) may be provided to first and second intermediate systems. In such instances, intermediate system coordination engine 610 can respond to a communication from a first intermediate system indicating that a request has been received (e.g., and processed) for an access right in the set) by sending a notification to one or more other intermediate systems that indicates that the access right is to be at least temporarily (or entirely) made unavailable.

Intermediate system coordination engine 610 can monitor communication channels with intermediate systems to track the health and security of the channel. For example, a healthy connection can be inferred when scheduled signals are consistently received. Further, intermediate system coordination engine 610 can track configurations of intermediate systems (e.g., via communications generated at the intermediate systems via a software agent that identifies such configurations) so as to influence code generation, communication format, and/or provisions or access rights.

Thus, either via a presentation facilitated by publisher engine 608 (e.g., via a web site or app page) or via communication with an intermediate system, a request for assignment of an access right can be received. A request management engine 612 can process the request. Processing the request can include determining whether all other required information has been received, such as user-identifying information (e.g., name), access-right identifying information (e.g., identifying a resource and/or access-right characteristic) user contact information (e.g., address, phone number, and/or email address), and/or user device information (e.g., type of device, device identifier, and/or IP address).

When all required information has not been received, request management engine 612 can facilitate collection of the information (e.g., via a webpage, app page or communication to an intermediate system). Request management engine 612 can also or alternatively collect payment information, determine that payment information has been received, obtain authorization of payment, determine that payment has been authorized (e.g., via an intermediate system), collect payment, and/or determine that payment has been collected. For example, publisher engine 608 may receive a credit card number and expiration date via a webpage, and request management engine 612 can request authorization for an amount of the requested access rights. In some instances, payment assessments are performed subsequent to at least temporary assignments of access rights. In some instances, request management engine 612 retrieves data from a user account. For example, publisher engine 608 may indicate that a request for an access right has been received while a user was logged into a particular account. Request management engine 612 may then retrieve, for example, contact information, device information, and/or preferences and/or payment information associated with the account from account data store 324.

In some instances, request management engine 612 prioritizes requests, such as requests for overlapping, similar or same access rights (e.g., requests for access rights associated with a same section) received within a defined time period. The prioritization can be based on, for example, times at which requests were received (e.g., prioritizing earlier requests), a request parameter (e.g., prioritizing requests for a higher or lower number of access rights above others), whether requests were received via an intermediate system (e.g., prioritizing such requests lower than others), intermediate systems associated with requests (e.g., based on rankings of the systems), whether requests were associated with users having established accounts, and/or whether requests were associated with inputs indicative of a bot initiating the request (e.g., shorter inter-click intervals, failed CAPTCHA tests, purchase history departing from a human profile).

Upon determining that required information has been received and request-processing conditions have been met, request management engine 612 can forward appropriate request information to a resource scheduling engine 614. For a request, resource scheduling engine 614 can query resource status data store 528 to identify access rights matching parameters of the request.

In some instances, the request has an access-right specificity matching a specificity at which access rights are assigned. In some instances, the request is less specific, and resource scheduling engine 614 can then facilitate an identification of particular rights to assign. For example, request management engine 612 can facilitate a communication exchange by which access right characteristics matching the request are identified, and a user is allowed to select particular rights. As another example, request management engine 612 can itself select from amongst matching access rights based on a defined criterion (e.g., best summed or averaged access-right ranking, pseudo-random selection, or a selection technique identified based on user input).

Upon identifying appropriately specific access rights, resource scheduling engine 614 can update resource status data store 528 so as to place the access right(s) on hold (e.g., while obtaining payment authorization and/or user confirmation) and/or to change a status of the access right(s) to indicate that they have been assigned (e.g., immediately, upon receiving payment authorization or upon receiving user confirmation). Such assignment indication may associate information about the user (e.g., user name, device information, phone number and/or email address) and/or assignment process (e.g., identifier of any intermediate system and/or assignment date and time) with an identifier of the access right(s).

For individual assigned access rights, an encoding engine 616 can generate an access-enabling code. The access-enabling code can include, for example, an alphanumeric string, a text string, a number, a graphic, a barcode (e.g., a 1-dimensional or 2-dimensional barcode), a static code, a dynamic code (e.g., with a feature depending on a current time, current location or communication) and/or a technique for generating the code (e.g., whereby part of the code may be static and part of the code may be determined using the technique). The code may be unique across all access rights, all access rights for a given resource, all access rights associated with a given location, all access rights associated with a given time period, all resources and/or all users. In some instances, at least part of the code is determined based on or is thereafter associated with an identifier of a user, user device information, a resource specification and/or an access right characteristic.

In various embodiments, the code may be generated prior to allocating access rights (e.g., such that each of some or all allocated access rights are associated with an access-enabling code), prior to or while assigning one or more access right(s) responsive to a request (e.g., such that each of some or all assigned access rights are associated with an access-enabling code), at a prescribed time, and/or when the device is at a defined location and/or in response to user input. The code may be stored at or availed to a user device. In various instances, at the user device, an access-enabling code may be provided in a manner such that it is visibly available for user inspection or concealed from a user. For example, a ticket document with a barcode may be transmitted to a user device, or an app on the user device can transmit a request with a device identifier for a dynamic code.

Encoding engine 616 can store the access-enabling codes in access-enabling code data store 530. Encoding engine 616 can also or alternatively store an indication in account data store 524 that the access right(s) have been assigned to the user. It will again be appreciated that data stores 524, 526, 528, and 530 can be relational and/or linked, such that, for example, an identification of an assignment can be used to identify one or more access rights, associated access-enabling code(s) and/or resource specifications.

Resource scheduling engine 614 can facilitate one or more transmissions of data pertaining to one or more assigned access rights to a device of a user associated with the assignment. The data can include an indication that access rights have been assigned and/or details as to which rights have been assigned. The data can also or alternatively include access-enabling codes associated with assigned access rights.

While FIG. 6 depicts components of resource access coordinator module 616 that may be present on an access management system 285, it will be appreciated that similar or complementary engines may be present on other systems. For example, a communication engine on a user device can be configured to display presentations identifying access right availability, and a request management engine on a user device can be configured to translate inputs into access-right requests to send to an intermediate system or access management system.

Returning to FIG. 5, code verification module 518 (e.g., at a user device or client device) can analyze data to determine whether an access-enabling code is generally valid and/or valid for a particular circumstance. The access-enabling code can include one that is received at or detected by mobile device 210. The analysis can include, for example, determining whether all or part of the access-enabling code matches one stored in access-enabling code data store 530 or part thereof, whether the access-enabling code has previously been applied, whether all or part of the access-enabling code is consistent with itself or other information (e.g., one or more particular resource specifications, a current time and/or a detected location) as determined based on a consistency analysis and/or whether all or part of the access-enabling code has an acceptable format.

For example, access-enabling code data store 530 can be organized in a manner such that access-enabling codes for a particular resource, date, resource group, client, etc. can be queried to determine whether any such access-enabling codes correspond to (e.g., match) one being evaluated, which may indicate that the code is verified. Additional information associated with the code may also or alternatively be evaluated. For example, the additional information can indicate whether the code is currently valid or expired (e.g., due to a previous use of the code).

As another example, a portion of an access-enabling code can include an identifier of a user device or user account, and code verification module 518 can determine whether the code-identified device or account matches that detected as part of the evaluation. To illustrate, device 200 can be a client device that electronically receives a communication with an access-enabling code from a user device. The communication can further include a device identifier that identifies, for example, that the user device is a particular type of smartphone. Code verification module 518 can then determine whether device-identifying information in the code is consistent with the identified type of smartphone.

As yet another example, code verification module 518 can identify a code format rule that specifies a format that valid codes are to have. To illustrate, the code format rule may identify a number of elements that are to be included in the code or a pattern that is to be present in the code. Code verification module 518 can then determine that a code is not valid if it does not conform to the format.

Verification of an access-enabling code can indicate that access to a resource is to be granted. Conversely, determining that a code is not verified can indicate that access to a resource is to be limited or prevented. In some instances, a presentation is generated (e.g., and presented) that indicates whether access is to be granted and/or a result of a verification analysis. In some instances, access granting and/or limiting is automatically affected. For example, upon a code verification, a user device and/or user may be automatically permitted to access a particular resource. Accessing a resource may include, for example, using a computational resource, possessing an item, receiving a service, entering a geographical area, and/or attending an event (e.g., generally or at a particular location).

Verification of an access-enabling code can further trigger a modification to access-enabling code data store 530. For example, a code that has been verified can be removed from the data store or associated with a new status. This modification may limit attempts to use a same code multiple times for resource access.

A combination of modules 514, 516, 518 comprise a secure addressable endpoint agent 520 that acts as an adapter and enables cross-device interfacing in a secure and reliable fashion so as to facilitate allocation of access-enabling codes and coordinate resource access. Secure addressable endpoint agent 520 can further generate a health signal that is transmitted to another device for monitoring of a status of a communication channel. The health signal is optionally a short message of a few bytes or many bytes in length that may be transmitted on a frequent basis (e.g., every few milliseconds or seconds). A communications manager 506 on the receiving device can then monitors the health signal provided by the agent to ensure that the communication link between the host server and device 500 is still operational.

In some instances, device 500 can include (or can be in communication with) a physical access control 532. Physical access control 532 can include a gating component that can be configured to provide a physical barrier towards accessing a resource. For example, physical access control 532 can include a turnstile or a packaging lock.

Physical access control 532 can be configured such that it can switch between two modes, which differ in terms of a degree to which user access to a resource is permitted. For example, a turnstile may have a locked mode that prevents movement of an arm of the turnstile and an unlocked mode that allows the arm to be rotated. In some instances, a default mode is the mode that is more limiting in terms of access.

Physical access control 532 can switch its mode in response to receiving particular results from code verification module 518. For example, upon receiving an indication that a code has been verified, physical access control 532 can switch from a locked mode to an unlocked mode. It may remain in the changed state for a defined period of time or until an action or event is detected (e.g., rotation of an arm).

Device 500 can also include one or more environmental sensors 534. Measurements from the sensor can processed by one or more application modules. Environmental sensor(s) 534 can include a global positioning system (GPS) receiver 535 that can receive signals from one or more GPS satellites. A GPS chipset can use the signals to estimate a location of device 500 (e.g., a longitude and latitude of device 500). The estimated location can be used to identify a particular resource (e.g., one being offered at or near the location at a current or near-term time). The identification of the particular resource can be used, for example, to identify a corresponding (e.g., user-associated) access-enabling code or to evaluate an access-enabling code (e.g., to determine whether it corresponds to a resource associated with the location).

The estimated location can further or alternatively be used to determine when to perform a particular function. For example, at a user device, detecting that the device is in or has entered a particular geographical region (e.g., is within a threshold distance from a geofence perimeter or entrance gate) can cause the device to retrieve or request an access-enabling code, conduct a verification analysis of the code and/or transmit the code to a client device.

It will be appreciated that environmental sensor(s) 534 can include one or more additional or alternative sensors aside from GPS receiver 535. For example, a location of device 500 can be estimated based on signals received by another receive from different sources (e.g., base stations, client point devices or Wi Fi access points). As another example, an accelerometer and/or gyroscope can be provided. Data from these sensors can be used to infer when a user is attempting to present an access-enabling code for evaluation.

It will also be appreciated that the components and/or engines depicted in figures herein are illustrative, and a device need not include each depicted component and/or engine and/or can include one or more additional components and/or engines. For example, a device can also include a user interface, which may include a touch sensor, keyboard, display, camera and/or speakers. As another example, a device can include a power component, which can distribute power to components of the device. The power component can include a battery and/or a connection component for connecting to a power source. As yet another example, a module in the application layer can include an operating system. As still another example, an application-layer control processor module can provide message processing for messages received from another device. The message processing can include classifying the message and routing it to the appropriate module. To illustrate, the message can be classified as a request for resource access or for an access-enabling code, an update message or an indication that a code has been redeemed or verified. The message processing module can further convert a message or command into a format that can interoperate with a target module.

It will further be appreciated that the components, modules and/or agents could be implemented in one or more instances of software. The functionalities described herein need not be implemented in separate modules, for example, one or more functions can be implemented in one software instance and/or one software/hardware combination. Other combinations are similarly be contemplated.

Further yet, it will be appreciated that a storage medium (e.g., using magnetic storage media, flash memory, other semiconductor memory (e.g., DRAM, SRAM), or any other non transitory storage medium, or a combination of media, and can include volatile and/or non volatile media) can be used to store program code for each of one or more of the components, modules and/or engines depicted in FIGS. 5 and 6 and/or to store any or all data stores depicted in FIG. 5 or described with reference to FIGS. 5 and/or 6. Any device or system disclosed herein can include a processing subsystem for executing the code. The processing system can be implemented as one or more integrated circuits, e.g., one or more single-core or multi-core microprocessors or microcontrollers, examples of which are known in the art.

Figure 7:
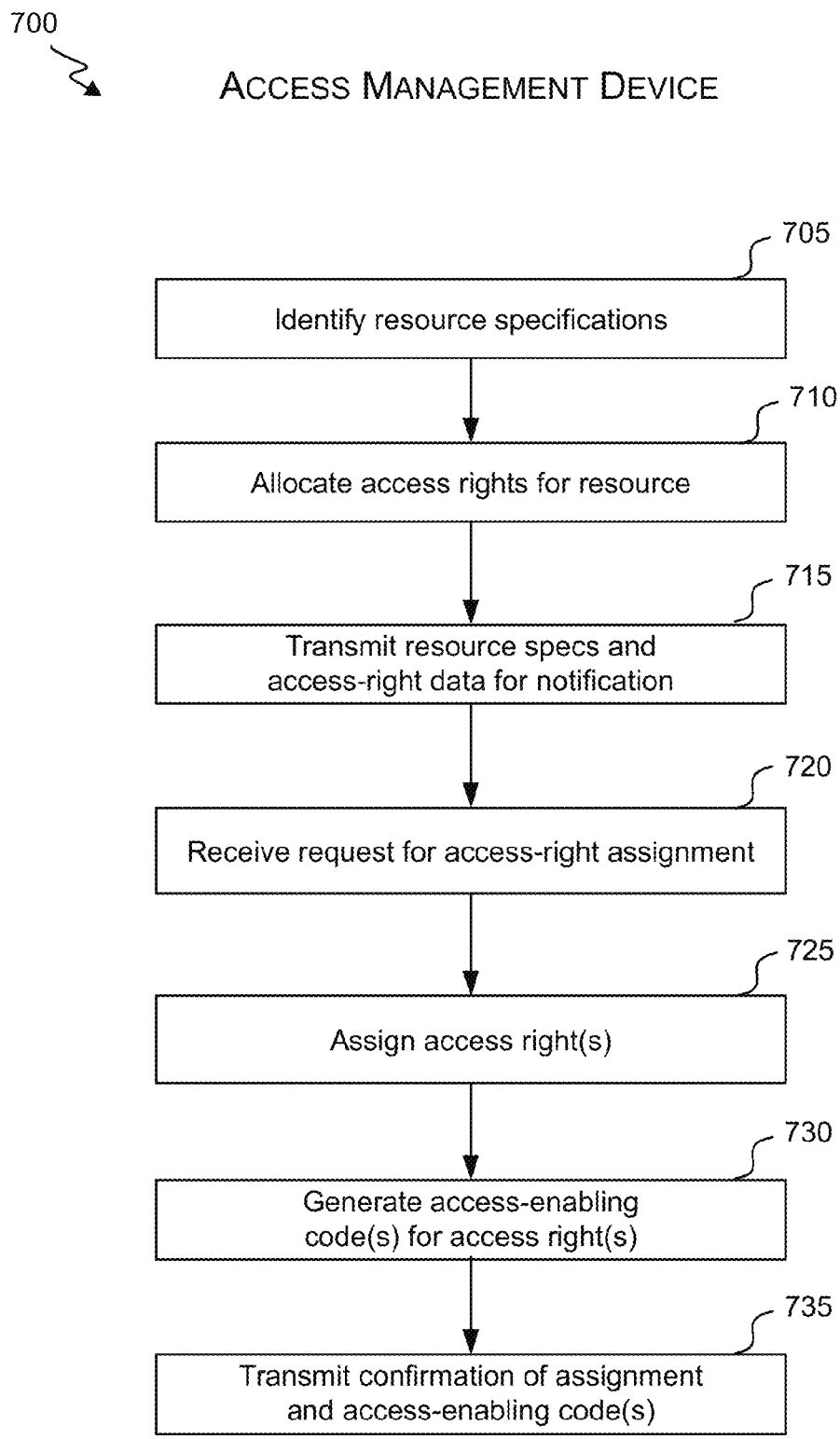
FIG. 7 illustrates a flowchart of an embodiment of a process for assigning access rights for resources.

FIG. 7 illustrates a flowchart of an embodiment of a process 700 for assigning access rights for resources. Process 700 can be performed by an access management system, such as access management system 285. Process 700 begins at block 705 where resource specification engine 302 identifies one or more specifications for a resource. The specifications can include, for example, a time at which the resource is to be available, a location of the resource, a capacity of the resources and/or one or more entities (e.g., performing entities) associated with the resource.

At block 710, resource-access allocation engine 604 allocates a set of access rights for the resource. In some instances, each of at least some of the access rights corresponds to a different access parameter, such as a different location (e.g., seat) assignment. Upon allocation, each of some or all of the access rights may have a status as available. A subset of the set of access rights can be immediately (or at a defined time) assigned or reserved according to a base assignment or reservation rule (e.g., assigning particular access rights to particular entities, who may be involved in or related to provision of the resource and/or who have requested or been assigned a set of related access rights.

At block 715, communication engine 606 transmits the resource specifications and data about the access rights. The transmission can occur in one or more transmissions. The transmission can be to, for example, one or more user devices and/or intermediate systems. In some instances, a notification including the specifications and access-right data is transmitted, and in some instances, a notification can be generated at a receiving device based on the specifications and access-right data. The notification can include, for example, a website that identifies a resource (via, at least in part, its specifications) and indicates that access rights for the resource are available for assignment. The notification can include an option to request assignment of one or more access rights.

At block 720, request management engine 612 receives a request for one or more access rights to be assigned to a user. The request can, for example, identify particular access rights and/or access parameters. The request can include or be accompanied by other information, such as identifying information. In some instances, the access management system can use at least some of such information to determine whether a fee for the access rights has been authorized. In some instances, the request is received via an intermediate system that has already handled such authorization.

At block 725, resource scheduling engine 614 assigns the requested one or more access rights to the user. The assignment can be conditioned on receipt of all required information, confirmation that the access right(s) have remained available for assignment, determining using data corresponding to the request that a bot-detection condition is not satisfied, fee provision and/or other defined conditions. Assignment of the access right(s) can include associating an identifier of each of the one or more rights with an identifier of a user and/or assignment and/or changing a status of the access right(s) to assigned. Assignment of the access right(s) can result in impeding or preventing other users from requesting the access right(s), being assigned the access right(s) and/or being notified that the access right(s) are available for assignment. Assignment of the access right(s) can, in some instances, trigger transmission of one or more communications to, for example, one or more intermediate systems identifying the access right(s) and indicating that they have been assigned and/or with an instruction to cease offering the access rights.

At block 730, encoding engine 616 generates an access-enabling code for each of the one or more access rights. The code can be generated, for example, as part of the assignment, as part of the allocation or subsequent to the assignment (e.g., upon detecting that a user is requesting access to the resource). Generating an access-enabling code can include applying a code-generation technique, such on one that generates a code based on a characteristic of a user, user device, current time, access right, resource, intermediate system or other variable. The access-enabling code can include a static code that will not change after it has been initially generated or a dynamic code that changes in time (e.g., such that block 730 can be repeated at various time points).

At block 735, communication engine 606 transmits a confirmation of the assignment and the access-enabling code(s) in one or more transmissions. The transmission(s) may be sent to one or more devices, such as a user device having initiated the request from block 720, a remote server or an intermediate system having relayed the request from block 720.

Figure 8A:
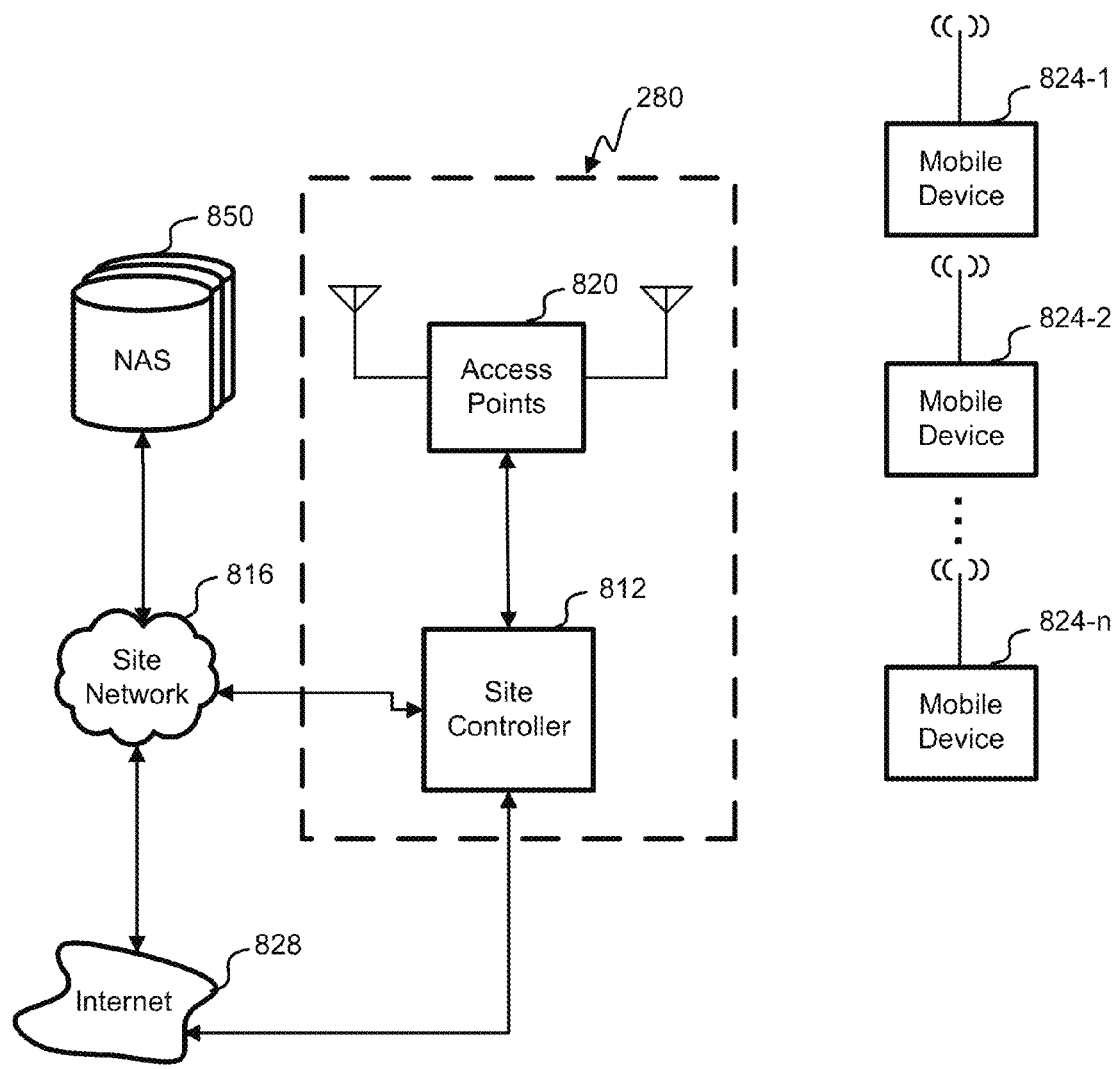
FIG. 8A shows a block diagram of a site system according to an embodiment.

Referring to FIG. 8A, an embodiment of a site system 280 is shown in relation to mobile devices 824-n, Network Attached Storage (NAS) 850, site network 816 and the Internet 828. In some embodiments, for attendees of a live event or concert, site network 816 and site system 280 provide content, services and/or interactive engagement using mobile devices 824. Connections to site system 280 and site network 816 can be established by mobile devices 824 connecting to access points 820. Mobile devices 824 can be a type of end user device 110 that is portable, e.g., smartphones, mobile phones, tablets, and/or other similar devices. Mobile devices 824 are described in further detail herein with the description of FIG. 9.

Site network 816 can have access to content (information about attendees, videos, pictures, music, trivia information, etc.) held by NAS 850. Additionally, as described herein, content can be gathered from attendees both before and during the event. By connecting to site network 816, mobile device 824 can send content for use by site system 280 or display content received from NAS 850.

Figure 8B:
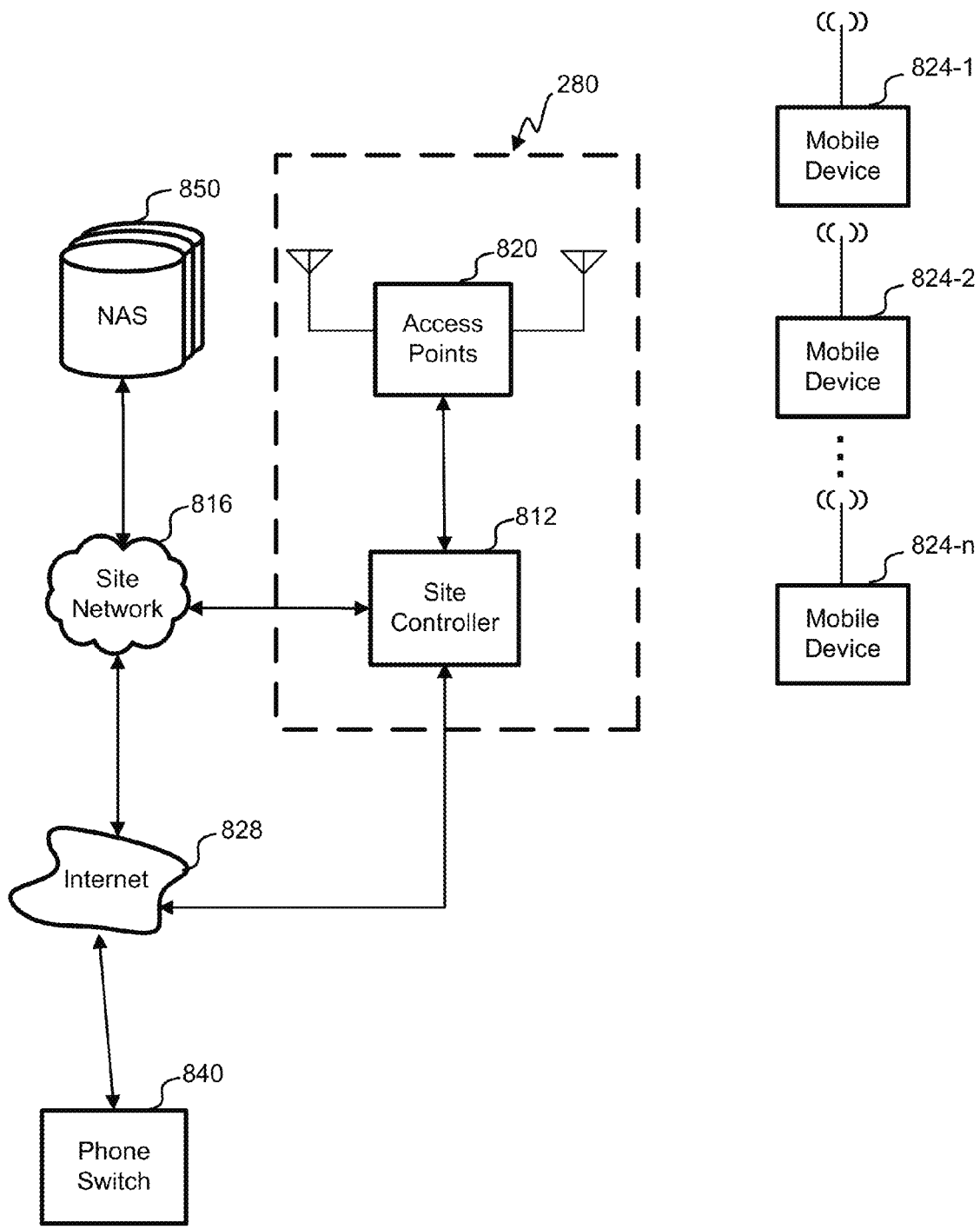
FIG. 8B shows another block diagram of a site system according to an embodiment.

Referring to FIG. 8B, another embodiment of a site system 280 is shown in relation to mobile devices 824-n, Network Attached Storage (NAS) 850, site network 816 and the Internet 828, in an embodiment. FIG. 8B additionally includes phone switch 840. In some embodiments, phone switch 840 can be a private cellular base station configured to spoof the operation of conventionally operated base stations. Using phone switch 840 at an event site allows site system 280 to provide additional types of interactions with mobile devices 824. For example, without any setup or configuration to accept communications from site controller 812, phone switch 840 can cause connected mobile devices 824 to ring and, when answered, have an audio or video call be established. When used with other embodiments described herein, phone switch 840 can provide additional interactions. For example, some embodiments described herein use different capabilities of mobile devices 824 to cause mass sounds and/or establish communications with two or more people. By causing phones to ring and by establishing cellular calls, phone switch can provide additional capabilities to these approaches.

Figure 9:
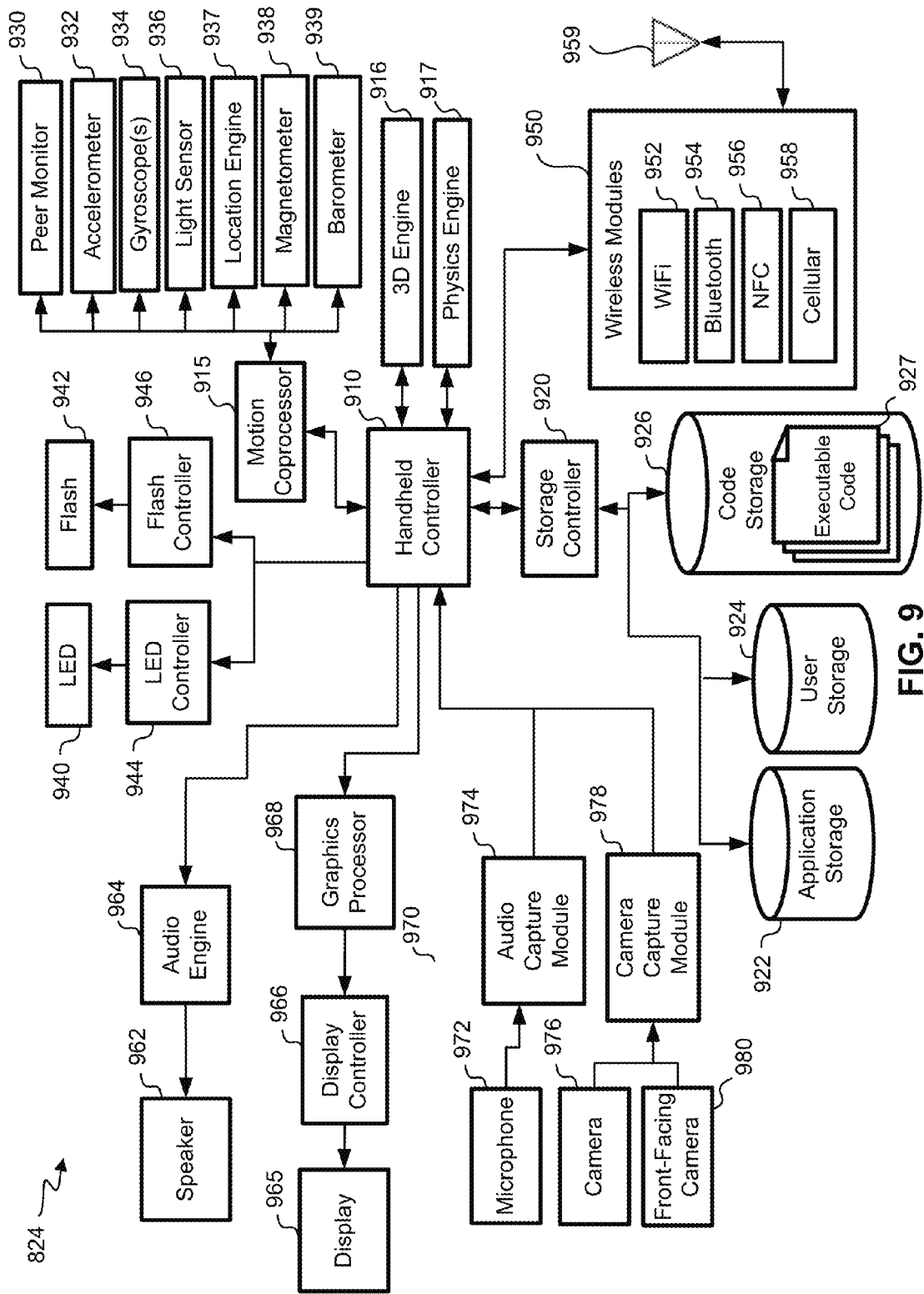
FIG. 9 shows a block diagram of a mobile device according to an embodiment.

FIG. 9 illustrates example components of a mobile device 824. Mobile device 824 can connect to access point 820 using one or more antennas 959, and wireless modules 950 (e.g., WiFi 952, Bluetooth 954, NFC 956 and/or cellular 958). Once connected to site network 816 and site controller 812, handheld controller 910 can use input and output hardware components and/or sensors to enable different embodiments described herein.

Input sensors used by mobile device 824 described herein include, accelerometer 932, gyroscope(s) 934, light sensor 936, magnetometer (e.g., compass) 938, and barometer 939. Location engine 937 can use geolocation hardware components (e.g., wireless signal receivers, iBeacon, NFC, Global Positioning System (GPS), and/or other similar components). Peer monitor 930 uses a data structure to store and updates the location of nearby mobile devices 824.

In some embodiments, peer monitor 930 receives information from site controller 812 that corresponds to the locations of other nearby mobile devices. In embodiments, peer monitor can also use sensors to locate nearby mobile devices 824 (e.g., Bluetooth 954, NFC 956, and or other similar sensing hardware). Other input components used by some embodiments include microphone 972, camera 976, and front-facing camera 980, respectively controlled and/or providing capture by audio capture module 974 and camera capture module 978. One having skill in the relevant art(s), given the description herein, will appreciate that other input and or sensor components can be used by embodiments of mobile device 824.

In some embodiments, components are included that assist with the processing and utilization of sensor data. Motion coprocessor 915, 3D engine 916, and physics engine 917 can all process sensor data, and also perform tasks graphics rendering related to graphics processor 968.

Output components used by some embodiments include speaker 962, display 966, LED 940, and flash 942, respectively controlled and/or relayed output information by, audio engine 964, graphics engine 968 and screen controller 970, LED controller 964, and flash controller 946. Other output components used by mobile devices 824 include NFC 956 and Bluetooth 954, which, beyond wireless communication capabilities can also be used to send instructions to certain devices.

Some embodiments described herein use information collected by mobile device 824 using connections to site controller 812 and/or site network 816. This information collected (e.g., pictures, video, recorded audio, movement data collected by gyroscope 934 and/or accelerometer 932, and/or other collectable data) can be stored by mobile device 824 in user storage 924. In addition, in some embodiments described herein, site controller 812 can control mobile device 824 by sending control signals to the device, and storing information in application storage 922 (e.g., content to be displayed, hardware configuration instructions, trigger commands for hardware components, and/or other similar information). In some embodiments, handheld controller 910 uses storage controller 920 to store and retrieve information from application storage 922 and user storage 924. Storage controller 920 can also retrieve executable code from code storage 926 for execution by different processor components.

One having skill in the relevant art(s), given the description herein, will appreciate that other combinations of similar components can be used to provide the features of the components described above, e.g., components described above could be replaced by components that have been combined into integrated components and/or components that have been divided into multiple components, e.g., a variation of camera 976 can include a camera capture module 978 as an integrated unit. Additional descriptions of example components used by mobile device 824 are provided below.

Figure 10:
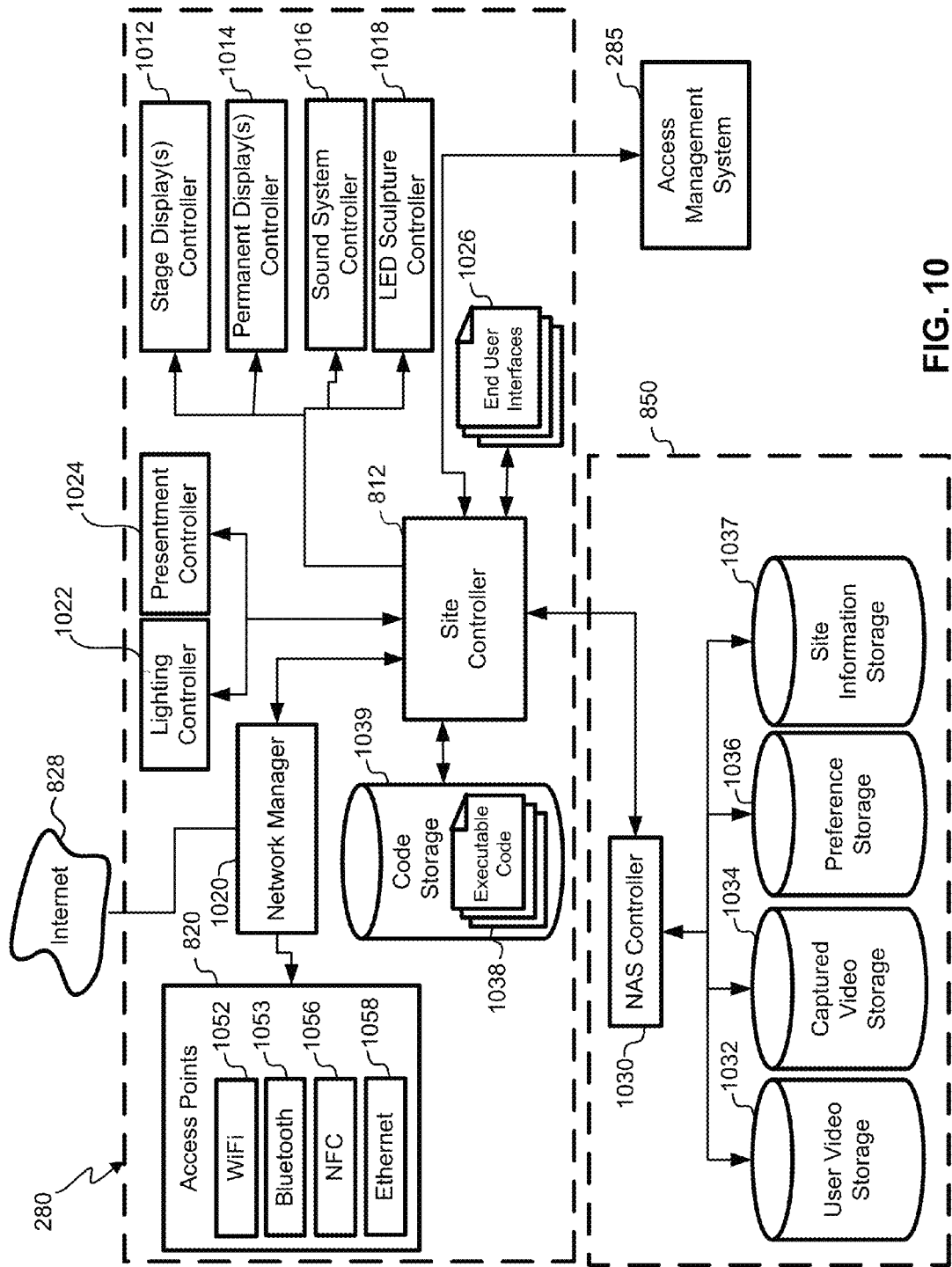
FIG. 10 shows a more detailed block diagram of a site system according to an embodiment.

FIG. 10 illustrates sample components of an embodiment of site system 280, including connections to NAS 850 and access management system 285. Embodiments of site controller 812 use network manager 1020 to connect via access points 820 (using e.g., WiFi 1052, Bluetooth 1053, NFC 1056, Ethernet 1058, and/or other network connections) to other network components, such as site network 816 and mobile devices 824. In some embodiments, site system 280 uses site controller 812 to control aspects of an event venue. A broad variety of venue features can be controlled by different embodiments, including: permanent lights (e.g., with lighting controller 1022), stage lights (e.g., with presentment controller 1024), stage display screens (e.g., with stage display(s) controller 1012), permanent display screens (e.g., with permanent display(s) controller 1014), and the venue sound system (e.g., with the sound system controller 1016). In an embodiment discussed further with the discussion of FIG. 27 below, different presentation devices (e.g., an LED sculpture) can present information from site controller 812.

A more detailed view of NAS 850 is shown, including NAS controller 1030 coupled to user video storage 1032, captured video storage 1034, preference storage 1036, and 3D model 1038. Captured video storage 1034 can receive, store and provide user videos received from mobile devices 824. In some embodiments, site controller 812 triggers the automatic capture of images, audio and video from mobile devices 824, such triggering being synchronized to activities in an event. Images captured by this and similar embodiments can be stored on both the capturing mobile device 824 and user video storage 1032. In an embodiment, site controller 812 can coordinate the transfer of information from mobile devices to NAS 850 (e.g., captured media) with activities taking place during the event. When interacting with mobile devices 824, some embodiments of site controller 812 can provide end user interfaces 1026 to enable different types of interaction. For example, as a part of engagement activities, site controller may offer quizzes and other content to the devices. Additionally, with respect to location determinations discussed herein, site controller can supplement determined estimates with voluntarily provided information using end user interfaces 1026, stored in a storage that is not shown.

In some embodiments, to guide the performance of different activities, site controller 812 and/or other components may use executable code 1038 tangibly stored in code storage 1039. In some embodiments, site information storage 1037 can provide information about the site, e.g., events, seat maps, attendee information, geographic location of destinations (e.g., concessions, bathrooms, exits, etc.), as well as 3D models of site features and structure.

Figure 11:
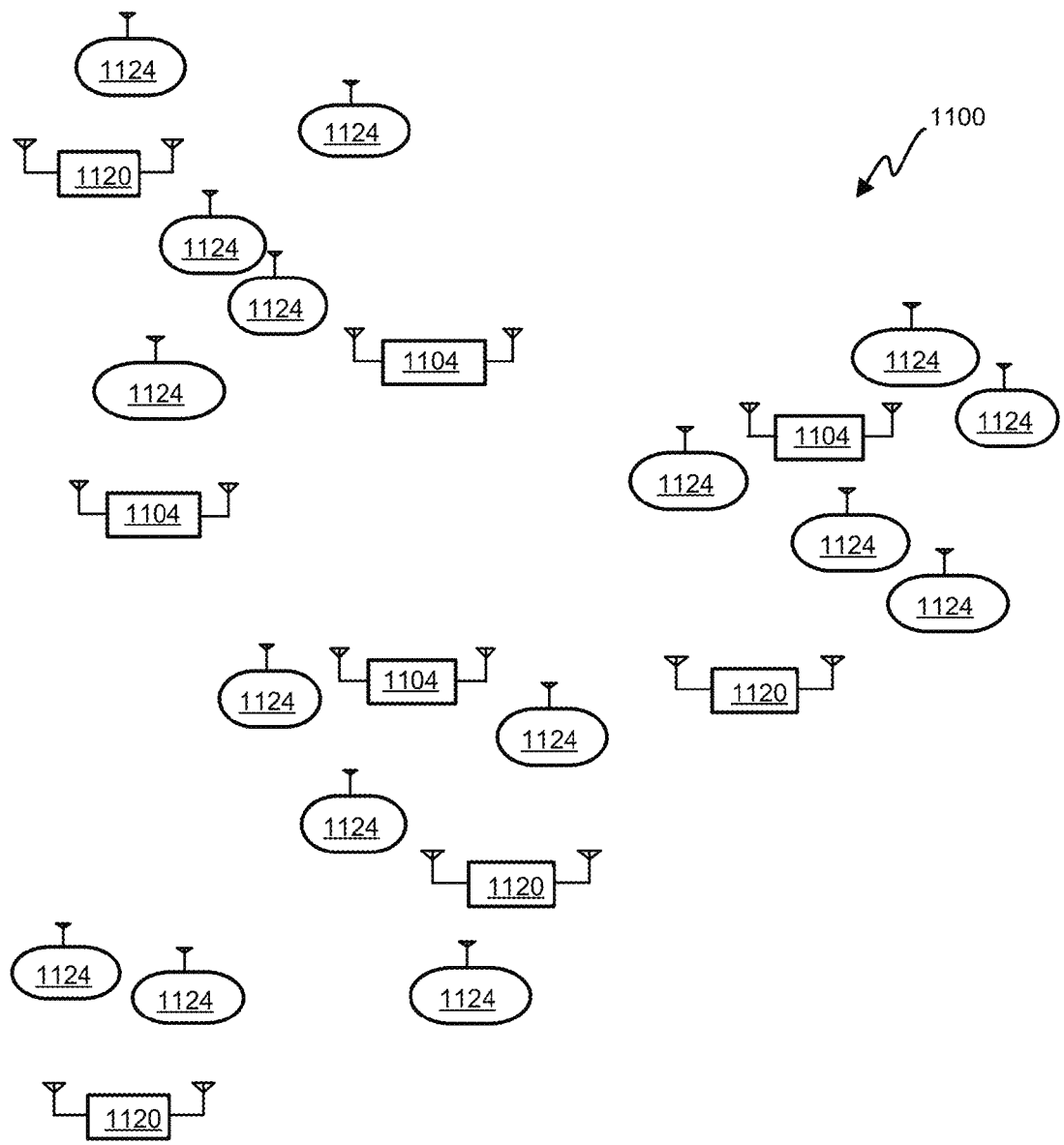
FIG. 11 shows a block diagram of a wireless topology according to an embodiment.

With reference to FIG. 11, an embodiment of a wireless topology 1100 is shown. In this example, access points 820 are divided throughout a venue with WiFi hotspots 1104. In other embodiments, Bluetooth™, cellular, WiMax™, Zigbee™, or other base stations or hotspots could be used alternatively or in combination. Mobile devices 1124 can move throughout the venue and connect to various hotspots. Location estimations used by some embodiments described herein can be performed by triangulating between multiple hotspots with known locations. Based upon which hotspots are visible, and the measured strength of respective signals, mobile devices 1124 can estimate location. Location can also be provided, or the previously described approach can be enhanced by, other geolocation approaches such as ranging, GPS and/or other mechanisms.

Figure 12:
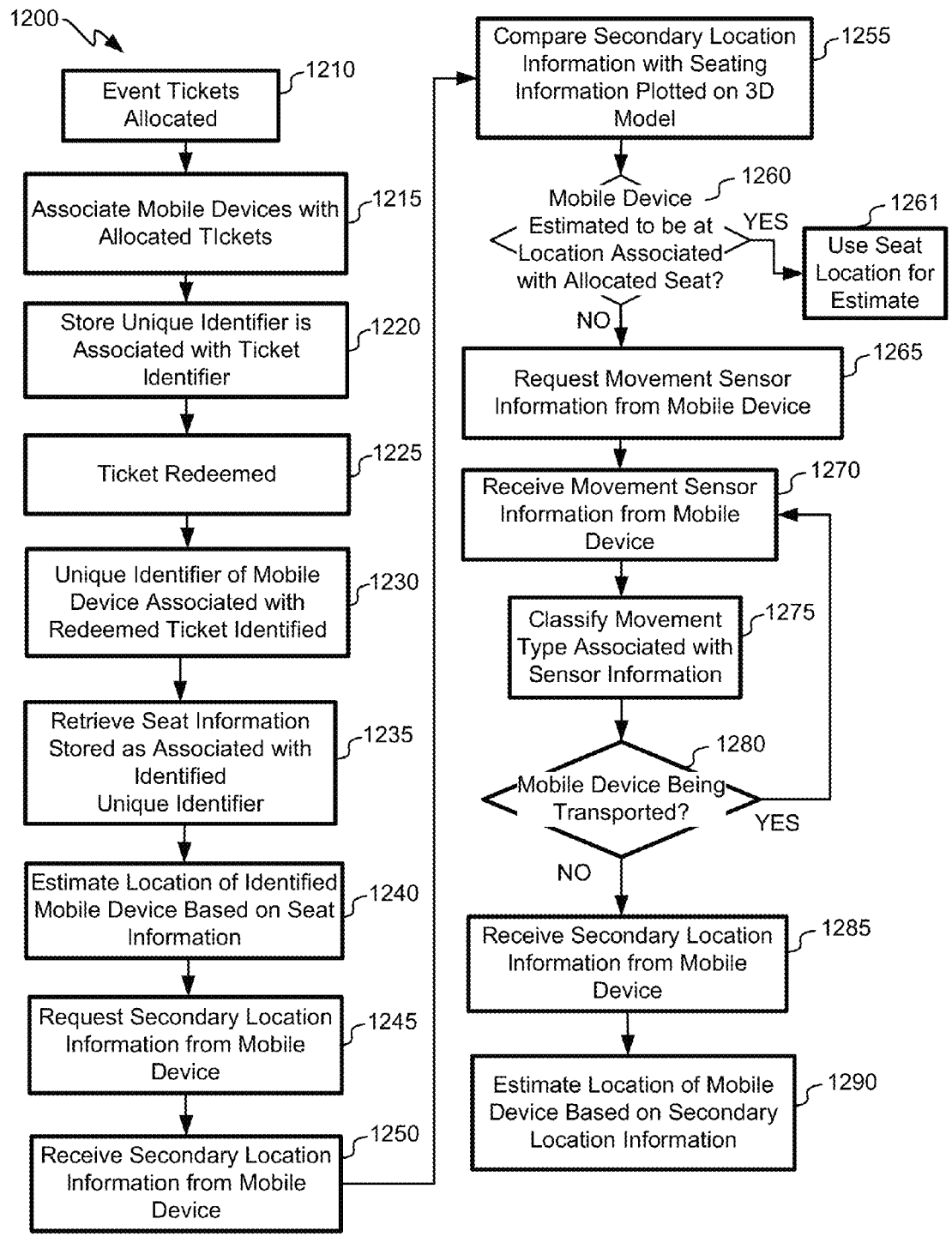
FIG. 12 illustrates a flowchart of an embodiment of a process for estimating the location of the mobile device according to an embodiment.

FIG. 12 illustrates a flowchart of an embodiment of a process 1200 for initializing contact with a mobile device 824 and estimating the location of the mobile device for use with other processes. In block 1210, event tickets are allocated. Other information that can be captured and stored at the time of ticket purchase include: one or more names of people who will be using purchased tickets, the home address of the purchaser, and/or other similar information.

In block 1220, the determined unique identifier is stored as associated with one of the allocated tickets. In some embodiments, a mobile device 824 can be used at the time of purchase of a ticket, and, because of this, a unique identifier for the mobile device 824 can be detected and stored as associated with a ticket. At block 1220, this unique Identifier is associated with an identifier from the redeemed ticket is stored.

At block 1225, at the time of an event, a ticketholder redeems the ticket to enter the event venue site. As described above with the descriptions of FIGS. 2 and 3, access management system 285 manages the issuance and redemption of tickets for some embodiments.

Once at the site, different wireless communication techniques can be used to detect any mobile devices carried to the event and connect them to the site network. For example, at the time the ticketholder redeems their ticket, their mobile device 824 can have WiFi enabled. Using access point 820 with this WiFi protocol, a network connection can be established between the mobile device 824 of a ticketholder and site network resources such as site controller 812 and site network 816. Other connections can also be used to connect to access point 820, including Bluetooth 1053 and NFC 1056.

In some embodiments, based on the connection to access point 820, a uniform identifier of mobile device 824 can be determined, and this identifier can be used to retrieve information about the ticketholder. Thus, at block 1230, a unique identifier of mobile device is associated with the ticket used by the ticketholder to gain entry to the venue. Alternatively, if mobile device 824 was used to present an e-Ticket for redemption, this uniform identifier could be determined at the time of redemption. An embodiment can automatically establish a connection between a mobile device 824 and access point 820 at the time an electronic ticket is redeemed using the mobile device.

In some embodiments, the connection established between mobile device 824 and a ticket used to enter the venue can be used to improve the geolocation capabilities of mobile device 824. Based on information associated with the redeemed ticket, stored seat information is identified and retrieved. In block 1240, the location of the mobile device is estimated based on the on seat information, e.g., location coordinates for each seat at a venue can be stored and available in the NAS 850 for use by embodiments. Having this initial location estimate can improve the geolocation process by improving the speed of initial estimates (e.g., the database retrieval of the location of a seat is generally faster than establishing GPS satellite connections).

Continuing with the geolocation (and/or indoor location) of mobile device 824, at block 1245, secondary location information is requested from the mobile device. In some embodiments, this secondary location information includes GPS data for a slower completing, but more accurate estimate. At block 1245, the secondary location information is received from mobile device 824.

In block 1255, the received secondary location information is compared with seating information for the venue. In some embodiments, this seating information can be plotted in a model (e.g., a 3D model stored in site information storage 1037 in NAS 850). Based on this comparison, at block 1260 the mobile device is present at the ticketed seating location (e.g., comparing received GPS coordinates with the 3D Model). At block 1261, when the mobile device is estimate to be in the seating position, this estimated position is stored for further use with this device.

At block 1265, when it is estimated that mobile device 824 is not at a location associated with the ticketed seat on record for the device, site controller 812 requests accelerometer, gyroscope and/or compass data. In block 1270, the movement sensor information is received, and in block 1265, site controller 812 can use this information provided by mobile device 824 to classify the movement type estimated as being performed with mobile device 824. Because embodiments described herein operate in venues for concerts, some embodiments do not automatically equate movement with locomotion. At block 1280, if, after analysis of the collected movement data indicates that mobile device is not being transported (e.g., the person holding is likely dancing, not walking at the venue). At block 1285, once it is likely that mobile device 824 is not being transported, a new location estimate is performed based on collected information, and this location estimate is used in additional processes described herein.

It should be appreciated that many of the additional location determining blocks described with FIG. 12 are optional, and some embodiments can determine location by a single approach, e.g., iBeacon, wireless geolocation, or GPS.

Figure 13:
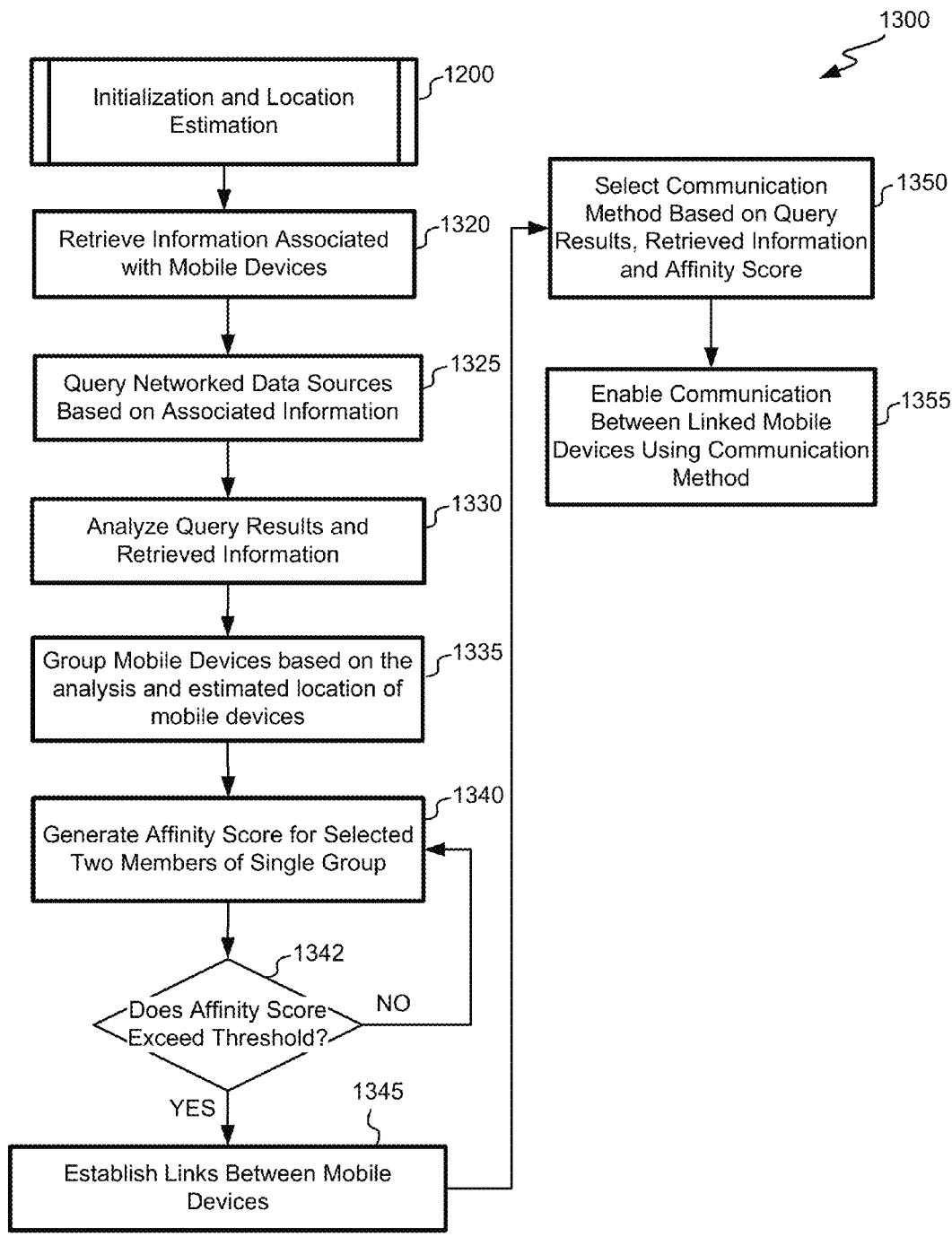
FIG. 13 illustrates a flowchart of an embodiment of a process for linking mobile devices at an event using groups based on seating and activity according to an embodiment.

FIG. 13 illustrates a flowchart of an embodiment of a process 1300 for linking mobile devices at an event using groups based on seating and activity. At block 1200, the initialization and location estimate process is performed. As is described above, in some embodiments, mobile devices 824 can be associated with people. Social networks rely upon linking people based on shared characteristics. In block 1320, information associated with mobile devices (e.g., information about the associated owners of the devices) can be retrieved from data stores maintained by server systems associated with generating and maintaining tickets (e.g., access management system 285 and site controller 812).

In block 1325, the retrieved data from the ticketing systems can be used to retrieve additional information from independent sources. For example, when a mobile device 824 is associated with a ticket, and the ticket is associated with a particular person, the name of that person can be used to search online social networks. In some embodiments, ticket purchasers provide credentials to their social networking sites with the understanding that information from these sites will be used to improve a concert experience. These credentials can be stored for use by embodiments, either in storage on mobile device 824 (e.g., application storage 622) or on servers available to site system 280 (e.g., in NAS 850 for use by site controller 812).

Searching operations can be performed by embodiments using a variety of different components. Based on access to Internet 528, NAS 850 and access management system 285 (e.g., for information about ticket purchasers), site controller 812 performs the searching, analysis for some embodiments of this section.

At block 1330, the collected results of queries performed for multiple people are analyzed and, at block 1335, mobile devices 824 are grouped based on the retrieved data. For example, a search of popular social network sites reveals that several event attendees are avid skateboarders, college professors and/or like falafel. Adding an extra dimension, to promote the formation of closer groups, some embodiments factor in the seating arrangement in the venue, with distance apart, level of seating, and/or other seating oriented factors influencing the organization of event attendees into groups. At block 1335, these groups are formed automatically by embodiments.

Once groups are formed, the mobile devices for each member of the group is notified of the group, and different features can be explained. In some embodiments, site controller 812 uses contact information stored in NAS 850 to generate messages for group members. With respect to messaging, embodiments can combine standard approaches (e.g., text, audio, video) on the phone, with features that are only available to event sites. For example, text messages notifications can be sent using the venue video displays, LED sculptures and other similar approaches. Video messages announcing groupings can include members of a performing band and/or celebrity attendees. Other approaches would be apparent to one having skill in the relevant art(s), given the disclosure herein. In some embodiments, groups would be able to easily communicate using a variety of different approaches.

In an embodiment, site controller 812 can use phone switch 140 to cause an attendee's phone to ring or receive video call using a video calling service. In some embodiments, a call could be connected with another person in the venue or in the attendee's social graph who is inside or outside the venue. The identity of the call connection and origination location is unknown in one embodiment until the receiver says hello, hangs up or begins a conversation. In different embodiments, All over the venue attendees could be connected at random.

Continuing this example, after a minute or some other predetermined time of conversation, phone switch 840 can call a third person and patches them into the conversation. Then maybe a fourth, a fifth, or perhaps one of the original participants is bumped. The audio and/or video calls could be recorded and stored on NAS 850 for later use at the venue or another stop on the tour. The connected callers could be nearby, perhaps in adjacent seats or rows such that the call is an "ice-breaker" to facilitate meeting in person. The callers could be given the option to meet one or more persons on the call. Some embodiments could even facilitate a seat swap so that newly introduced attendees can change seats. Members of the band, performers or venue staff could even get on a call optionally. Phones could ring or calls could be terminated in synchronization with the performance. A message could interrupt the call to transition to the performance or otherwise notify the attendees of something.

In some embodiments, a phone video and/or audio could be patched directly to a stage display. The video camera on the mobile device 824 could be used to create a virtual "fan cam" for display on the stage display, thus providing display video without needing to send professional camerapersons into the crowd.

In an example, anybody attending a show at a venue can receive a phone call such that one doesn't need an app or a smartphone to be included. Calls can be received in the venue, for example, the concessions line, in the bathroom, in a venue bar, outside in the parking lot, in line to enter. Embodiments can ring any phone number that was associated with an attendee. Some embodiments could confirm that the registered phone number was at the show before connecting.

To promote communication between and among individuals within the formed groups, at block 1340, two members at a time are selected in a single group for pairing analysis. In an embodiment, this analysis is related to the event to which the audience is attending. One person may have been to recent concerts by this artist, and another person has not attended any concerts.

The purchase of souvenirs at shows can also be measured and compared based on credit card receipts. Interest in an artist can also be measured by searching for blog posts and other Internet information. In some embodiments different types of connection analysis can be used, e.g., similarity in general interests, like of different foods or sports teams, and/or other similar factors.

In block 1340, an affinity score is generated based on the types of analysis described above, and at block 1342, if the affinity score exceeds a threshold, communication links are established between the two analyzed people. In some embodiments, to promote connections between similar audience members, automatic communications are generated from one of the linked pair to another. These communication can be timed to synchronize with activities taking place within the show, e.g., different bands playing, different songs playing, and/or a guitar or drum solo.

As described with block 1350, some embodiments can select the method and timing of communications between pairs based on the information learned. For example, pairs judged to have a high affinity may prefer video calls over audio calls. In-person meetings can also be suggested at an early time. In block 1355, the communication is enabled between the pairs.

It should be appreciated that some embodiments can use an approach to grouping and connecting individuals that is less complicated than the processes described above. An embodiment can connect users in site networks using basic information about the individuals and estimated location.

An example method of method of linking mobile devices at an event using groups based on seating and activity includes the following:
  receiving a first indication that a first ticket for an event has been redeemed, the first ticket being associated with a first seat at the event;
  receiving a second indication that a second ticket for the event has been redeemed, the second ticket being associated with a second seat at the event, the first and seconds seats being different seats;
  retrieving first information associated with a first mobile device, the first mobile device being associated with the first ticket;
  retrieving second information associated with a second mobile device, the second mobile device being associated with the second ticket;
  analyzing the first and second information;
  grouping the first and second mobile devices into a first group based on the analyzing and respective locations of the first and second seats;
  establishing a first link between the first and second mobile devices based on the analyzing; and
  based on an activity at the event, enabling a first communication between the first and second mobile devices based on the first link.

Figure 14:
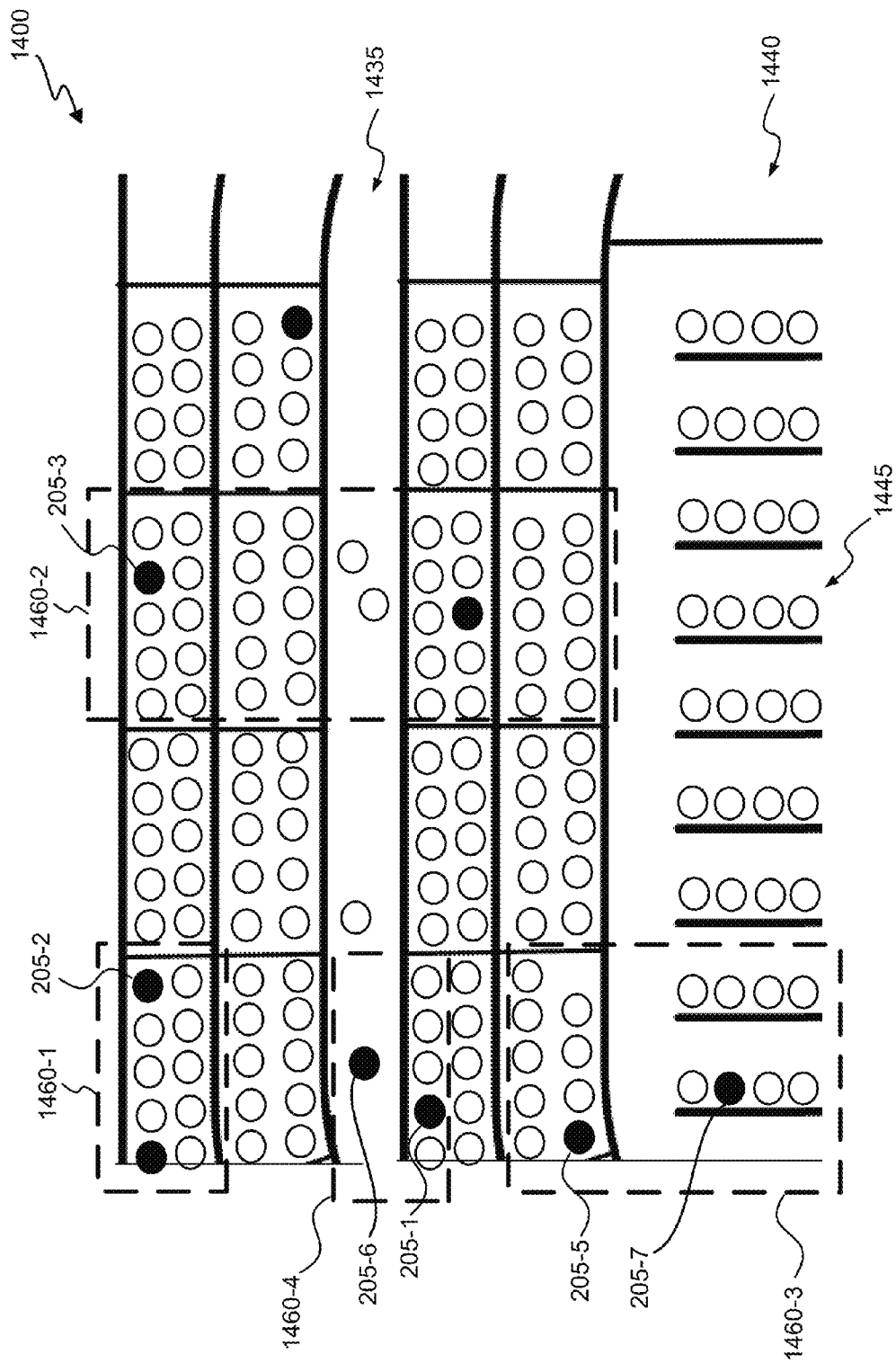
FIG. 14 shows a block diagram of a seating arrangement in a venue according to an embodiment.

Referring to FIG. 14 a diagram of a seating arrangement 1400 in a venue is shown.

Groupings shown with dotted lines (e.g., 1460-n) demonstrate the capability of the generated groups to foster interactions among different attendees (e.g., persons 205-n). Some embodiments add additional factors to the grouping approaches discussed with FIG. 13 above, adding criteria that reflects a seating diversity, e.g., seats from different sections, different types of seats (e.g., raised or floor), whether a mobile device is associated with a seat at all (e.g., standing room only admission), can all be evaluated by some embodiments to advantageously group users.

For example, group 1460-3 integrates those from a raised section (e.g., user 205-5) and a user in floor section 1440 (e.g., user 205-7). In another example, the flexibility of the system allows User 205-6 standing on walkway 1435 to be in a group with seated user 205-1. In group 1460-4, two people with common interests—one standing (205-6) in an isle (1435) and one sitting in a seat (205-1) can be linked into an affinity group, and connected using approaches described with FIGS. 13-15.

Figure 15:
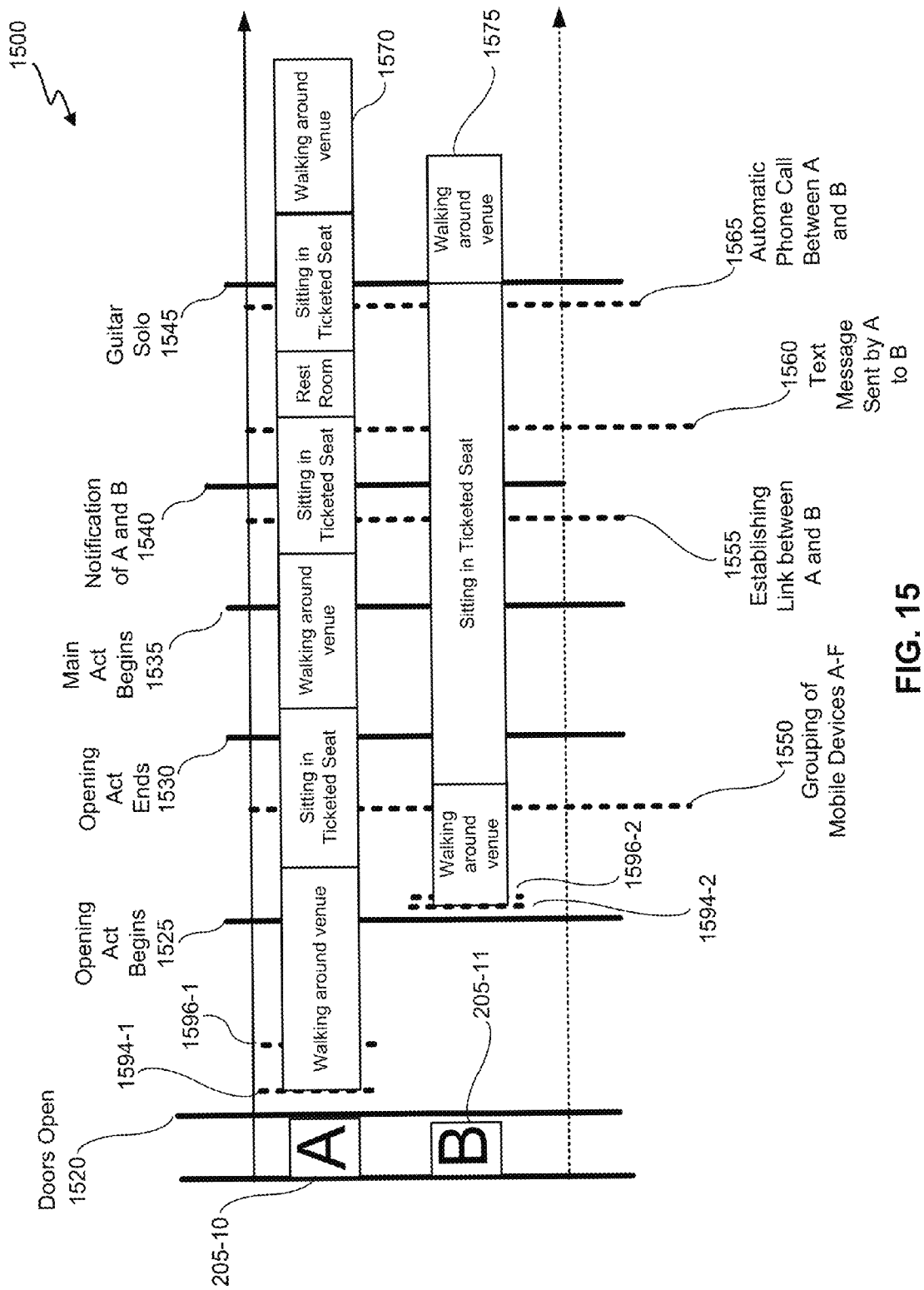
FIG. 15 illustrates a timeline of event activities and attendee contact according to an embodiment.

FIG. 15 shows a timeline 1500 that illustrates how some embodiments can use event activities to influence the timing of contact between two attendees: Users 205-10 (A) and 205-11 (B). In this example, an event begins at point 1520 where doors open to let attendees in. Soon after, User A redeems his ticket 1594-1 for entry, with access management system validating the ticket code and issuing instructions to a computerized turnstile. While walking around the venue, mobile device 824-10, which User A carries, automatically connects to access points 820 using WiFi. Access points 820 reads the Media Access Control (MAC) Address of mobile device 824-10 and relays this uniform identifier to site controller 812. Site controller 812 queries access management system 285 to determine whether the MAC address is associated with a ticket. Because User A purchased his ticket using mobile device 824-10, this MAC address is stored as associated with the ticket. Because the ticket is associated with his identity, mobile device 824-10 is now associated with his identity.

In the meantime, User B uses her mobile device 824-11 to redeem an electronic ticket 1594-2. Because she redeemed an electronic ticket with mobile device 824-11, this mobile device is connected to site network 816 when the electronic ticket was redeemed 1596-2. While both Users A and B are walking around, Users C-F also have their devices join site network 816. Based on similar characteristics, users A-F are grouped into a group (1550) based on data retrieval and analysis performed by site controller 812. Users A-F all get a notification message that they have been linked in a group of five attendees. A map shows them where each member of the group is, and some selected media from other social networking accounts for several of the users.

As described with FIG. 13 above, based on the established group, an additional analysis is can be performed regarding an affinity score for member of a group, e.g., Users A and B. After this analysis, while both users are sitting in their ticketed seats, an additional notification arrives telling them that they have been specially linked 1555. User A uses the opportunity to send a text message to User B at point 1560, then both users settle into watching the show. At point 1565 however, both of their phones ring to connect them. As they answer, they both hear the lead guitarist for the band they are watching thank them for attending, and tell them to get ready for his big guitar solo at point 1545.

It should be appreciated that some embodiments are able to synchronize automatic mobile device functions with both scheduled and ad-hoc activities in an event. Scheduled activities rely upon a synchronization of clocks between site system 280 servers and mobile devices 824. Ad-hoc events can be used to control the operation of system components (e.g., messages sent by site controller 812) by detectable triggering events (e.g., by particular sounds, and/or lights). Thus, with regard to the example above, the guitar solo could not be scheduled, but a particular combination of sounds leading up to the solo in the song could be detected.

Figure 16:
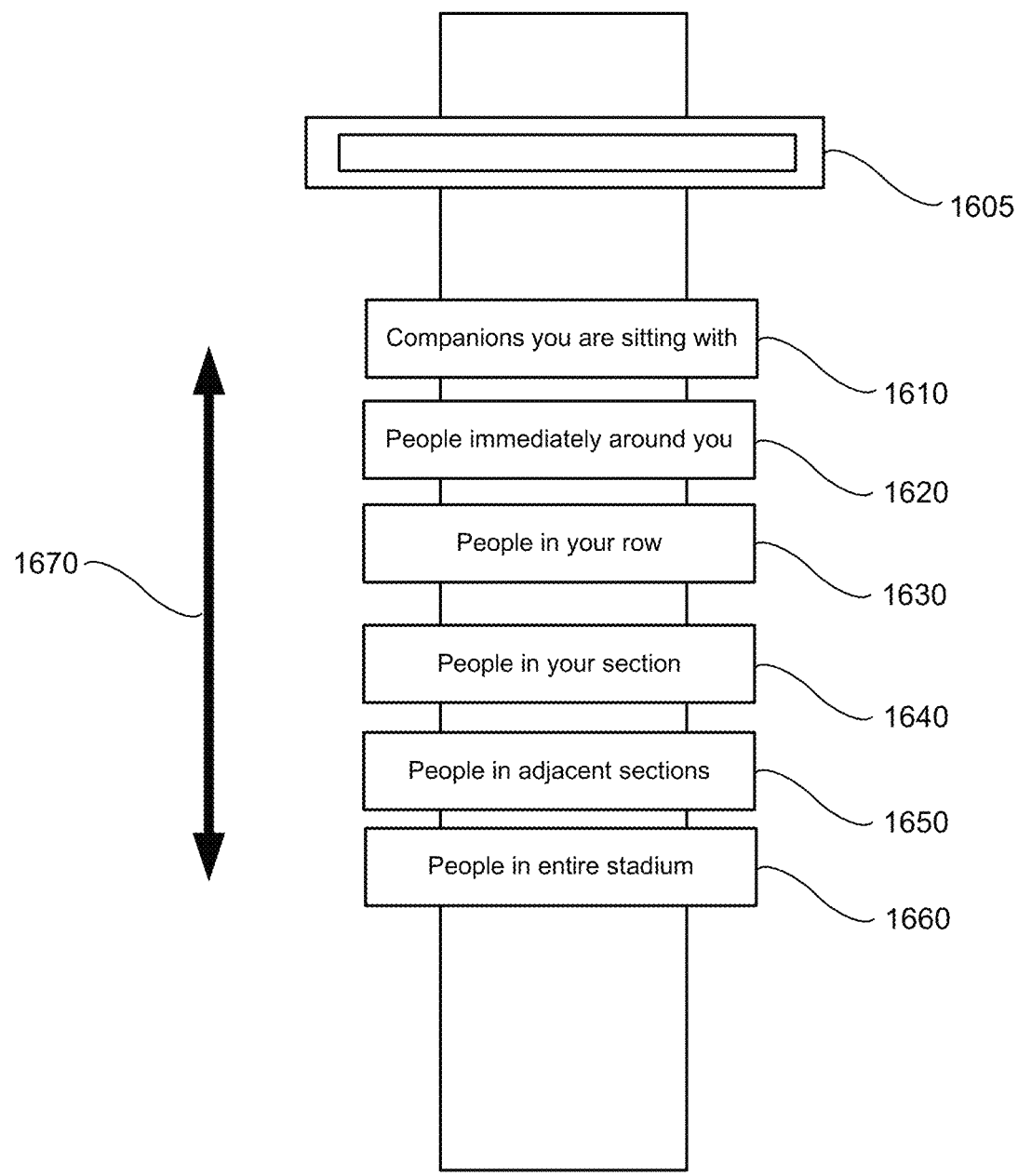
FIG. 16 shows a block diagram of a system for automatically grouping attendees in a venue according to an embodiment.

Continuing with FIG. 16, this figure shows how affinity groups described above with FIG. 13 can be used to intuitively link people. In an example, after users are automatically linked into one or more groups based on approaches similar to the ones described with FIG. 13 above, slider 1605 can be used to select a range of people over a spectrum of inclusion 1670.

When a user wants to select a group to receive a group communication, the slider 1605 interface can improve the operation of this selection of recipients. In some embodiments, by linking the sharing of content to physical space and the organization of recipients within the space (e.g., people in a section, people around you), the slider is rooted to the physical world. With its predictable delivery of messages within a set space, it provides clear, tangible results. As indicated on the slider settings, the device allows for the selection of ever wider or narrower groups of recipients. This interface feature can be combined with the grouping based on seats, activity and affinity described with the description of FIG. 13.

Figure 17:
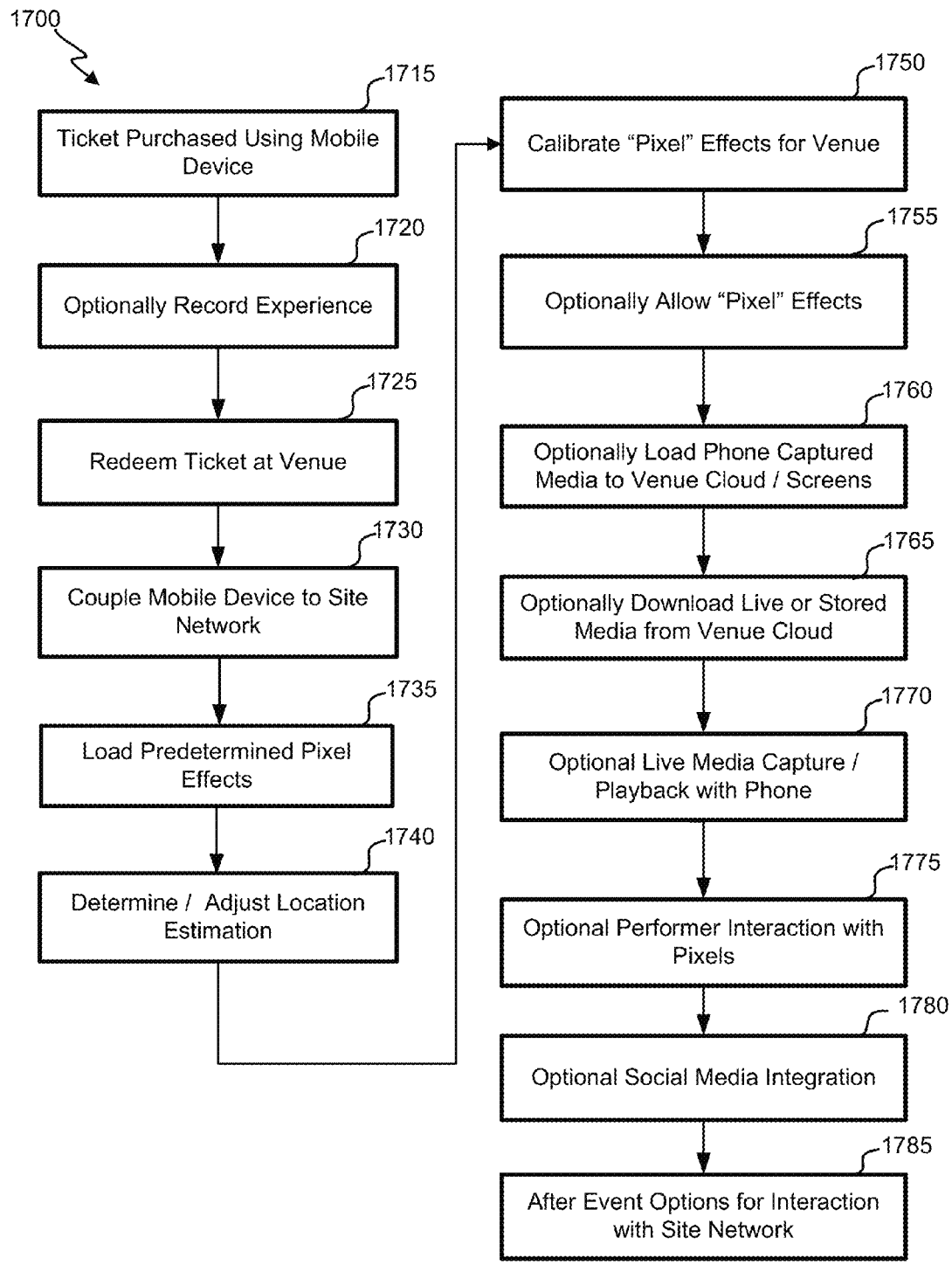
FIG. 17 illustrates a flowchart of a process for using displays of multiple mobile devices to display a single image at an event according to an embodiment.

FIG. 17 illustrates a flowchart of an embodiment of a process 1700 for using each display of multiple mobile devices to display a single image at an event. The depicted portion of the process begins in block 1710, where the user purchases a ticket using an app, web page or physical location. The ticket is loaded onto the app to become an electronic ticket or at least record the exact location of the seat and row. In block 1720, the user can optionally record the experience or their thoughts in buying a ticket with sound, video and/or a photo.

In one embodiment, the mobile devices 824 are transformed into a visual canvas within the venue. To identify location, seat location could be used as gathered from the electronic ticket or manually entered, or the GPS signal on the mobile device 824, or ranging from wireless or sound signals. For example, the microphone on the end user device could be used to record sound signals from the performance or test tones that the app could use to triangulate location in the venue.

In various embodiments, many different visual effects can be accomplished by embodiments within the venue, for example:
 Run color through the screen of all mobile devices 824 in the arena
 Paint legible bold text at large scale across the arena— using each mobile device 824 or cluster of mobile devices 824 as a 'pixel' for dot matrix lettering
 To control the flashlights or LEDs on each mobile device 824 to create bold simultaneous flashes of light throughout the audience
 Turn on and off screens in synchronization or status lights/LEDs In some embodiments, the location uncertainty of mobile devices 824 can be quantified and used to select and/or modify the display of images. For example, for locations that are very precise down to the seat, finer grained effects could be used such as a pixel in an image or text. Where estimated locations of mobile devices are less precise, color change, pulsating or modulating effects across the entire venue can be used. At any given moment, mobile devices 824 could be grouped and associated with different effects according to their location accuracy to create a chorus when done in sync. Effects that work best with a certain pixel density could avoid areas of the venue where that doesn't exist or could be postponed, canceled or substituted with another effect.

An additional effect that can be generated by embodiment is a wave of sound and color to compliment a wave of attendees standing in synchronization. The flash feature of the phone could be used to mark the creshendo of the wave as it circles the venue. The vibration feature of the phone could indicate to the attendee exactly when to stand in syncrhonization with the wave. Optionally, a photo could be taken when the flash is activated for upload and storage on the NAS 850 to enhance the content available at the venue.

Returning to the discussion of process 1700, on the day of the event, the user checks into the event in block 1725. Checking in could be through an entrance or automatically as the electronic ticket is used. For example, when in contact with the site network 816, the ticket could be marked as used. Mobile device 824 can be connected, in block 1730 to site network 816. In block 1735, predetermined pixel effects are loaded into the mobile device 824. The pixel effects include things like color changes for the screen, flash activation sequences, sounds, video, and/or vibration sequences. The clock on the mobile device 824 is synchronized to the site network or an offset from an absolute reference in the venue is stored on the mobile device 824. In this embodiment, synchronizing allows the pre-loaded pixel effects to happen at a predetermined time.

A determination of location is shown in block 1740. This determination can be recurring and adjusted as the user might move throughout the venue. Some embodiments calibrate the pixel effects in block 1750. A video camera or microphone in the venue could be used to receive feedback from pixels when they activate a pixel effect. Should a pixel be out of place, the location could be adjusted to correct for the location error. The brightness and sound amplitude could be adjusted also. There could be calibration points distributed throughout the venue or other pixels could be used to gather that information. For example, in a small area one phone could have its speaker emit a tone that is recorded through the microphone of several other phones to verify the location of the both the emitting phone and those receiving the sound.

At various times during the event the pixel effects are performed in block 1750. Activation of a pixel effect is triggered by identifying the effect and providing a synchronized time for performing the pixel effect. In block 1780, content is captured on the mobile device 824 at the option of the user or at the command of the site controller 812. In block 1765, live or stored content is downloaded from the site network to the end user device for playback immediately or at a later time. Some embodiments could have the content played in synchronicity with the live performance, for example a slide show of photos gathered inside or outside the event could be played to accompany the performance. Live content can also be captured with another pixel or by the venue for playback with the mobile device 824 in block 1770.

The performer can optionally interact live with the pixels in block 1775. For example sweeping their hand across the crowd could cause a wave of color, sound and/or vibration to play on the mobile device 824. Content or information from the venue could be forwarded to each user's social media accounts in block 356. After the event, the site network 816 and the content stored on the NAS 850 can be accessed by attendees. For example, videos and photos gathered at the event are accessible through the Internet 528. As the performers tour, site network 816 can be moved in whole or part to the next venue.

Figure 18:
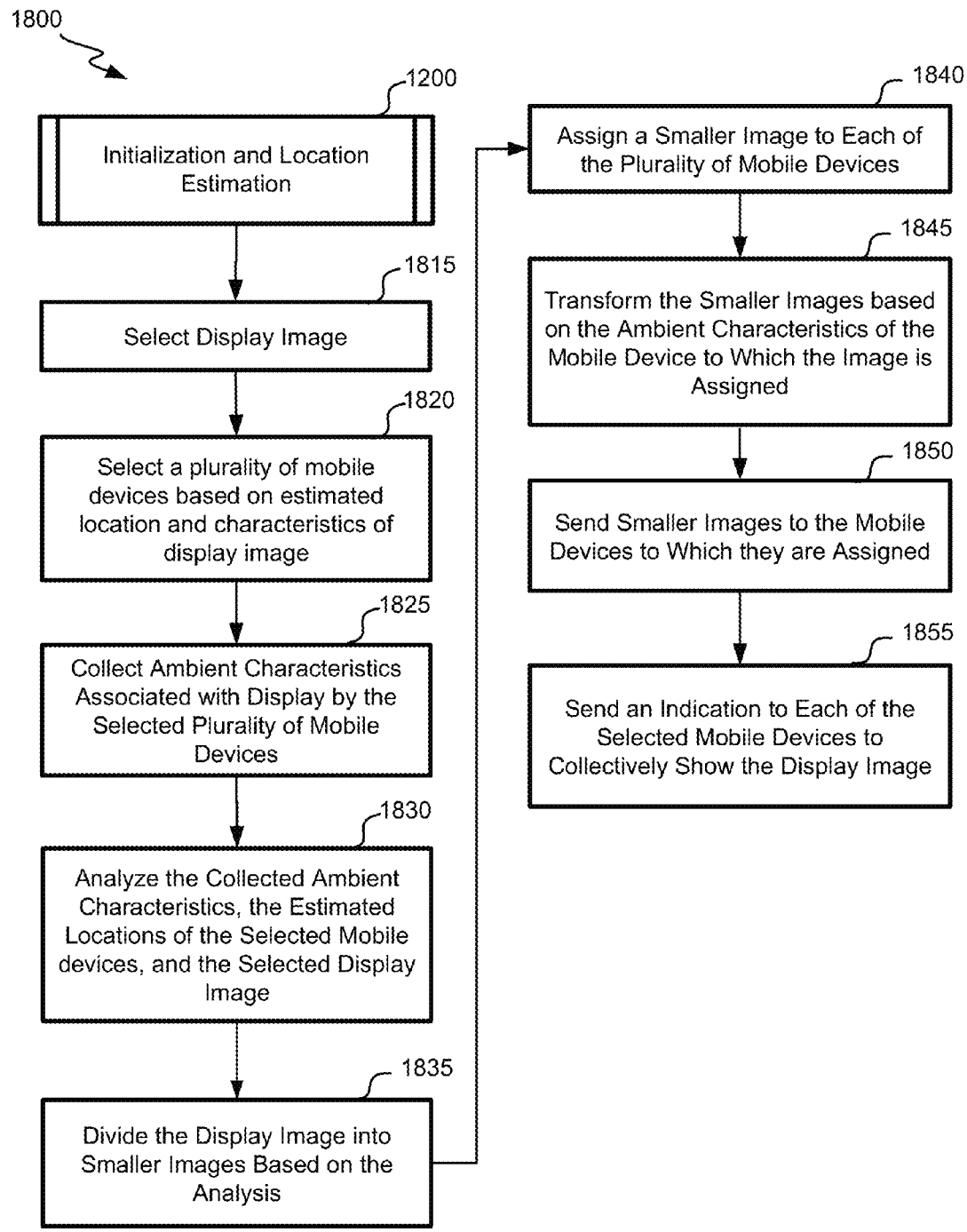
FIG. 18 illustrates a flowchart of another embodiment of a process for using displays of multiple mobile devices to display a single image at an event.

FIG. 18 illustrates a flowchart of another embodiment of a process 1800 for using each display of multiple mobile devices to display a single image at an event. At block 1200, the initialization and location estimate process is performed. In block 1815, an image for display at an event using multiple devices is selected. In block 1820, site controller 812 accesses a three-dimensional model of the venue (e.g., 3d model 1038) and transforms the placement of people, mobile devices and seats into a plan to select multiple mobile devices for display of the selected image. The selection of the multiple mobile devices is based on the estimated location of each mobile device, and characteristics of display image.

In block 1825, ambient characteristics associated with display by the selected mobile devices are collected. In block 1830, the collected characteristics, the estimated locations of the selected mobile devices, and the selected display image are analyzed. In block 1835, the selected display image is divided into smaller images based on the analysis. In block 1840 each smaller image is assigned to one of the selected mobile devices. In block 1845, the smaller images can be transformed based on collected ambient characteristics associated with the mobile device to which the image is assigned. In block 1850, the transformed smaller images are sent to the mobile devices to which they are assigned. In block 1855, an indication is sent to each of the selected mobile devices to collectively show the display image.

Figure 19:
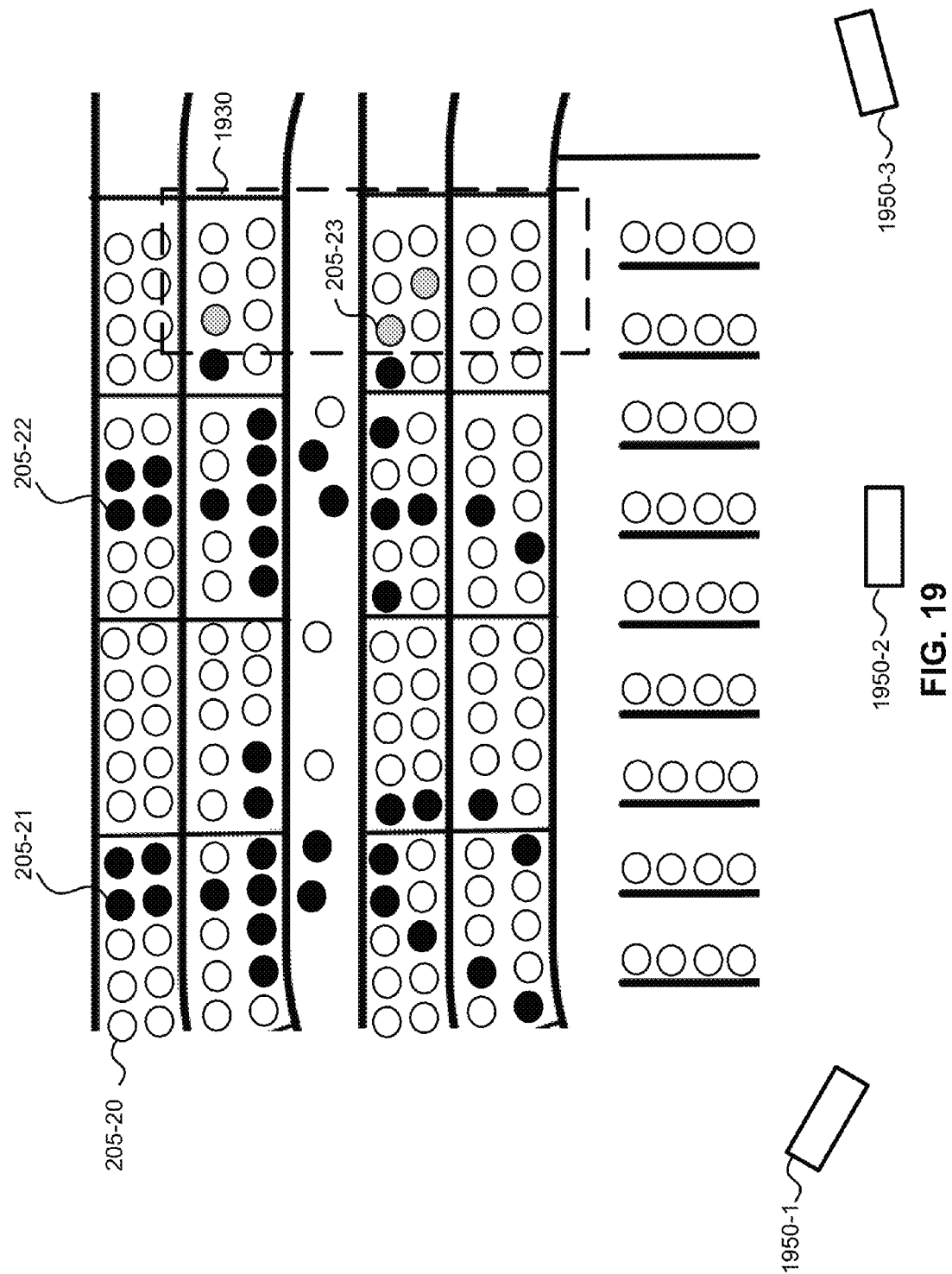
FIG. 19 shows a diagram of using displays of multiple mobile devices to display a single image at an event according to an embodiment.

Referring to FIG. 19, an example of the process, as described with FIG. 18 above, for using each display of multiple mobile devices to display a single image at an event is shown. FIG. 19 shows sections of seating in a venue. In this example, each white dot (e.g., 205-20) represents a seat having a user 205, and each black dot represents a user (e.g., 205-22), holding up a mobile device 824 that is engaging in the collective display of an image or video. In this example, a video of a running man is represented, with two stick figures showing how animation could be achieved. It should be appreciated that the resolution of image and video displays, with this approach is only limited by the density of people and/or he size of the mobile device screens used (e.g., smartphone, tablet and/or other devices described herein).

As discussed above with FIG. 18, some embodiments of this collective display approach can measure ambient characteristics of the display environment and transform the display characteristics of different smaller display images to compensate. This measurement and adjustment is illustrated by area 1930 in FIG. 19, as representing an area where the display can be improved by adjustments. The adjustments are illustrated by the grey dots (e.g., 205-23), these dots having an adjusted color to display better in area 1930. As noted with the discussion of FIG. 18 above, cameras can be used to measure the quality of the collective image display, and calibrations can be made. By sampling the display from different distances and angles, calibration cameras 1950-1, 1950-2, and 1950-3 can be used to implement the adjustments described above.

Figure 20:
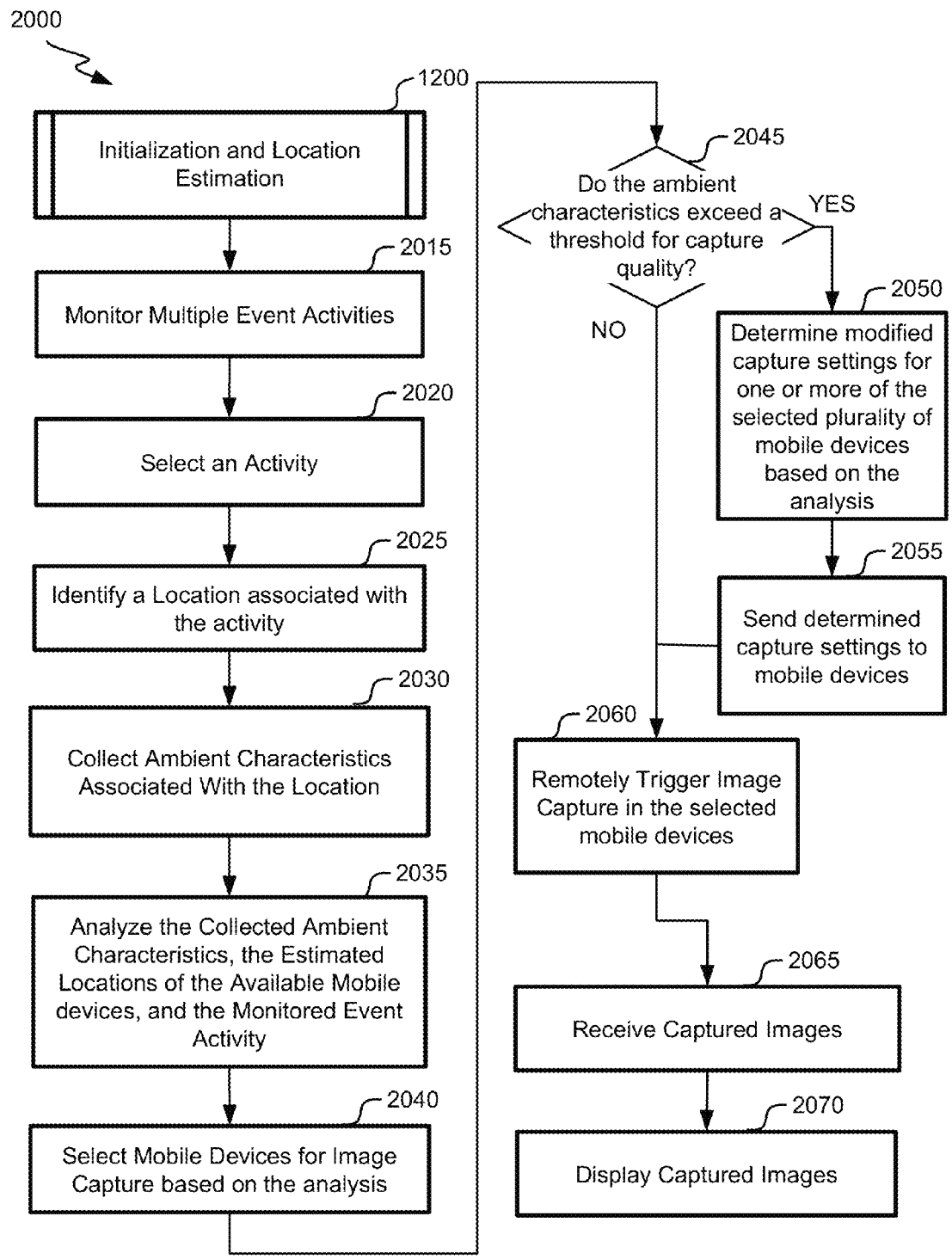
FIG. 20 illustrates a flowchart of an embodiment of a process for displaying images received from multiple mobile devices at an event according to an embodiment.

FIG. 20 illustrates a flowchart of an embodiment for using activities and locations associated with tickets to display images received from multiple mobile devices at an event. In addition to emitting audio and visual information as a contribution to the event, information could be captured by the audience mobile devices 824, and through the site network 816, and emitted beyond the venue—to extend the reach of the experience. In various embodiments, content can be gather in any number of ways using the app on the mobile device 824, for example:

- Mobile devices 824 take a photograph simultaneously—the photographs are stitched together to form a 'mass photograph' of the event—a cubist fractured image from multiple angles—which is transmitted to NAS 850 or shared through the Internet 128, e-mail, and/or social networking outlets.
- Multiple Mobile devices 824 can be triggered to take a 'selfie'—the photographs can then be stitched together to form a 'mass photograph' of the audience—this becomes a cumulative mass photograph—which is transmitted to the storage array 132 or shared through the Internet 128, e-mail, and/or social networking outlets.
- Mobile devices 824 record its owner singing at the concert—the recordings are layered together to form a mass choral track—this becomes a cumulative mass chorus recording—being added to each night of the tour—which is transmitted to the storage NAS 850 or shared through the Internet 128, e-mail, and/or social networking outlets.

At block 1200, the initialization and location estimate process is performed. At block 2015, multiple activities associated with an event are monitored. In an embodiment, site controller 812 can monitor the occurrence of different events, such as different bands playing, or the occurrence of particular sounds. In block 2020, an activity is selected, and in block 2025, a location is identified that is associated with the selected activity. I embodiments, site controller 812 can utilize 3D model 1038 to provide location information for activities monitored by video.

In block 2030, ambient characteristics associated with the location are collected, and the characteristics are analyzed along with the estimated locations of the mobile devices available for collection. In block 2040, mobile devices as selected based on this analysis. In block 2045, the collected ambient characteristics are compared to a threshold, and, if the threshold is exceeded, in block 2050, modified capture settings are created based on the analysis. In block 2055, the modified capture settings are sent to the selected mobile devices.

At block 2060 (also the block that would have executed if the threshold had not been exceeded), the trigger capture is triggered in the selected mobile devices. At block 2065, the captured images are displayed, and at block 2070, the captured images are displayed.

Figure 21:
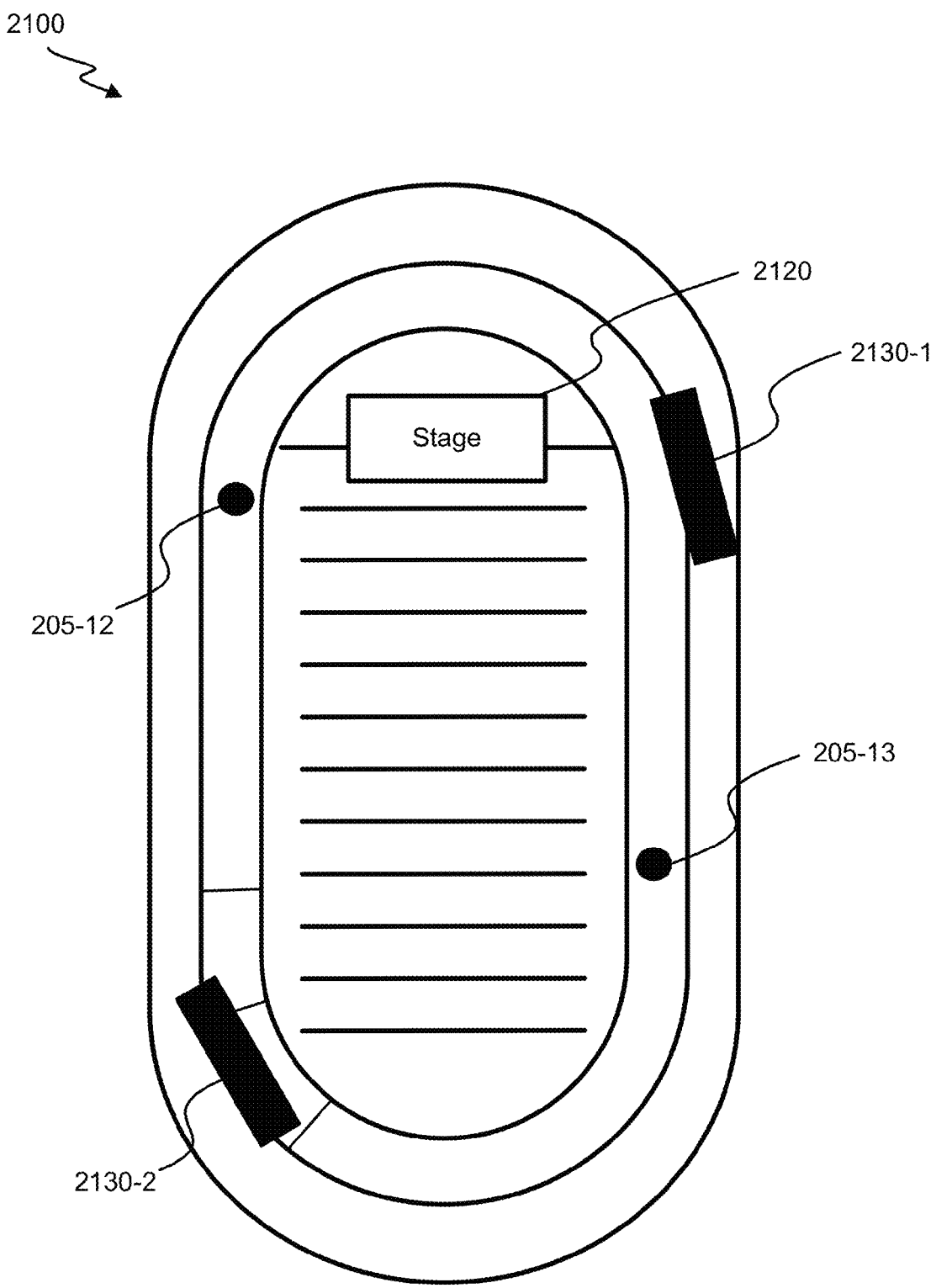
FIG. 21 shows a diagram of a system for automatically triggering the capture of media by multiple mobile devices at an event according to an embodiment.

FIG. 21 shows an overhead view of a stadium 2100 having a stage 2120, and two stadium video displays (2130-1 and 2130-2). Two users, 205-12 and 205-13 are shown at opposite ends of the stadium. The description of FIG. 22 below describes the interaction of these elements with site system 280, according to an embodiment.

Figure 22:
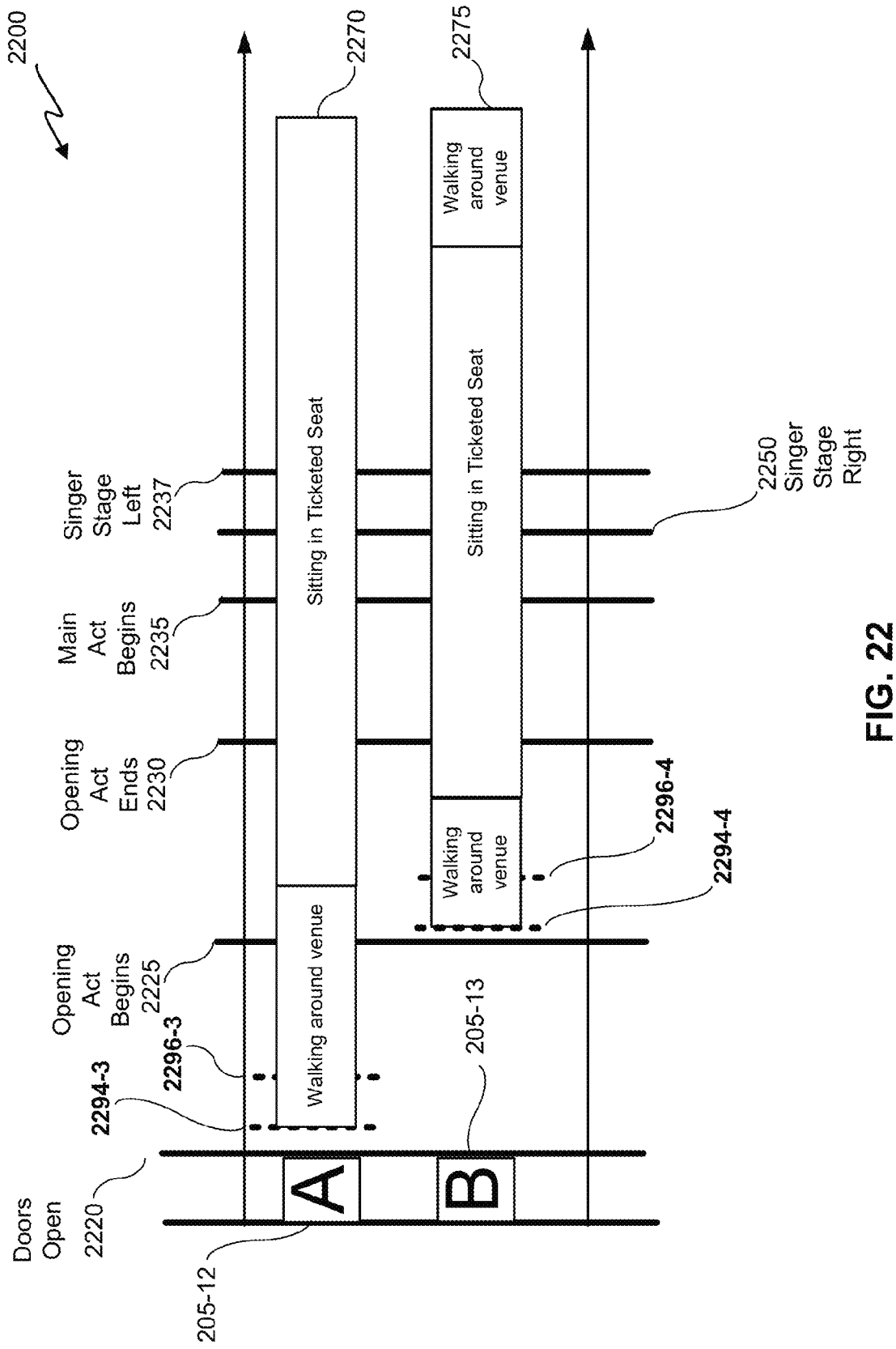
FIG. 22 illustrates a timeline of an embodiment of a process for automatically triggering the capture of media by multiple mobile devices at an event according to an embodiment.

FIG. 22 shows a timeline 2200 that illustrates how some embodiments can use show activities to automatically trigger the capture of media by multiple mobile devices. An event in stadium 2100 begins at 2220 where doors open to let attendees in. Soon after, Users 205-12 and 205-13 redeem their tickets 2294-3, 2294-4 for entry, with access management system 285 validating the ticket code and issuing instructions to a computerized turnstile. Both users connect to access points 820 using WiFi and take their seats as depicted in FIG. 21.

At the beginning of the main act (2235), in an embodiment, site controller 812 begins to send control signals to mobile devices 824-10 and 824-11, held respectively by Users 205-12 and 205-13. Site controller has selected these two devices for the capture of images for display during the concert. This selection can be made based on one of more factors that can affect the image capture (e.g., location in the venue, age of the mobile device holder, type of mobile device to be used, and/or other similar characteristics). The control signals are controlling both camera settings (e.g., exposure, shutter speed, focus) and the triggering of the camera capture.

After the main act begins at 2235, both users stand up and have their devices pointing out, such that their camera lenses are facing the stage. In some embodiments, site controller 812 can send control signals that cause the mobile device to request this camera position. In some embodiments, at a given time, multiple mobile device cameras may be available and controlled by site controller 812, but only a portion are used to collect images. The automatic selection of cameras can be affected by many factors, including: the type of mobile device and quality of camera, the angle at which the camera is held, the vantage point of the camera, and/or other similar features.

Continuing this example, at point 2250, where the singer stands stage right to address the crowd, both mobile devices held by users 205-1 and 13 are held ready to capture. As FIG. 21 depicts however only User 205-12 is in a position to take a picture. When triggering capture, site controller 812 can use image parsing technology to determine the composition of potential images. In this example, site controller 205-12 only triggers the capture of an image for User 205-12.

In this example, stadium video displays (2130-1 and 2130-2) are positioned such that User 205-12 can only see stadium video display 2130-1 but not display 1830-2. As discussed herein, site controller 812 maintains an estimate of different mobile device locations (the mobile device of user 205-12 was selected based, in part, on its position). In some embodiments, site controller 812 can maintain a 3D model of stadium 2100 (e.g., in site information storage 1037), and can estimate vantage points for different locations within the stadium. Based on these capabilities, for each picture captured to be displayed, site controller 812 can determine which displays can be seen by which users. In some embodiments, to improve the mass collection and display of media, displays are selected based on promoting the most happiness from picture takers. Thus, in this example, video display 2130-1 is selected to display the picture that was captured by user 205-12's mobile device.

Figure 23:
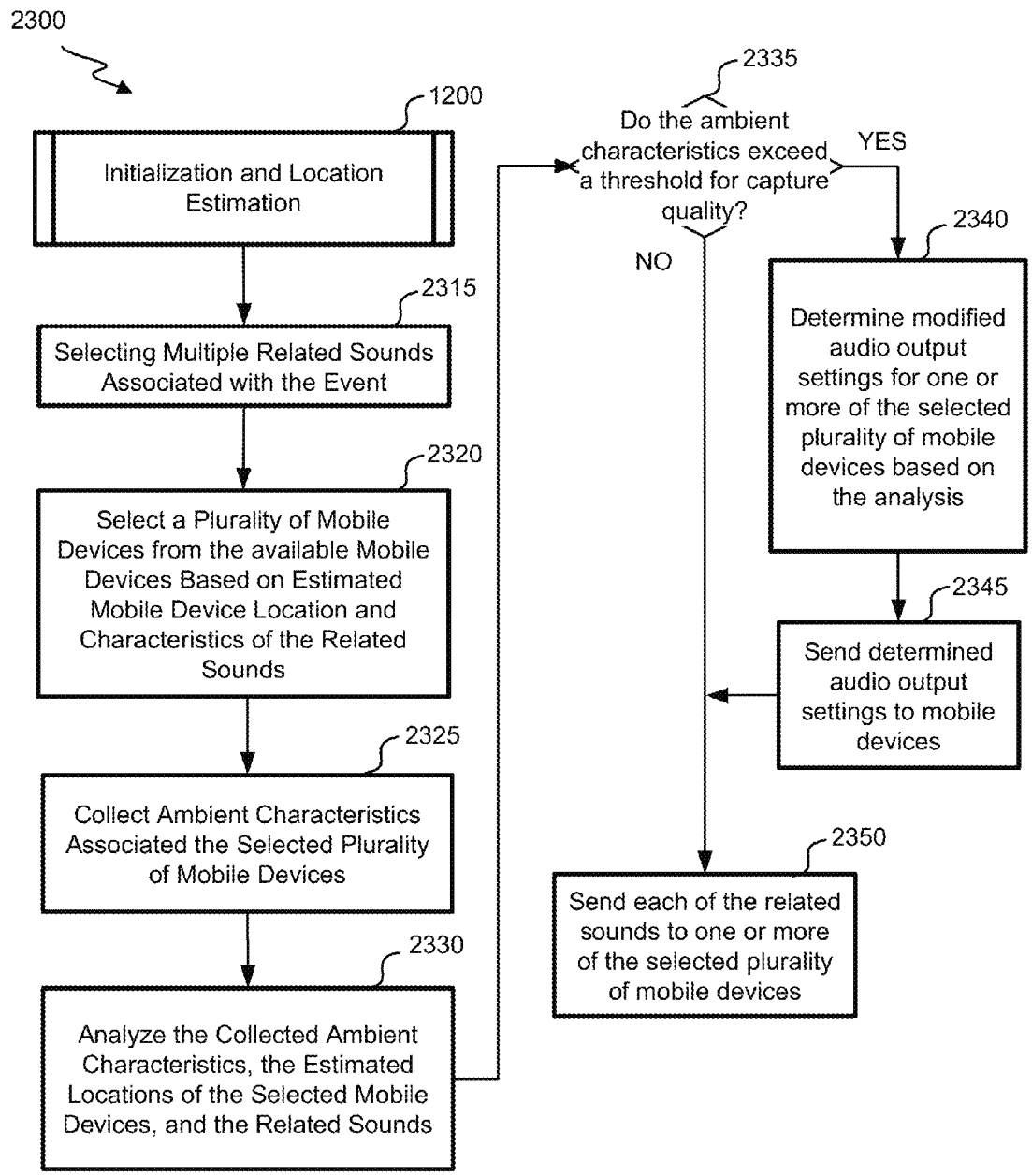
FIG. 23 illustrates a flowchart of an embodiment of a process for using speakers of multiple mobile devices to output sounds at an event according to an embodiment.
Figure 24:
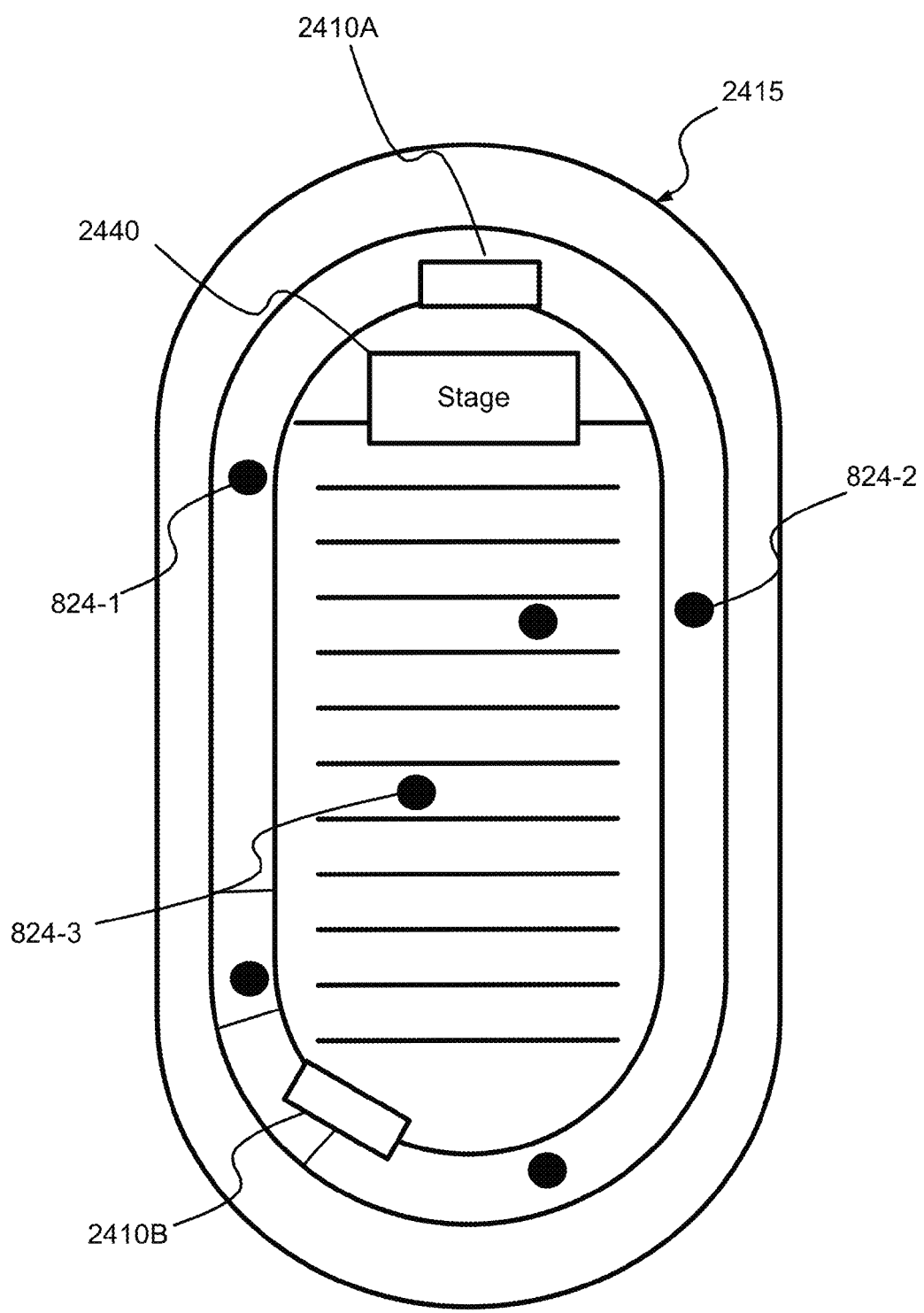
FIG. 24 shows a diagram of a system for using speakers of multiple mobile devices to output sounds at an event according to an embodiment.

With reference to FIG. 23 a flowchart of an embodiment of a process 2300 that uses each speaker of multiple mobile devices to output sounds at an event. FIG. 24 is an illustration of a stadium where an embodiment of process 2300 is implemented during a musical performance from stage 2440. Mobile device 824-1, 824-2, and 824-3 are used by embodiments. To calibrate the output of the multiple mobile devices 824, microphones 2410A and 2410B are used.

At block 1200, the initialization and location estimate process is performed. For example, a connection by mobile device 824-1 is received by access points 820, and the location of mobile device is estimated. In some embodiments, site controller 812 uses the location estimates for the available mobile devices to map them in a 3D model stored in site information storage 1037. At block 2315, multiple related sounds associated with the event are selected. In this example, the artist performing at the concert select some high and low sounds that will complement the instruments heard through the concert sound system. At block 2320, multiple mobile devices 824 are selected from the available mobile devices based on estimated mobile device location and characteristics of the selected related sounds. As for all embodiments discussed herein that use capabilities of mobile devices, for this analysis, in some embodiments the model of the mobile device can be taken into account when selecting mobile devices for different activities.

At block 2325, ambient characteristics associated with the multiple mobile devices 824 are collected. At block 2330, the collected ambient characteristics, the estimated locations of the selected mobile devices, and the related sound are analyzed. In block 2335, the collected ambient characteristics are compared to a capture quality threshold, and, if the threshold is exceeded, in block 2340, modified capture settings are created based on the analysis. In block 2345, the modified capture settings are sent to the selected mobile devices. At block 2350 (also the block that would have executed if the threshold had not been exceeded), each of the related sounds are sent to one or more of the selected plurality of mobile devices.

In some embodiments, microphones 2410-1 and 2410-2 can be used to measure the quality of the sounds generated by this process. Having multiple calibration microphones not only gives a larger, and more useful sample size, but also lets the directional aspects of the generate sounds be measured.

One embodiment of this process uses the mobile devices 824 of the audience as a musical instrument: for the band to be able to 'play' all like a 20,000 key keyboard and/or a 20,000 fret guitar, for example. In another embodiment, the voices of the audience are individually recorded with their mobile devices 824 as content stored on NAS 850. Site controller 812 can also 'play' the audiences' voices to create an effect in the venue or create a recording that would include the voice of every single audience member on the entire tour or a subset such as one show.

In one embodiment, a component of site system 280 (e.g., sound system controller 1016) can establish a connection with mobile device 824 so as to have mobile device 824 act as an amplifier and speaker (e.g., using speaker 962). Site system 280 (e.g., using sound system controller 1016) can divide a song (and/or any other audible signal) up into constituent parts and spread these across different groups of selected mobile devices 824. In an example the song could be divided such that some mobile devices would play the drums, some the harmony, some the melody, some the lyric line, etc. In some embodiments, the audio effects can be combined with visual effects on mobile devices 824.

In one embodiment, part of the act of buying the ticket could include the recording of the ticket holder's voice. The app could ask the future attendee to state their name or for any other phrase to be state or simply ask that the future attendee say whatever occurs to him or her. The voices could also be transposed into a tone of variable length and key and register, etc. During the show, the recorded voices could be modified, combined and/or otherwise altered, then broadcast at the show. Broadcast could be using the standard show sound system and/or the distributed approach described with FIGS. 23 and 24 above.

Figure 25:
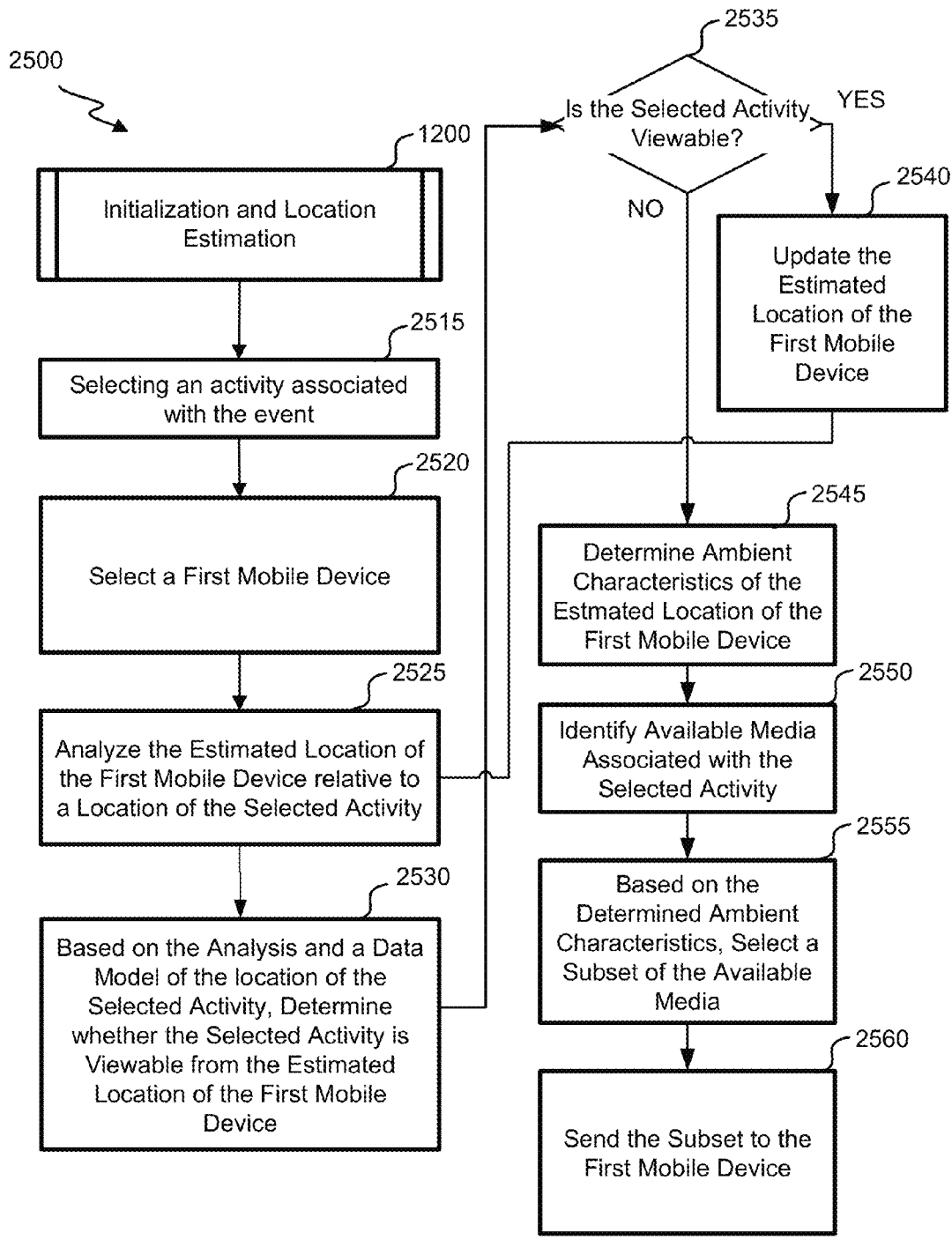
FIG. 25 illustrates a flowchart of an embodiment of a process for automatically outputting media associated with an event to mobile devices at the event according to an embodiment.
Figure 26:
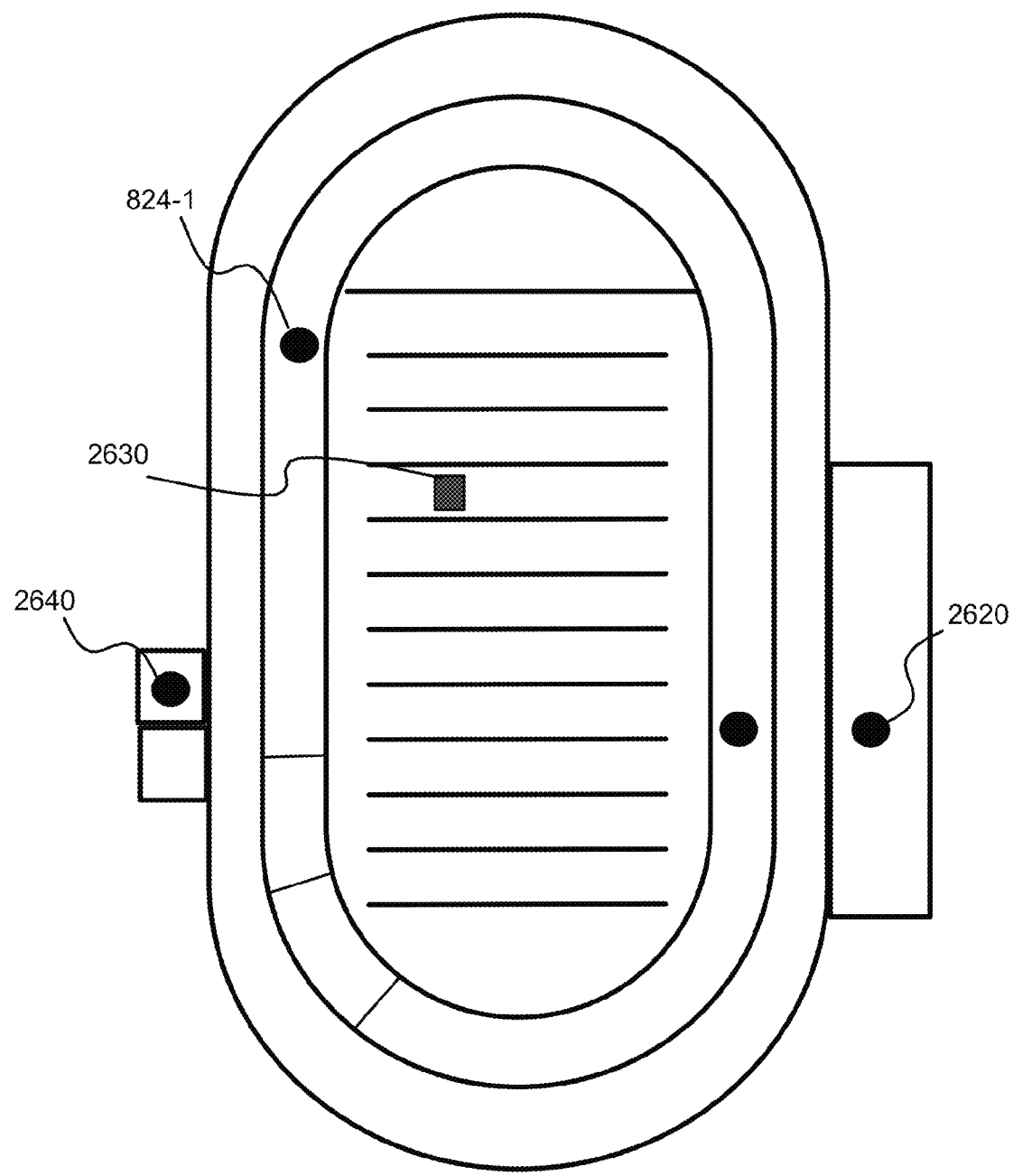
FIG. 26 shows a diagram of a system for automatically outputting media associated with an event to mobile devices at the event according to an embodiment.

FIG. 25 shows an embodiment of a process 2500 for automatically outputting media associated with an event to mobile devices based on the locations of mobile devices relative to activities at the event. FIG. 26 illustrates an implementation example of process 2500, using a stadium having areas where activity on the field is not visible. At block 2510, the initialization and location estimate process 1200 is performed, and at block 2515, an activity is selected that is associated with an event. For example, in a football game event, the activity selected could be the play on offense of one of the teams. On FIG. 26, item 2630 represents a location of an activity that a spectator shown as having mobile device 824-1 would not want to miss.

At block 2520, a first mobile device is selected to act as a measure of whether an activity is visible, and the estimated location of the mobile device is analyzed relative to a location of the selected activity. At block 2525, the estimated location of the first mobile device relative to a location of the selected activity is analyzed. At block 2530 and 2535, based on the analysis and a data model of the location of the selected activity, a determination is made as to whether the selected activity is viewable from the estimated location of the first mobile device.

In this example, mobile device 824-1 has a clear view of location 2630, but does not have a view from positions 2640 (e.g., an elevator) and 2620 (e.g., a restaurant). When the determination is estimated not to be viewable, block 2545 uses sensors on mobile device 824-1 do determine ambient characteristics of the location, e.g., an elevator bank and a bathroom would likely be silent, while a restaurant can be loud. In block 2550, an assessment is made as to the different available ways that information about the activity could be sent to mobile device 824-1 (e.g., is there a descriptive audio stream, a video stream viewable on the mobile device). In the embodiments that use site controller 812, a determination can be made as to whether available media can be delivered to a nearby video monitor.

In block 2555, based on the characteristics of the location, an available media solution is provided to mobile device 824-1, or other usable display.

Figure 27:
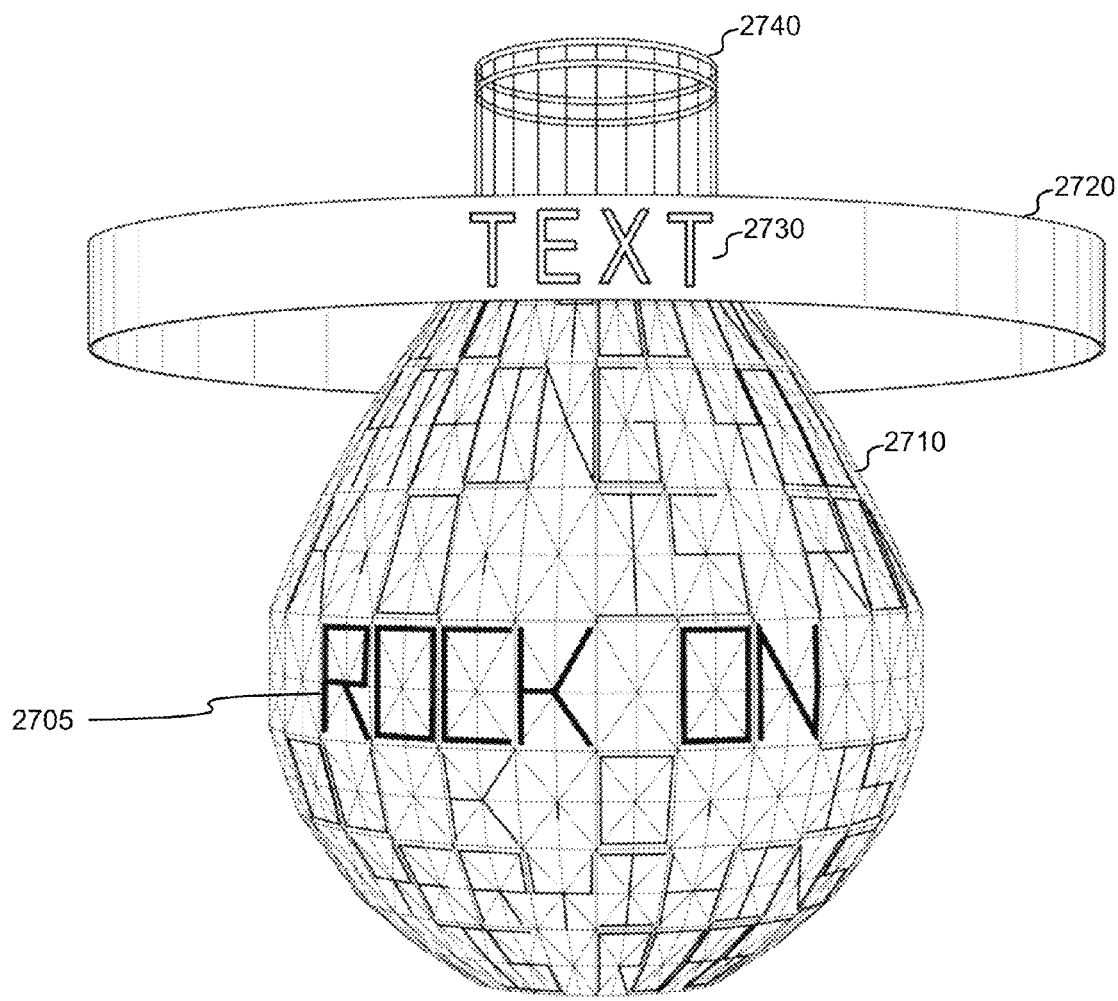
FIG. 27 shows a diagram of a data presentation sculpture according to an embodiment.

FIG. 27 shows an embodiment of a stage display sculpture resembling a giant lightbulb 2740 with a digital surface 2710 that can relay information 2705 from/to the crowd. An additional signal surface 2720 can be provided that allows for additional messages 2730 to be displayed. In some embodiments, information gathered at the venue could be displayed on stage displays such as a person's full or partial name, a photo that was captured by embodiments, gathered text messages, etc.

Figure 28:
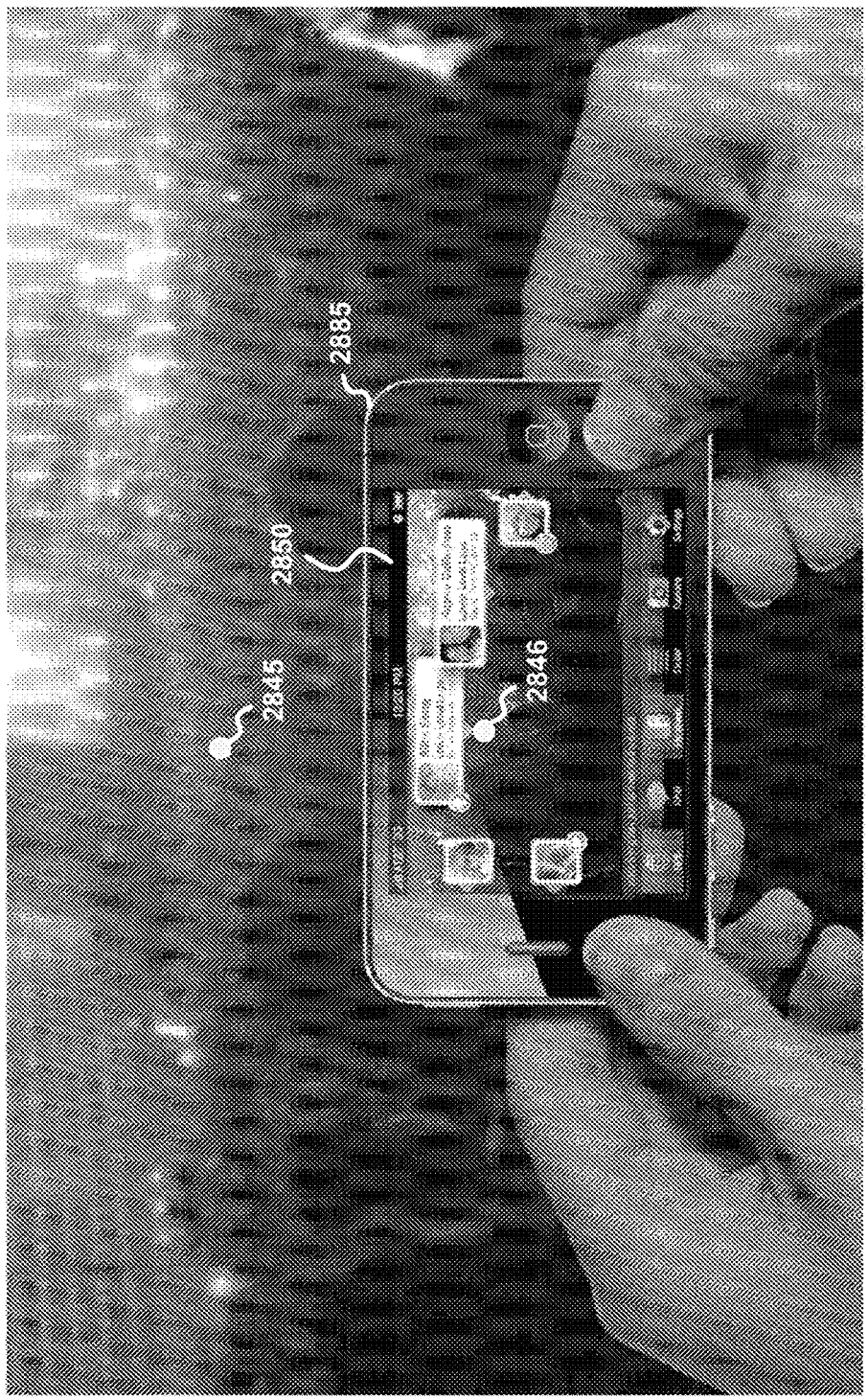
FIG. 28 shows an illustration of a mobile device having an augmented reality interface according to an embodiment.

Within the venue, stage displays can be controlled by a site controller 812, e.g., using stage display(s) controller 1012. The stage displays can play content stored in the site network 816 including pictures, video and sound gathered at the venue or even live. The stage displays 136 could simulcast the performers, or display other recorded content, text, photos, audio, etc. The stage displays 136 include concepts for physical scenic elements that will relay the information that is transmitted to the venue via the site network 116, for example:

A ring of LEDs surrounds the giant lightbulb or other object to relay information from the site network 116 prior to and during the event A strip of LEDs could appear to deliver information that has been gathered from the site network 116 during the show FIG. 28 illustrates an example augmented reality user interface 2850 on a mobile device (e.g., 2885) that some embodiments use to provide a view of a location (e.g., 2845) augmented by computer-generated visual and/or audio information. In this example, a camera of a mobile device (e.g., camera 976 of mobile device 824) is pointed at a view of the location. The mobile device and/or a remote server (e.g., site system 280) in communication with the mobile device, utilizes information from the mobile device to determine (e.g., estimate) what is in the view of the camera. The determination can be based at whole or in part, on:

GPS location information (e.g., from location engine 937).

Cell tower location information (e.g., read using cellular 958 wireless module, and analyzed using handheld controller 910).

WiFi location information (e.g., read using WiFi 952 wireless module, and analyzed using handheld controller 910).

A compass internal to the mobile device (e.g., magnetometer 938) that can provide heading information (e.g., relative to magnetic north).

An accelerometer internal to the device (e.g., accelerometer 932) (which can also be used to provide tilt information).

Gyroscopic orientation information from a gyroscope (e.g., gyroscope 934 being a 2 or 3 axis gyroscope in some embodiments which can provide two or three dimensional attitude information (e.g., pitch, roll, and yaw).

Object recognition performed by analyzing a captured image (e.g., captured by camera 976) to identify landmarks (which may be structural landmarks, such as walls, columns, doorways, seats, and/or may be active or passive beacons, such as coded signs (e.g., where each sign has a unique visual code and the signs are strategically placed are columns, walls, etc.), etc.), faces, etc., and/or other information. This type of visual analysis is discussed further with the description of FIGS. 30-32 below.

Altitude above sea level estimated by barometer 939.

In order to make the determination, some or all of the foregoing information may be used in combination with a 3D map of the location (which may include beacon placement location information, if such exist and/or other landmark identifications and locations) and/or photographs and/or what is actually physically present in the venue as captured via a rear-facing camera lens on the user's smart phone, PDA device, or tablet device. In some embodiments, this information is stored on the mobile device (e.g., in application storage 922), and in some embodiments, this information is retrieved from a server (e.g., from site information storage 1037 in NAS 850 attached to site controller 812).

In particular, some or all of the forgoing information may be used to determine the device's pose (position and orientation). For example, GPS information can be used to determine the latitude and longitude location of the user device, and gyroscopic orientation information can be used to determine the lens angle with reference to ground or other reference point or plane. Upon receiving an indication (e.g., via the application) that the device's camera is active (capturing images), and by knowing the user device pose, and the system can determine what is being displayed on the device's display. Pose is discussed further with the description of FIGS. 30 and 31 below.

Mobile device 824 and/or site system 280 can also obtain information about people at the location (e.g., including identifiers, names and positions in the location) and user friend information (e.g., identifiers/names associated with a user's friends obtained from the ticket system and/or a social network system data stores) which may be compared to determine where and in which seats the user's friends are sitting. The server can forward to the application information as to where in the device display such seat and friend information are to be displayed. The application can then overlay onto the image captured by the camera names, photographs, and/or seat identifiers of the user's friends so that the user can visually see where the user's friends are located using the augmented reality approaches described with FIGS. 29-33 below. The augmented reality system may also receive comments, photographs, and/or videos posted by event attendees during the event, e.g., similar to 2846 shown on augmented reality display 2850.

As shown as 2846, for a given user, using the augmented reality approaches described with FIGS. 29-33 below, embodiments can determine who the user's friends are, and then stream the user's friends' comments, photographs, and/or videos submitted via the application, a short messaging service interface, a social network interface, or otherwise, (and received by the system) in substantially real-time to the user's device for display via the augmented reality user interface.

As described in detail with the description of FIGS. 30-32 below, other types of information may be overlaid onto the camera view, such as highlights or other emphasis around entrances to bathrooms, concessions, other amenities, exits, the user automobile, etc. The emphasis may be visually coded (e.g., color coded, icon coded, etc.), where different codes may be used to identify different features or types of information (e.g., the type of service provided by an amenity (e.g., food, a bathroom, a water fountain, an automated teller machine).

In addition, the system may determine which of the user's friends have arrived at the venue based on an indication that their ticket (which may be a physical ticket, an electronic ticket in their phone, a credit card used to purchase the right to attend, etc.) has been scanned at the venue, via a presence signal received from the friends' mobile communication devices while at the venue (e.g., GPS information provided via a phone app hosted on the friends mobile communication devices), via an affirmative action by the friend (e.g., by activating an "I have arrived" control via an app hosted on the friend's mobile communication device), or otherwise (the system may similarly determine if the user is at the venue). Using approaches described with FIGS. 30-33 below, when the augmented reality device is pointing at a friend's seat, the system may overlay a color coded icon (e.g., color code, icon code, text code, etc.) the seat to indicate the friend has arrived (or that a friend has not arrived if their presence has not been detected). In addition or instead, a list may be presented to the user via an application or web page indicating which of the user's friends have arrived and which have not yet arrived.

In certain embodiments, the ticket system may determine if the user's view includes a performer, may access information regarding the performer, and cause the accessed information to be displayed via the user's augmented reality device displayed over image of the performer.

In certain embodiments, the ticket system may determine if the user's view includes seats for which event tickets have not yet been purchased. Using approaches described herein, the system may identify the seats as being available to the user via an augmented reality indication overlaying the view (e.g., textually, graphically, or otherwise). A control may be provided via which the user can purchase at a specified price, via their device, a ticket/upgrade for the seat, which then may be electronically delivered to their device to be displayed or otherwise communicated to others (e.g., to an usher) to indicate that the user has a right to utilize the seat. Optionally, before indicating to the user that a seat is available, the system may first determine if the seat is a better seat than the user's current seat (e.g., have a better view, is closer to the stage or playing field), based on rankings or other information stored in a database. If the seat is not better (e.g., has a similar, the same, or lower ranking than the user's current seat), optionally the system does not identify the seat as being available to the user.

Figure 29:
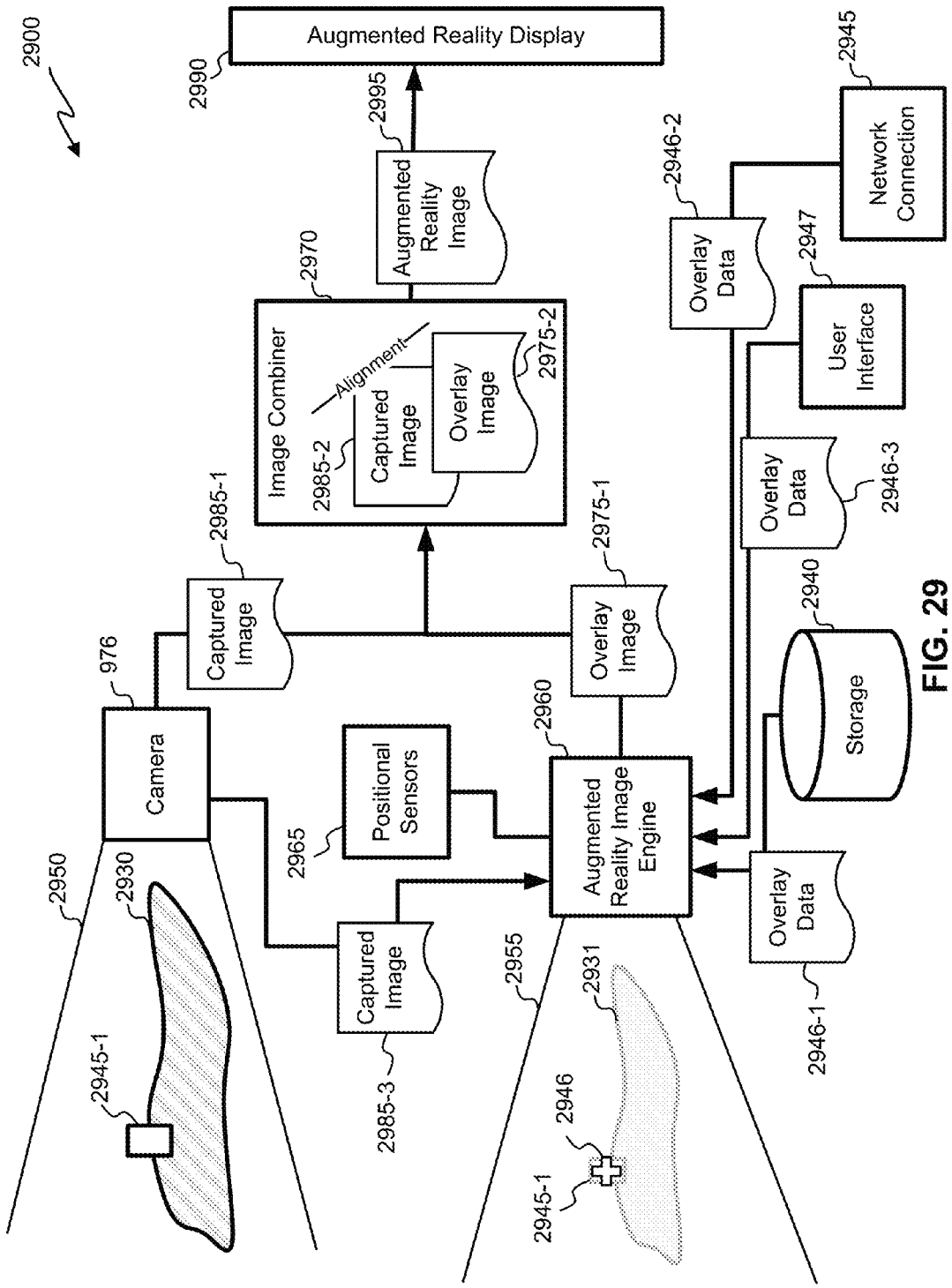
FIG. 29 shows a block diagram of an example system for the generation of augmented reality images according to an embodiment.

FIG. 29 illustrates an example system 2900 for the generation of augmented reality images according to an embodiment of the present invention. In some embodiments, augmented reality image generated by system 2900 is similar to augmented reality image 2850 from FIG. 28, and is generated by a mobile device 824 (e.g., mobile device 824) having components similar to those illustrated in FIG. 9.

In some embodiments, positional sensors determine a geographic position the mobile device within a geographic area. For example, some positional sensors 2965 (e.g., a GPS in location engine 937) can determine an absolute geographic location, and/or some positional sensors 2965 can determine a relative location within a bounded geographic area, e.g., wireless modules 950 can determine a location using wireless signal geolocation.

In an example embodiment, mobile device 824 can enable the selection of and guidance to, a particular destination within the geographic area. As discussed with the description of FIG. 9 above, different types of information may be overlaid onto the camera view, such as highlights of amenities at the geographic location (e.g., a venue) and the different types of service provided by an amenity (e.g., food, a bathroom, a water fountain, an automated teller machine). In some embodiments, these different services provided by a destination correspond to different types of destinations.

In some embodiments, the geographic area is bounded, having a limited area, and different destinations within the bounded area can be selected by a user interface 2947 (e.g., a user interface stored in application storage 922) for highlighting by the augmented reality display. Using user interface 2947, for example, a type of destination can be selected, and different destinations corresponding to the selected type can be identified, one or more of these destinations being shown on the augmented reality display in a way similar to augmented reality display 2850 from FIG. 28.

In some embodiments, the types of destinations, and information about the destinations can be stored in, and retrieved from storage 2940 (e.g., similar to application storage 922). In some embodiments, this destination information can be retrieved by using network connection 2945 (e.g., using wireless modules 950 of mobile device 824) from network storage (e.g., site feature data storage 1039 in NAS 850). In some embodiments, this information provides the name and location of destinations within the geographic area, and this information is used by some embodiments to provide information using user interface 2947, and generate an augmented reality image the includes the destinations.

Some embodiments generate augmented reality image 2995 (e.g., a combination of a camera view and graphic highlights, similar to augmented reality display 2850), two different images, termed herein a captured image (e.g., captured image 2985 captured by camera 976) and an overlay image (e.g., overlay image 2975) are combined. Broadly speaking, the overlay image overlays computer generated graphics over the captured image to produce augmented reality image 2995.

To overlay graphics in an overlay image accurately over features in a captured image, the overlay image (e.g., overlay image 2975) is generated by an augmented reality engine 2960 coordinating the different processed described herein. In some embodiments, part or all of augmented reality engine 2960 can be generated by handheld controller 910 executing computer-executable code retrieved by storage controller 920 from in code storage 926. As discussed further below, parts of augmented reality engine 2960 can be enabled by mobile device 824 hardware components (e.g., motion coprocessor 915, 3-D Engine 916, physics engine 917, graphics processor 968, and/or other similar components.

In an example, to display augmented reality image 2995, camera 976 captures captured image 2985-1. It should be appreciated that, even though augmented reality display 2990 is discussed showing a single, still augmented reality image 2995, some embodiments can perform different processes described herein with full motion video, such video being a collection of still images, the still images making up the full motion video.

Continuing this example, at the time captured image 2985-1 is captured, the "pose" of mobile device 824 is estimated. In some embodiments, this camera pose (or just pose), includes one or more of the geographic location of the mobile device, the 3-D orientation of the mobile device, as well as the compass direction (e.g., as measured by magnetometer 938) and the altitude of the mobile device (e.g., as measured by barometer 939).

Continuing this example, once a camera pose is determined, user input is analyzed and storage is accessed to determine which objects should be highlighted. In some embodiments, to place points of interest properly in overlay image 2975-1, augmented reality engine 2960 can use a virtual camera 2955. In this example, the geographic position determined by mobile device 824 combined with the camera pose from determines that mobile device 824 is overlooking venue 2930 and point of interest 2945-1 (also termed features, and/or destination) is in the field of view. With further processing it can be determined by the virtual camera 2955 approach that point of interest 2945-1 should be highlighted (e.g., the "reality" of captured image 2985-1 should be augmented by graphical icon 2946 in overlay image 2975-1).

Once all the highlighted features are selected, and the graphical icons are properly placed, overlay image 2975-1 can be generated. As will be discussed in greater detail with the description of FIGS. 30-32 below, captured image 2985-2 and overlay image 2975-2, are respectively captured and generated using the same camera pose. To generate augmented reality image 2995, captured image 2985-2 and overlay image 2975-2 are combined, e.g., with an alignment that places highlight icons over the points of interest. In some embodiments, image combiner 2970 uses different approaches to receive captured image 2985-1 and overlay image 2975-1, and align the received images such that the graphical highlights of image 2975-1 are aligned with their corresponding physical features captured in captured image 2985-1. Example approaches to this alignment are discussed below with FIG. 30.

This combination and alignment can also be termed "registration" in some embodiments, and the process can happen frequently, e.g., in full motion video embodiments.

Figure 30:
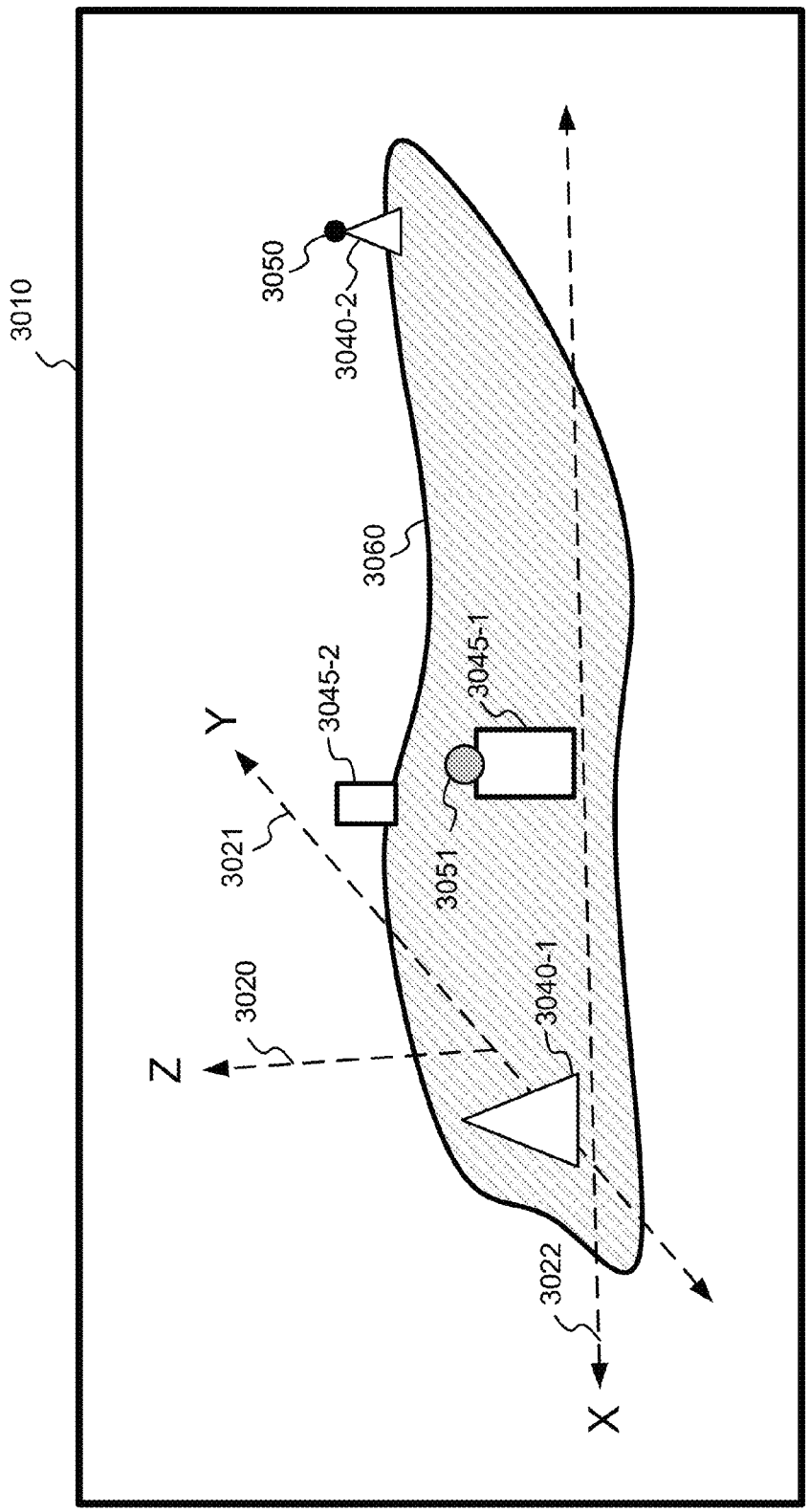
FIG. 30 illustrates an example captured image, according to an embodiment.

FIG. 30 illustrates an example captured image 3010 (e.g., captured image 2985-1 from FIG. 29), as captured by a camera (e.g., camera 976 of mobile device 824 shown FIG. 9). As noted above, in some embodiments, augmented reality display 2990 shows a succession of generated augmented reality images 2995 resulting in a full-motion video display of reality, augmented with icons attached to features on a landscape. In this example, image 3010 can be a still image, or a frame of a video stream displayed on mobile device 824 showing landscape 3060.

In this example, landscape 3060 is at a location where a user of mobile device 824 seeks to differentiate between two types of destinations, such example destinations being represented as simple shapes in FIG. 30 (shown as rectangle 3045 and triangle 3040 on landscape 3060). In an embodiment rectangle 3045 is a representation of a concession and triangle 3040 is a representation of a restroom. It should be appreciated that landscape 3060 is shown (as it would be on augmented reality display 2990 (e.g., display 965 on mobile device 824)) a two dimensional representation of a three dimensional scene. To improve the rendering of landscape 3060 in FIG. 30, X 3022, Y 3021 and Z 3023 axes are shown, though these need not be displayed in embodiments.

As discussed above with FIG. 29, in some embodiments, one or more types of overlay image generation are used to generate overlay image 2975-2. One way uses the pose of a camera that captures the captured image for which the overlay image is to be generated (e.g., as determined by positional sensors 2965) at the time captured image (e.g., captured image 2985-2) was captured. This approach, using positional sensors and a determined camera pose, is termed herein as an "inertial" approach. As discussed above, a camera pose can include a combination of a geographical position (e.g., determined by location engine 937), a camera direction (e.g., determined by magnetometer 938), altitude (e.g., as determined by barometer 939), and a three dimensional representation of the orientation of mobile device 824 (e.g., determined by one or more gyroscopes 934). It would be appreciated by one having skill in the relevant art(s), given the description herein, that the example camera pose described above can be combined with geographic location information of a landscape 3060 feature (e.g., restroom 3040-1) to select the placement of a representative graphical icon in overlay image 2975-1. In some embodiments, this geographical information can be received as overlay data 2946-1 from storage 2940 (e.g., application storage 922) or received as overlay data 2946-2 from network connection 2945 (e.g., using wireless modules 950 to receive from site controller 812). In some embodiments, network connection 2945 receives geographic location information from the points of interest themselves, e.g., as wireless transmissions of data using BLE or other technology.

In selecting the placement of the representative graphical icon in the overlay image, some embodiments of handheld controller use one or more of motion coprocessor 915, 3D engine 316 and physics engine 317.

Another approach to the generation of overlay image 2975-1 uses a visual analysis of a captured image (e.g., captured image 2985-3 received at augmented reality engine 2960 from camera 976) to identify points of interest in the captured image for subsequent overlay of graphical highlights. In some embodiments, this visual analysis is assisted by different visual markers attached to points of interest. These markers are shown in FIG. 30 as marker 3050 and marker 3051, respectively marking concession 3045-1 and restroom 3040-2. The markers are different from each other in this example, to relay an indication to augmented reality engine 2960 of the particular type of destination they mark. Thus, in a visual analysis of scene 3010, markers 3050 and 3051 are detected by augmented reality engine 2960 and their position in scene 3010 is used to place appropriate (e.g., by destination type) graphical highlights in overlay image 2975-1. One having skill in the relevant art(s), given the description herein, would appreciate how a captured image (e.g., captured image 3010) can be analyzed to detect a visual indicator, and how this indicator can be used to overlay graphical highlights on features to which the markers are attached. This approach can be termed herein a "visual approach" to augmented reality.

It should be noted that a combination of visual and inertial approaches can be used to generate overlay image 2975-1. For example, only a portion of the points of interest in scene 3010 have markers to enable visual analysis of the scene. Once overlay image 2975-1 is generated, in some embodiments, overlay image 2975-1 is relayed to image combiner 2970 and combined with captured image 2980-2 for display as augmented reality image 2995.

Figure 31:
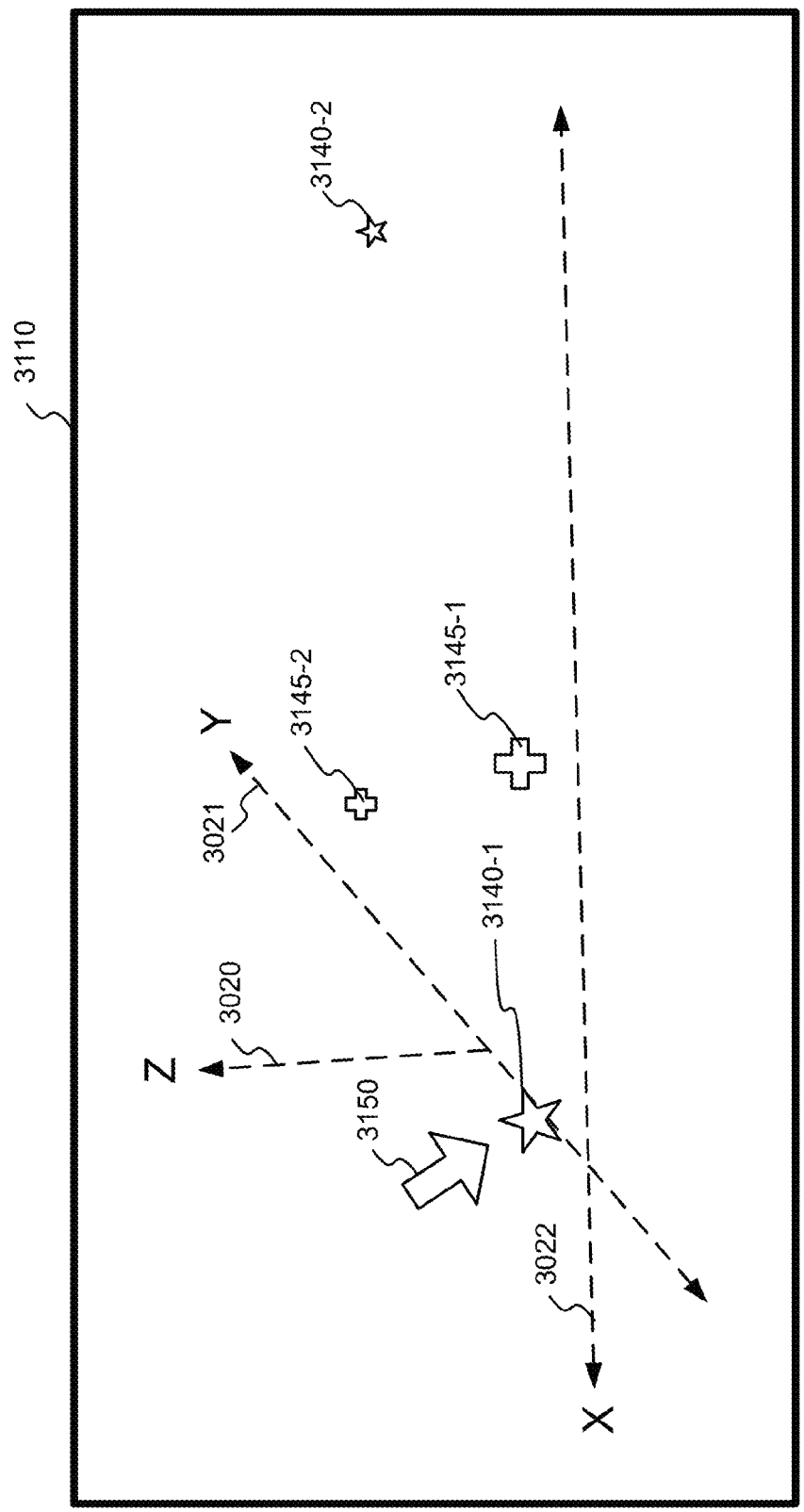
FIG. 31 illustrates an example overlay image, according to an embodiment.

FIG. 31 illustrates an example overlay image 3110 generated to be combined with captured image 3110. As with FIG. 30, to improve the explanation shown in FIG. 30, X 3022, Y 3021 and Z 3023 axes are shown, though these need not be displayed in embodiments. The term "overlay image" is used herein for convenience, because, in some embodiments, when captured image 3010 and overlay image 3110 are combined the effect is that the graphical icons in overlay image 3110 are superimposed (i.e., overlaid) over highlighted elements in the captured image.

As discussed above with FIG. 29, in some embodiments, one or more types of overlay image generation are used to generate overlay image 2975-2. One way uses the pose of a camera that captures the captured image for which the overlay image is to be generated (e.g., as determined by positional sensors 2965) at the time captured image (e.g., captured image 2985-2) was captured. This approach, using positional sensors and a determined camera pose, is termed herein as an "inertial" approach. As discussed above, a camera pose can include a combination of a geographical position (e.g., determined by location engine 937), a camera direction (e.g., determined by magnetometer 938) and a three dimensional representation of the orientation of mobile device 824 (e.g., determined by one or more gyroscopes 934). It would be appreciated by one having skill in the relevant art(s), given the description herein, that the example camera pose described above can be combined with geographic location information of a landscape 3060 feature (e.g., restroom 3040-1) to select the placement of a representative graphical icon in overlay image 2975-1. In some embodiments, this geographical information can be received as overlay data 2946-1 from storage 2940 (e.g., application storage 922) or received as overlay data 2946-2 from network connection 2945 (e.g., using wireless modules 950 to receive from site controller 812). In some embodiments, network connection 2945 receives geographic location information from the points of interest themselves, e.g., as wireless transmissions of data using BLE or other technology.

In selecting the placement of the representative graphical icon, some embodiments of handheld controller use one or more of motion coprocessor 915, 3D engine 316 and physics engine 317.

Another approach to the generation of overlay image 2975-1 uses a visual analysis of a captured image (e.g., captured image 2985-3 received at augmented reality engine 2960 from camera 976) to identify points of interest in the captured image for subsequent overlay of graphical highlights. In some embodiments, this visual analysis is assisted by different visual markers attached to points of interest. These markers are shown in FIG. 30 as marker 3050 and marker 3051, respectively marking concession 3045-1 and restroom 3040-2. The markers are different from each other in this example, to relay an indication to augmented reality engine 2960 of the particular type of destination they mark. Thus, in a visual analysis of scene 3010, markers 3050 and 3051 are detected by augmented reality engine 2960 and their position in scene 3010 is used to place appropriate (e.g., for their type) graphical highlights in overlay image 2975-1. One having skill in the relevant art(s), given the description herein, would appreciate how a captured image (e.g., captured image 3010) can be analyzed to detect a visual indicator, and how this indicator can be used to overlay graphical highlights on features to which the markers are attached. This approach can be termed herein a "visual approach" to augmented reality.

It should be noted that a combination of visual and inertial approaches can be used to generate overlay image 2975-1. For example, as noted above, only a portion of the points of interest in scene 3010 have markers to enable visual analysis of the scene. Once overlay image 2975-1 is generated, in some embodiments, overlay image 2975-1 is relayed to image combiner 2970 and combined with captured image 2980-2 for display as augmented reality image 2995.

In an embodiment, arrow 3150 highlights one graphical icon (e.g., 3140-1) of the many graphical icons in overlay image 3110. As described with FIG. 27 in the incorporated '292 Application, many different types of physical features can be displayed, using embodiments discussed herein, e.g., available seats, friends at the location, concessions, exits, and/or other items useful to locate.

In one example, restrooms are available at a location with a desirability based on a combination of different factors (e.g., queue length and distance from the mobile device). After restrooms are selected as a destination type, destinations of the restroom type (e.g., 3040-1 and 3040-2) could be identified (e.g., by site controller 812 using information stored in site information storage 1037). In some embodiments, information about these destinations could also be stored on mobile device 824 (e.g., in application storage 922).

Once different destinations have been identified, some embodiments can identify information about the destinations that could reflect on their evaluation (e.g., queue length to access the destination). Different example approaches to monitoring queue length by a server (e.g., by site controller 812) are described in the '292 Application. In an augmented reality example, operating on mobile device 824, current queue lengths could be sent from site controller 812 to mobile device 824. Based on this information, and other information (e.g., distance from mobile device 824 to each destination), handheld controller 910 can evaluate the available destinations and select one or more for highlighting (e.g., 3150) as a selected destination. In some embodiments, this analysis can be performed by site controller 812 and results can be transferred to mobile device 824 for display.

One having skill in the relevant art(s), given the description herein, will appreciate that the identification of a type of destination, identification of destinations of the type, identification of information for evaluating (e.g., ranking) the destinations, and selection of one or more destinations to highlight can be performed at different times in the augmented reality image generation process described with FIGS. 29-33.

Figure 32:
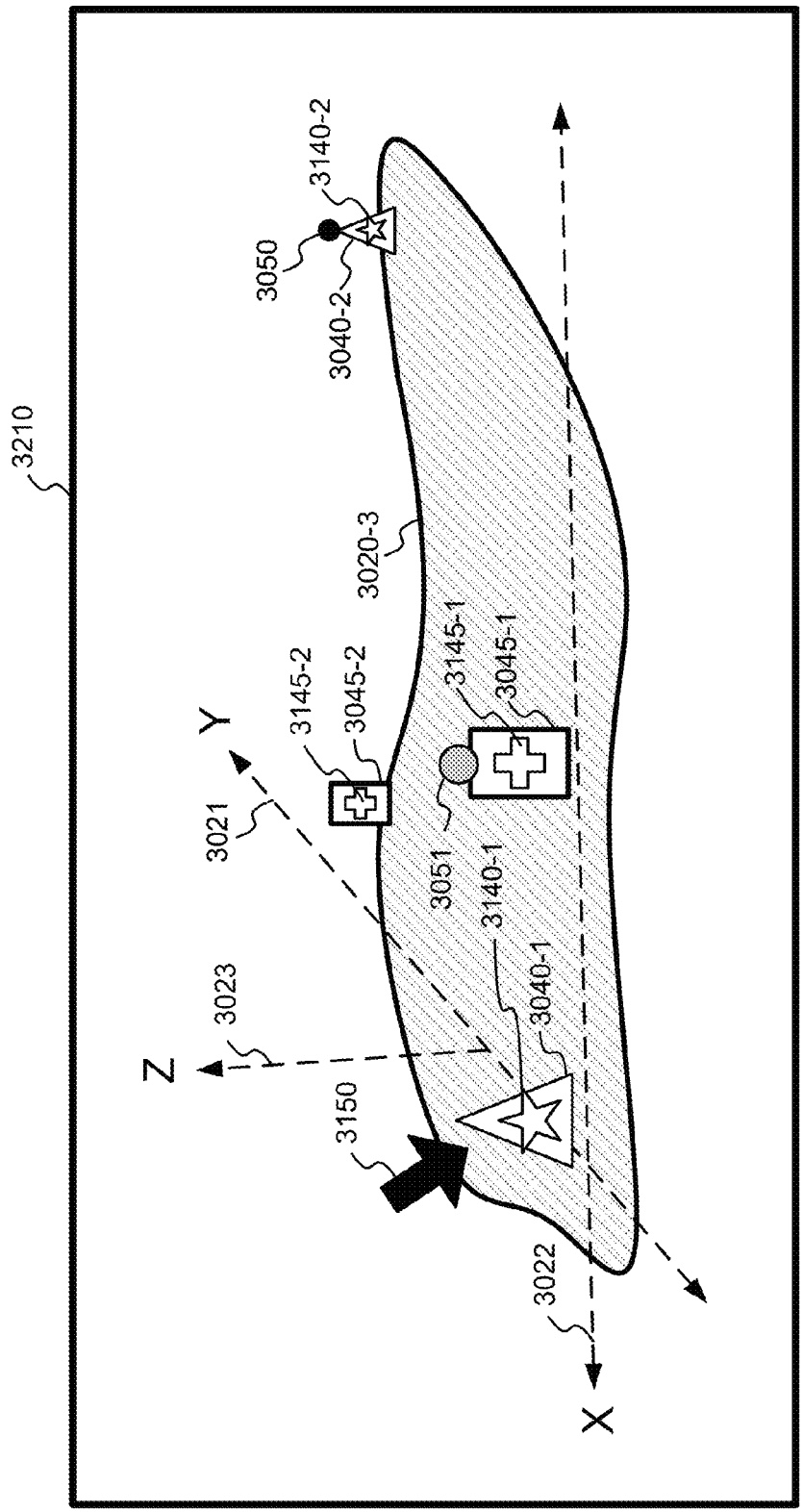
FIG. 32 shows a diagram of an augmented reality image according to an embodiment.

FIG. 32 illustrates a combination of captured image 3010 and overlay image 3110. In some embodiments, once captured image 3010 is captured and overlay image 3110 is generated the two images are combined to form an augmented reality image (e.g., augmented reality image 3210). It should be noted that, as shown on FIG. 32, graphical icons from overlay image 3110 are shown over their respective physical features from captured image 3010 (e.g., restroom icon—1 overlaying restroom 3040-1).

In some embodiments, to achieve the combination of captured image 3010 and overlay image 3110, the two images aligned such that the graphical highlights (e.g., restroom icon 3140-1) are properly aligned with their corresponding physical features (e.g., restroom 3040-1). In an example embodiment, this alignment is performed by image combiner 2970. FIG. 29 shows captured image 2985-2 and overlay image 2975-2 subject to an alignment operation.

In some embodiments, a combination of one or more types of image alignment approaches are used to align captured image 2985-2 and overlay image 2975-2. One type of image alignment uses the pose of camera 976 (e.g., as determined by positional sensors 2965) at the time captured image 2985-2 was generated. As discussed above, an example camera pose includes a combination of a geographical position (e.g., determined by location engine 937), a camera direction (e.g., determined by magnetometer 938) and a three dimensional representation of the orientation of mobile device 824 (e.g., determined by one or more gyroscopes 934). It would be appreciated by one having skill in the relevant art(s), given the description herein, that the example camera pose described above can be combined with geographic location information of landscape 3060 features (e.g., the location of restroom 3040-1) to enable the alignment of the captured features and overlaid elements. In some embodiments, 3D engine 916 can provide 3D alignment processing, and handheld controller 910 can use edge-detection approaches available, for example, from code storage 926.

Just as a visual analysis approach can be used to generate overlay image 3110 (e.g., as described above with the description of FIG. 31), a visual analysis approach can also be used to align captured image 3010 and overlay image 3110. For example, during an alignment stage, marker 3051 (e.g., marking concession 3045-1) can provide an alignment point in captured image 3010 to which concession icon 3145-1 can be attached. It should be noted that, as with the generation of overlay image 2975-1 discussed above with FIG. 30, a combination of visual and inertial approaches can be used to align captured image 3010 and overlay image 3110. For example, only a portion of the points of interest in scene 3010 have markers to enable visual analysis of the scene.

It would be appreciated by one having skill in the relevant art(s), given the description herein, that the alignment of captured image 3010 and overlay image 3110 need not be exact, as some level of inaccuracy is tolerable in augmented reality displays 2990, e.g., augmented reality icons can be shown near their respective physical features without detracting from the value of an augmented reality display.

Figure 33:
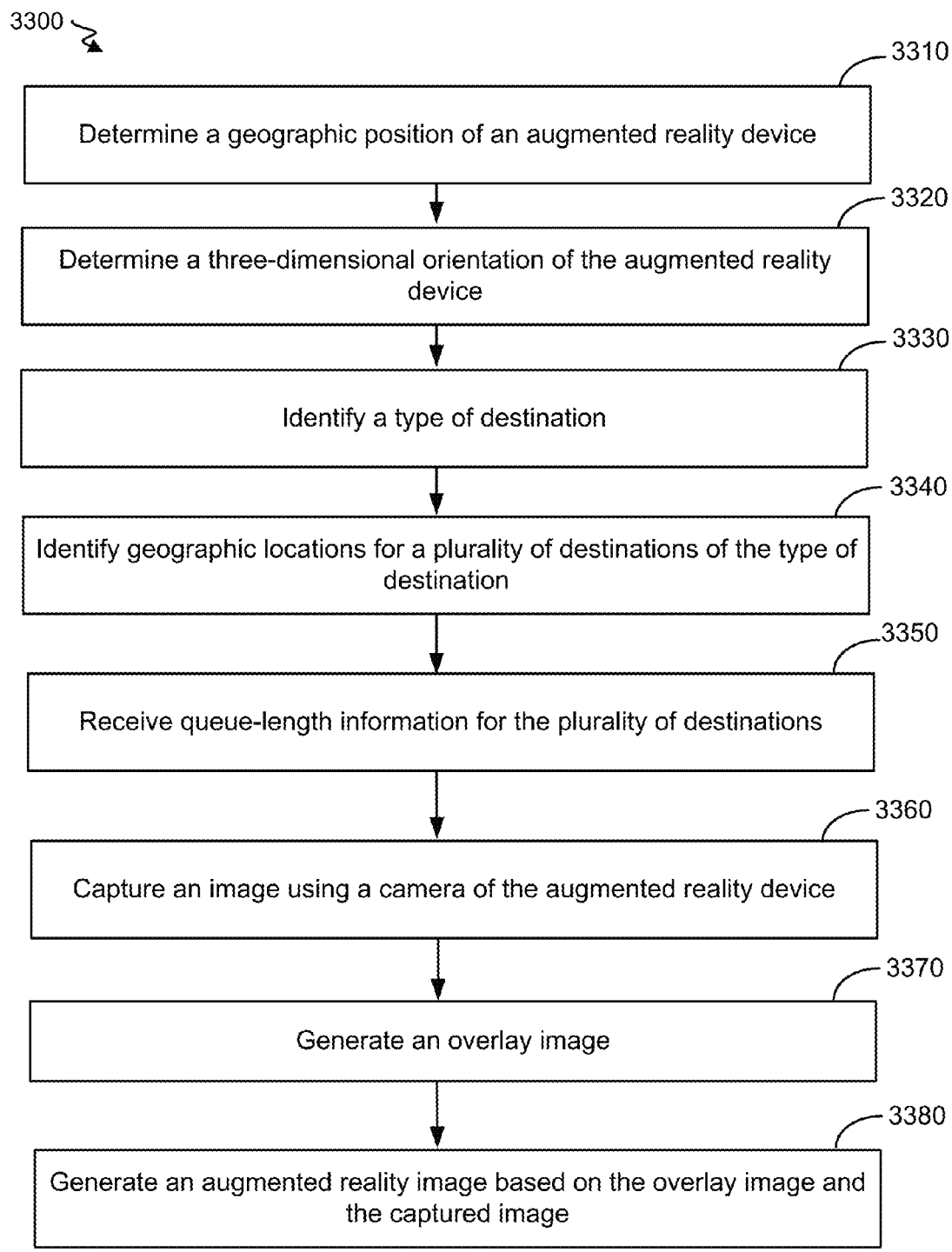
FIG. 33 illustrates a flowchart of an embodiment of a process for generating augmented reality images according to an embodiment.

FIG. 33 illustrates a flowchart of an embodiment of a process 3300 for using sensor data and location data from an augmented reality device to generate augmented reality images. Process 3300 can be performed in part or in its entirety by the augmented reality device (e.g., mobile device 824). The augmented reality device can be any device having the types of sensors described with respect to different embodiments described herein, including those described with FIGS. 8 and 9 above. The geographic position can be determined using signals received from a GPS satellite, a WiFi access point, a cell tower, a Bluetooth signal generator and/or any other radio signal transmission. The signal may include data indicative of a location of the device (e.g., a satellite identifier or GPS coordinates), and/or the signal strength may be assessed and a geographic position determined from known approaches.

Process 3300 begins at block 3310, where a geographic position of an augmented reality device is determined. The geographic position can be, for example, a geographic position on earth (e.g., using latitude and longitude), or a position relative to a location having boundaries (e.g., reference to coordinates on a plot of land, inside a building, and/or other similar area. Geographic position can also include the direction that the augmented reality device is oriented (e.g., in related to compass points). This geographic position can be determined by use of, for example, magnetometer 939 and/or an analysis of beacons at a location indicating the direction mobile device 824 is facing. When a geographic location is determined within a discrete area (e.g., on on a plot of land, inside a building, in a stadium and/or other similar areas), this can be termed a geographic location within a bounded geographic area. As used by some embodiments, geographic location also can include the compass direction of the mobile device.

At block 3320, a three-dimensional orientation of the augmented reality device is determined. Three-dimensional orientation of the augmented reality device can be determined by position sensors on the device, including those shown in FIG. 5, e.g., gyroscope 934, and/or other approaches to determining the orientation of a device. Gyroscope 934 can provide a measurement of the rotation in rad/s around each of the three physical axes (x, y and z), and, in some embodiments, a gravity sensor (not shown) can measures the force of gravity in m/s$^2$ that is applied to a device on all three physical axes (x, y, z).

At block 3330, a type of destination is identified. Destination type can refer to a destination in the type of bounded area described above. Example destinations within a bounded area can include geographic features (mountains, rivers, and/or other feature), specific location inside and outside buildings (e.g., entrances, exits, restrooms, specific offices, concession stands, and/or other similar features). In some circumstances, there may be several destinations (e.g., restroom A, restroom B) of the type of destination (e.g., restrooms) at a location. The selection can be from a user, for example, based on an interest in moving to one or more of the several destinations of the type of destination. In some embodiments, this selection being made using a user interface, voice-recognition, and/or other input approaches.

At block 3340, geographic positions for a plurality of destinations of the type of destination are identified. Similar to the geographic positions discussed with stage 3310 above, the geographic positions of the destinations can be absolute (e.g., latitude and longitude), and/or relative to the bounded location (e.g., relative to the bounds of a bounded area). The positions can be identified by retrieving information stored on the augmented reality device (e.g., retrieved from application storage 922 from FIG. 9), and/or received from a central server (e.g., retrieved by site controller 812 from site information storage 1037).

The geographic positions of destinations can be fixed (e.g., restrooms at a location are generally fixed in the location and don't change), and/or variable (e.g., a roving food-cart can have a geographic position that periodically changes). Some embodiments store geographic locations for relatively immobile destinations and infrequently modify this stored data (e.g., to add and remove destinations), while some embodiments identify geographic positions of destinations from frequently updated sources (e.g., a server the receives GPS updated location information from a food-cart). The need for updating geographic positions for use within block 3340 can influence where such data is stored (e.g., frequently updated data can be retrieved from a server (e.g., site controller 812), and less frequently updated information can be retried from a data stored locally on the augmented reality device (e.g., from application storage 922).

At block 3350, queue length information is received for the plurality of destinations.

Queue length information can reference an ordered list of requests to use a resource, e.g., a queue of threads waiting to use a microprocessor. Queue length can also refer to other types of ordered resource allocation, such as people physically arranging themselves in a line to access a particular resource at a location. In this example, the resource can be the destination described herein.

With reference to the augmented reality device, queue length can be received from an external source (e.g., site controller 812), based on a request for data, and/or not based on a request for data. For example, having selected a destination type (e.g., a type of resource to be accessed, a server can retrieve and transmit to the augmented reality device information corresponding to the number of requests currently pending to access the resource, e.g., for resource A, five requests are pending for access to the resource). Where the destination type is a particular location-based resource (e.g., a concession, restroom, entrance, exit, and or other destinations at a location), queue length information can correspond to the number of people currently waiting to access each of the resources.

At block 3360, an image is captured using a camera of the augmented reality device. In some embodiments, a single image is captured, and the processes described herein commence, and are completed with the single image. In some embodiments, the image captured at this block is one of many images that compose a dynamically updated display (e.g., full-motion video), and the processes described with FIG. 33, and other embodiments, can result in a full motion augmented reality display shown using the augmented reality device.

At block 3370, an overlay image is generated. In some embodiments, as described with FIGS. 29-32 above, a combination of positional data for the augmented reality device (e.g., geographic location and three dimensional orientation) are combined with overlay data (e.g., the geographic locations of one or more destinations) to generate an overlay image for use creating an augmented reality image. As noted above, this overlay image can be a single image, or one image of a sequence of images used to create a dynamic, full-motion video display.

At block 3380, an augmented reality image is generated based on a combination of the captured image and the overlay image. As noted with the description of FIG. 32 above, alignment of the images facilitates the proper highlighting of selected destinations.

Specific details are given in the above description to provide a thorough understanding of the embodiments. However, it is understood that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Implementation of the techniques, blocks, steps and means described above may be done in various ways. For example, these techniques, blocks, steps and means may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments may be described as a process which is depicted as a flowchart, a flow diagram, a swim diagram, a data flow diagram, a structure diagram, or a block diagram. Although a depiction may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, network transmission, etc.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed is:

1. A method of using sensor data and location data from a device to generate augmented reality images, the method comprising:
    determining a geographic position of a mobile device, the mobile device being within a bounded geographic area, the bounded geographic area having a plurality of destinations, each destination being of a type of a plurality of types of destination;
    determining a three-dimensional orientation of the mobile device;
    identifying a type of destination of the plurality of types of destinations;
    transmitting a first communication to a server, the first communication including an identification of the identified type of destination;
    identifying a plurality of destinations associated with the identified type of destination;
    receiving, by the mobile device, a second communication from the server, the communication including queue-length information associated with the identified plurality of destinations;
    identifying a geographic position for each of the identified plurality of destinations;
    capturing a first image using a camera of the mobile device;
    generating a second image based on:
        the geographic position of the mobile device,
        the three-dimensional orientation of the augmented reality device,
        the queue-length information associated with the identified plurality of destinations, and
        the geographic position at least one of the identified plurality of destinations;
    generating an augmented reality image based on the first image and the second image; and
    displaying the augmented reality image.

2. The method of using sensor data and location data from a device to generate augmented reality images as recited in claim 1, wherein receiving queue-length information associated with the identified plurality of destinations comprises receiving an estimated queue length for each of the identified plurality of destinations, and the method further comprises:
    performing a comparison to select a destination of the identified plurality of destinations, the comparison being based on the estimated queue-lengths; and
    selecting a destination of the plurality of destinations, the selection based on the estimated queue-lengths, wherein generating a digital image based on queue-length information associated with the plurality of destinations comprises generating a digital image having the selected destination visually highlighted.

3. The method of using sensor data and location data from a device to generate augmented reality images as recited in claim 1, wherein determining a geographic position of an augmented reality device comprises:
    identifying a latitude and a longitude measurement from a global positioning system (GPS) sensor in the augmented realty device;
    identifying a map associated with the latitude and longitude measurements; and
    combining the latitude and longitude measurements with the map to determine the geographic position of the augmented reality device.

4. The method of using sensor data and location data from a device to generate augmented reality images as recited in claim 1, wherein determining a three-dimensional orientation of the augmented reality device comprises determining a three-dimensional orientation of the augmented reality device using a gyroscope of the augmented reality device.

5. The method of using sensor data and location data from a device to generate augmented reality images as recited in claim 4, wherein determining a three-dimensional orientation of the augmented reality device further comprises determining a three-dimensional orientation of the augmented reality device using a compass of the augmented reality device.

6. The method of using sensor data and location data from a device to generate augmented reality images, as recited in claim 1, further comprising determining movement information associated with the augmented reality device, wherein generating a digital image further comprises generating a digital image based on the determined movement information.

7. The method of using sensor data and location data from a device to generate augmented reality images, as recited in claim 6, wherein determining movement information associated with the augmented reality device comprises determining movement information associated with the augmented reality device using an accelerometer of the augmented reality device.

8. The method of using sensor data and location data from a device to generate augmented reality images, as recited in claim 1, further comprising identifying, based on the geographic position of the augmented reality device and the geographic position of each of at least one of the identified plurality of destinations, a closest destination of the identified plurality of destinations, wherein generating the second image based on the geographic position of each of at least one of the identified plurality of destinations comprises generating the second image having the closest destination visually highlighted.

9. The method of using sensor data and location data from a device to generate augmented reality images, as recited in claim 1, wherein identifying a type of destination of the plurality of types of destinations comprises receiving, by the augmented reality device, a selection of the type of destination.

10. A computer-program product tangibly embodied in a non-transitory machine-readable storage medium, including instructions configured to cause one or more data processors to perform actions including:
    determining a geographic position of a mobile device, the mobile device being within a bounded geographic area, the bounded geographic area having a plurality of destinations, each destination being of a type of a plurality of types of destination;
    determining a three-dimensional orientation of the mobile device;
    identifying a type of destination of the plurality of types of destinations;
    transmitting a first communication to a server, the first communication including an identification of the identified type of destination;
    identifying a plurality of destinations associated with the identified type of destination;
    receiving, by the mobile device, a second communication from the server, the communication including queue-length information associated with the identified plurality of destinations;
    identifying a geographic position for each of the identified plurality of destinations;

capturing a first image using a camera of the mobile device;
generating a second image based on:
the geographic position of the mobile device,
the three-dimensional orientation of the augmented reality device,
the queue-length information associated with the identified plurality of destinations, and
the geographic position at least one of the identified plurality of destinations;
generating an augmented reality image based on the first image and the second image; and
displaying the augmented reality image.

11. The computer-program product as recited in claim 10, wherein receiving queue-length information associated with the identified plurality of destinations comprises receiving an estimated queue length for each of the identified plurality of destinations, and the actions further include:
performing a comparison to select a destination of the identified plurality of destinations, the comparison being based on the estimated queue-lengths; and
selecting a destination of the plurality of destinations, the selection based on the estimated queue-lengths, wherein generating a digital image based on queue-length information associated with the plurality of destinations comprises generating a digital image having the selected destination visually highlighted.

12. The computer-program product as recited in claim 10, wherein determining a geographic position of an augmented reality device comprises:
identifying a latitude and a longitude measurement from a global positioning system (GPS) sensor in the augmented realty device;
identifying a map associated with the latitude and longitude measurements; and
combining the latitude and longitude measurements with the map to determine the geographic position of the augmented reality device.

13. The computer-program product as recited in claim 10, wherein determining a three-dimensional orientation of the augmented reality device comprises determining a three-dimensional orientation of the augmented reality device using a gyroscope of the augmented reality device.

14. The computer-program product as recited in claim 13, wherein determining a three-dimensional orientation of the augmented reality device further comprises determining a three-dimensional orientation of the augmented reality device using a compass of the augmented reality device.

15. The computer-program product as recited in claim 10, wherein the actions further include: determining movement information associated with the augmented reality device, wherein generating a digital image further comprises generating a digital image based on the determined movement information.

16. The computer-program product as recited in claim 15, wherein determining movement information associated with the augmented reality device comprises determining movement information associated with the augmented reality device using an accelerometer of the augmented reality device.

17. The computer-program product as recited in claim 10, wherein the actions further include: identifying, based on the geographic position of the augmented reality device and the geographic position of each of at least one of the identified plurality of destinations, a closest destination of the identified plurality of destinations, wherein generating the second image based on the geographic position of each of at least one of the identified plurality of destinations comprises generating the second image having the closest destination visually highlighted.

18. The computer-program product as recited in claim 10, wherein identifying a type of destination of the plurality of types of destinations comprises receiving, by the augmented reality device, a selection of the type of destination.

19. A system for using sensor data and location data from a device to generate augmented reality images, the system comprising:
a processor; and
a memory in communication with the processor for tangibly storing a plurality of processing instructions for directing the processor to:
determine a geographic position of a mobile device, the mobile device being within a bounded geographic area, the bounded geographic area having a plurality of destinations, each destination being of a type of a plurality of types of destination;
determine a three-dimensional orientation of the mobile device;
identify a type of destination of the plurality of types of destinations;
transmit a first communication to a server, the first communication including an identification of the identified type of destination;
identify a plurality of destinations associated with the identified type of destination;
receive, by the mobile device, a second communication from the server, the communication including queue-length information associated with the identified plurality of destinations;
identify a geographic position for each of the identified plurality of destinations;
capture a first image using a camera of the mobile device;
generate a second image based on:
the geographic position of the mobile device,
the three-dimensional orientation of the augmented reality device,
the queue-length information associated with the identified plurality of destinations, and
the geographic position at least one of the identified plurality of destinations;
generate an augmented reality image based on the first image and the second image; and
display the augmented reality image.

20. The system for using sensor data and location data from a device to generate augmented reality images as recited in claim 19, wherein the processing instruction to receive queue-length information associated with the identified plurality of destinations comprises receiving an estimated queue length for each of the identified plurality of destinations, and the actions further include:
performing a comparison to select a destination of the identified plurality of destinations, the comparison being based on the estimated queue-lengths; and
selecting a destination of the plurality of destinations, the selection based on the estimated queue-lengths, wherein generating a digital image based on queue-length information associated with the plurality of destinations comprises generating a digital image having the selected destination visually highlighted.

* * * * *